(12) United States Patent
Lai et al.

(10) Patent No.: US 12,127,521 B2
(45) Date of Patent: Oct. 29, 2024

(54) MALE STERILITY MAINTAINER LINE PLANT AND USE THEREOF

(71) Applicant: CHINA AGRICULTURAL UNIVERSITY, Beijing (CN)

(72) Inventors: Jinsheng Lai, Beijing (CN); Haiming Zhao, Beijing (CN); Weibin Song, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 118 days.

(21) Appl. No.: 17/618,027

(22) PCT Filed: Jun. 9, 2020

(86) PCT No.: PCT/CN2020/095082
§ 371 (c)(1),
(2) Date: Dec. 10, 2021

(87) PCT Pub. No.: WO2020/248969
PCT Pub. Date: Dec. 17, 2020

(65) Prior Publication Data
US 2022/0256793 A1    Aug. 18, 2022

(30) Foreign Application Priority Data
Jun. 10, 2019  (CN) .......................... 201910496386.2

(51) Int. Cl.
C12N 15/82   (2006.01)
A01H 1/02    (2006.01)
A01H 6/46    (2018.01)

(52) U.S. Cl.
CPC .......... *A01H 1/023* (2021.01); *A01H 6/4684* (2018.05); *C12N 15/8289* (2013.01)

(58) Field of Classification Search
None
See application file for complete search history.

(56) References Cited

U.S. PATENT DOCUMENTS

| | | | | |
|---|---|---|---|---|
| 5,880,331 | A | * 3/1999 | Krebbers | ........... C12N 15/8289 800/274 |
| 2014/0338071 | A1 | 11/2014 | Albertsen et al. | |
| 2016/0145640 | A1* | 5/2016 | Lai | .......... A01H 1/045 435/320.1 |
| 2019/0338305 | A1 | 11/2019 | Ma et al. | |

FOREIGN PATENT DOCUMENTS

| CN | 102960234 A | 3/2013 |
|---|---|---|
| CN | 102965391 A | 3/2013 |
| CN | 110178721 A | 8/2019 |

OTHER PUBLICATIONS

Bradley et al. The Plant Journal (1998):13(3), 381-392.*
Chen et al. The Plant Cell (1996), vol. 8, pp. 971-983.*
Rock et al. American Journal of Botany (1999) 86(12):1796-1800.*
Sawers et al. Plant Molecular Biology (2006) 60:95-106.*
Cigan et al. Sex Plant Reprod (2001) 14:135-142.*
International Search Report from PCT/CN2020/095082 dated Sep. 10, 2020.
Written Opinion from PCT/CN2020/095082 dated Sep. 10, 2020.

* cited by examiner

*Primary Examiner* — Medina A Ibrahim
(74) *Attorney, Agent, or Firm* — Calfee, Halter & Griswold LLP

(57) ABSTRACT

Provided area male sterility maintainer line plant, a method for producing the male sterility maintainer line plant, and use of said plant for propagating a male sterility line plant and the male sterility maintainer line plant. In addition, a nucleic acid molecule, a vector, and a host cell for producing the male sterility maintainer line plant are provided.

15 Claims, 4 Drawing Sheets

Specification includes a Sequence Listing.

SEQUENCE LISTING

```
<160> NUMBER OF SEQ ID NOS: 18

<210> SEQ ID NO 1
<211> LENGTH: 1239
<212> TYPE: DNA
<213> ORGANISM: artificial
<220> FEATURE:
<223> OTHER INFORMATION: Ms45 gene

<400> SEQUENCE: 1
atggagaaga ggaacctgca gtggcggcga gggcgtgatg gcatcgtgca gtaccctcac        60
ctcttcttcg cggccctggc gctggccctc ctagtcgcgg acccgttcgg cctcagtccg       120
ctggccgagg tcgactaccg gccggtgaag cacgagctcg cgccgtacgg ggaggtcatg       180
ggcagctggc ccagagacaa tgccagccgg ctcaggcgcg ggaggctgga gttcgtcggc       240
gaggtgttcg ggccggagtc tatcgagttc gatctccagg gccgcgggcc gtacgccggc       300
ctcgccgacg gccgcgtcgt gcggtggatg ggcgaggagg ccgggtggga gacgttcgcc       360
gtcatgaatc ctgactggtc agaagaagtc tgtgccaatg gagtgaactc aacgacgagg       420
aagcagcacg agaaggagga gttctgcggc cggccgctcg gcctgaggtt ccacggggag       480
accggcgagc tctacgtcgc cgacgcgtac tacggtctca tggtcgttgg ccagagcggc       540
ggcgtggcgt cctccgtcgc gagggaagcc gacggggacc ccatccggtt cgcgaacgac       600
ctcgatgtgc acaggaatgg atccgtattc ttcactgaca cgagcatgag atacagcaga       660
aaggaccatc tgaacatcct gttagaagga gaaggcaccg ggaggctgct caggtatgat       720
ccagaaacaa gcggtgtcca tgtcgtgctc aagggggctgg tgttcccaaa cggcgtgcag       780
atctcagagg accatcagtt tcttctcttc tccgagacaa caaactgcag gataatgagg       840
tactggctgg aaggcccaag agcgggcgag gtagaagtgt tcgcgaacct gccgggcttc       900
cccgacaacg tgcgctccaa cggcaggggc cagttctggg tggcgatcga ctgctgccgg       960
acgccggcgc aggaggtgtt cgccaagagg ccgtggctcc ggaccctgta cttcaagttc      1020
ccgctgtcgc tcaaggtgct cacttggaag gccgccagga ggatgcacac ggtgctcgcg      1080
ctcctcgacg gcgaagggcg cgtcgtggag gtgctcgagg accggggcca cgaggtgatg      1140
```

```
aagctggtga gcgaggtgcg ggaggtgggc cgcaagctgt ggatcggaac cgtggcgcac    1200
aaccacatcg ccaccatccc ctacccttta gaggactaa                           1239
```

<210> SEQ ID NO 2
<211> LENGTH: 412
<212> TYPE: PRT
<213> ORGANISM: artificial
<220> FEATURE:
<223> OTHER INFORMATION: Ms45 protein

<400> SEQUENCE: 2

```
Met Glu Lys Arg Asn Leu Gln Trp Arg Arg Gly Arg Asp Gly Ile Val
1               5                   10                  15

Gln Tyr Pro His Leu Phe Phe Ala Ala Leu Ala Leu Ala Leu Leu Val
            20                  25                  30

Ala Asp Pro Phe Gly Leu Ser Pro Leu Ala Glu Val Asp Tyr Arg Pro
        35                  40                  45

Val Lys His Glu Leu Ala Pro Tyr Gly Glu Val Met Gly Ser Trp Pro
    50                  55                  60

Arg Asp Asn Ala Ser Arg Leu Arg Arg Gly Arg Leu Glu Phe Val Gly
65                  70                  75                  80

Glu Val Phe Gly Pro Glu Ser Ile Glu Phe Asp Leu Gln Gly Arg Gly
                85                  90                  95

Pro Tyr Ala Gly Leu Ala Asp Gly Arg Val Val Arg Trp Met Gly Glu
            100                 105                 110

Glu Ala Gly Trp Glu Thr Phe Ala Val Met Asn Pro Asp Trp Ser Glu
        115                 120                 125

Glu Val Cys Ala Asn Gly Val Asn Ser Thr Thr Arg Lys Gln His Glu
    130                 135                 140

Lys Glu Glu Phe Cys Gly Arg Pro Leu Gly Leu Arg Phe His Gly Glu
145                 150                 155                 160

Thr Gly Glu Leu Tyr Val Ala Asp Ala Tyr Tyr Gly Leu Met Val Val
                165                 170                 175

Gly Gln Ser Gly Gly Val Ala Ser Ser Val Ala Arg Glu Ala Asp Gly
            180                 185                 190

Asp Pro Ile Arg Phe Ala Asn Asp Leu Asp Val His Arg Asn Gly Ser
        195                 200                 205

Val Phe Phe Thr Asp Thr Ser Met Arg Tyr Ser Arg Lys Asp His Leu
    210                 215                 220

Asn Ile Leu Leu Glu Gly Glu Gly Thr Gly Arg Leu Leu Arg Tyr Asp
225                 230                 235                 240

Pro Glu Thr Ser Gly Val His Val Val Leu Lys Gly Leu Val Phe Pro
                245                 250                 255

Asn Gly Val Gln Ile Ser Glu Asp His Gln Phe Leu Leu Phe Ser Glu
            260                 265                 270

Thr Thr Asn Cys Arg Ile Met Arg Tyr Trp Leu Glu Gly Pro Arg Ala
        275                 280                 285

Gly Glu Val Glu Val Phe Ala Asn Leu Pro Gly Phe Pro Asp Asn Val
    290                 295                 300

Arg Ser Asn Gly Arg Gly Gln Phe Trp Val Ala Ile Asp Cys Cys Arg
305                 310                 315                 320

Thr Pro Ala Gln Glu Val Phe Ala Lys Arg Pro Trp Leu Arg Thr Leu
                325                 330                 335
```

```
Tyr Phe Lys Phe Pro Leu Ser Leu Lys Val Leu Thr Trp Lys Ala Ala
            340                 345                 350

Arg Arg Met His Thr Val Leu Ala Leu Leu Asp Gly Glu Gly Arg Val
        355                 360                 365

Val Glu Val Leu Glu Asp Arg Gly His Glu Val Met Lys Leu Val Ser
    370                 375                 380

Glu Val Arg Glu Val Gly Arg Lys Leu Trp Ile Gly Thr Val Ala His
385                 390                 395                 400

Asn His Ile Ala Thr Ile Pro Tyr Pro Leu Glu Asp
                405                 410

<210> SEQ ID NO 3
<211> LENGTH: 3504
<212> TYPE: DNA
<213> ORGANISM: artificial
<220> FEATURE:
<223> OTHER INFORMATION: Promoter and coding region of Ms45 gene

<400> SEQUENCE: 3
tgctgagttc tccttgggtt atccatggtg tctctatgaa aaagatgagt acaatgtgtc      60
tatatccgtt ttcttagggt cccttcttct gccttattac tgactgaatc ggggttacaa     120
aaaaacttcc acgggtgcat gatctccatg ttccacttct cccacctcgc gttgcacatt     180
tcttggatgt cggtggttcc catctgaccg aggcccatca gacacctttc gggacaccca     240
tcaagggcct ttcggatggc ccacgagacg tatcgggtcg tggtgatcca ggggatatat     300
gtcccccaca atcgtcacct atattattat tctttagata ttatttaatt tttggaaaaa     360
taacaaactt atacttttgt gtagggcctc agcatagatt ttcgcttagg gcccagaaat     420
gcgaggacca gccatgtcta gtgtccacta ttggcactac ccagaacaag atttaaaaaa     480
ataaccaaag taactaatcc actcgaaagc tatcatgtaa tgtttaaaga acatctatt     540 aaaaccacga tcctcttaaa aaacaagcat atttcgaaag agacaaatta tgttacagtt     600
tacaaacatc taagagcgac aaattatatc gaaaggtaag ctatgacgtt cagatttttc     660 ttttcattc ttgttatttt gttattgttt ttatatacat tttcttctct tacaatagag     720
tgattttctt ccgattttat aaaatgacta taaagtcatt tttatataag agcacgcatg     780
tcgtagattc tcgttcaaaa atctttctga tttttttaag agctagtttg caaccctgt     840 ttctttcaaa gaattttgat tttttcaaaa aaaattagtt tattttctct ttataaaata     900
gaaaacactt agaaaaatag agttgccaga ctagccctag aatgttttcc caataaatta     960
caatcactgt gtataattat ttggccagcc ccataaatta tttaaaccga aactgaaatc    1020
gagcgaaacc aaatctgagc tatttctcta gattagtaaa aagggagaga gagaggaaga    1080
aatcagtttt aagtcattgt ccctgagatg tgcggtttgg caacgatagc caccgtaatc    1140
atagctcata ggtgcctacg tcaggttcgg cagctctcgt gtcatctcac atggcatact    1200
acatgcttgt tcaaccgttc gtcttgttcc atcgtccaag ccttgcctat tctgaaccaa    1260
gaggatacct actcccaaac aatccatctt actcatgcaa cttccatgca aacacgcaca    1320
tatgtttcct gaaccaatcc attaaagatc acaacagcta gcgttctccc gctagcttcc    1380
ctctctcctc tgccgatctt tttcgtccac cagcatggag aagaggaacc tgcagtggcg    1440
gcgagggcgt gatggcatcg tgcagtaccc tcacctcttc ttcgcggccc tggcgctggc    1500
cctcctagtc gcggacccgt tcggcctcag tccgctggcc gaggtcgact accggccggt    1560
gaagcacgag ctcgcgccgt acggggaggt catgggcagc tggcccagag acaatgccag    1620
```

```
ccggctcagg cgcgggaggc tggagttcgt cggcgaggtg ttcgggccgg agtctatcga   1680
gttcgatctc cagggccgcg ggccgtacgc cggcctcgcc gacggccgcg tcgtgcggtg   1740
gatgggcgag gaggccgggt gggagacgtt cgccgtcatg aatcctgact ggtaagtgct   1800
cgatatcgct ccggcgtcca ctcgttacat gctataatat agtagtacta agatattttg   1860
atctgatttt ttgcattctt gggagaaacg tcatgcaaaa tttgttgttt cttggcaaag   1920
gtcagaagaa gtctgtgcca atggagtgaa ctcaacgacg aggaagcagc acgagaagga   1980
ggagttctgc ggccggccgc tcggcctgag gttccacggg gagaccggcg agctctacgt   2040
cgccgacgcg tactacggtc tcatggtcgt tggccgagc ggcggcgtgg cgtcctccgt   2100
cgcgagggaa gccgacgggg accccatccg gttcgcgaac gacctcgatg tgcacaggaa   2160
tggatccgta ttcttcactg acacgagcat gagatacagc agaaagtgag caaagcgacg   2220
taacaatccg gcttctcatt ttcaaacgcc tctgtattct ctgctgaaag agtagctcac   2280
cagacaagag ctgaatttgc agggaccatc tgaacatcct gttagaagga gaaggcaccg   2340
ggaggctgct caggtatgat ccagaaacaa gcggtgtcca tgtcgtgctc aaggggctgg   2400
tgttcccaaa cggcgtgcag atctcagagg accatcagtt tcttctcttc tccgagacaa   2460
caaactgcag gtaacaaaaa tactatctga cgatgctcat gattctaccg tatccatagt   2520
catgaacaca aaccacacga atctggcctt gaccaggata tgaggtact ggctggaagg    2580 cccaagagcg ggcgaggtag aagtgttcgc gaacctgccg ggcttccccg acaacgtgcg   2640
ctccaacggc aggggccagt tctgggtggc gatcgactgc tgccggacgc cggcgcagga   2700
ggtgttcgcc aagaggccgt ggctccggac cctgtacttc aagttcccgc tgtcgctcaa   2760
ggtgctcact tggaaggccg ccaggaggat gcacacggtg ctcgcgctcc tcgacggcga   2820
agggcgcgtc gtggaggtgc tcgaggaccg gggccacgag gtgatgaagc tggtgagcga   2880
ggtgcgggag gtgggccgca agctgtggat cggaaccgtg gcgcacaacc acatcgccac   2940
catcccctac cctttagagg actaaccatg atctatgctg tttcaatgcc tcctaatctg   3000
tgtacgtcta taaatgtcta atgcagtcac tggttgtaat cttgtttgtg tttggcaaat   3060
tggcataata atgacagat tcaatgggca ttggtgctgt agtcgcatca cactaattga     3120
atgggatcat gttgagctct cacttttgcta caattttgctc cagcttgtac ggttgtaccc   3180
tcttgctcgt ctatagtaag ggccatctaa aaaaaactca aattagatct gcaatacaag   3240
tatgattggg ccgaatttgg attgtcacgg gtccgcgacc gcgaattggg ctcggtttga   3300
tttagccgac atagtagtga ccgacccgag ccggcggcga gccaaaccga gcggacgccg   3360
ccatggatcg cgagtggggc tccaagcccg gcagcggcgg cgccgcctcc gcgcagaatg   3420
aggccatcga ccgcgggag cgcctccgcc gcctggccct cgagaccatc gacctcgcca    3480
aggaccccta tttcatgcgc aacc                                         3504
```

<210> SEQ ID NO 4
<211> LENGTH: 1833
<212> TYPE: DNA
<213> ORGANISM: artificial
<220> FEATURE:
<223> OTHER INFORMATION: Lc gene

<400> SEQUENCE: 4

```
atggcgcttt cagcttcccg agttcagcag gcggaagaac tgctgcaacg acctgctgag    60
aggcagctga tgaggagcca gcttgctgca gccgccagga gcatcaactg gagctacgcc   120
```

```
ctcttctggt ccatttcaga cactcaacca ggggtgctga cgtggacgga cgggttctac    180
aacggcgagg tgaagacgcg gaagatctcc aactccgtgg agctgacatc cgaccagctc    240
gtcatgcaga ggagcgacca gctccgggag ctctacgagg ccctcctgtc gggcgagggc    300
gaccgccgcg ctgcgcctgc gcggccggcc ggctctctgt cgccggagga cctcggcgac    360
accgagtggt actacgtggt ctccatgacc tacgccttcc ggccaggcca agggttgccc    420
ggcaggagtt tcgcgagcga cgagcatgtc tggctgtgca acgcgcacct cgccggcagc    480
aaagccttcc cccgcgcgct cctggccaag agcgcgtcca ttcagtcaat cctctgcatc    540
ccggttatgg gcggcgtgct tgagcttggt acaactgaca cggtgccgga ggccccggac    600
ttggtcagcc gagcaaccgc ggctttctgg agccgcagt gcccgagctc cagcccgtca    660
ggacgagcaa cgagaccgg cgaggccgca gcagacgacg gcacgtttgc gttcgaggaa    720
ctcgaccaca ataatggcat ggacgacata gaggcgatga ccgccgccgg gggacacggg    780
caggaggagg agctaagact aagagaagcc gaggccctgt cagacgacgc aagcctggag    840
cacatcacca aggagatcga ggagttctac agcctctgcg acgaaatgga cctgcaggcg    900
ctaccactac cgctagagga cggctggacc gtggacgcgt ccaatttcga ggtccctgc    960 tcttccccgc agccagcgcc gcctccggtg acagggcta ccgctaacgt cgccgccgac    1020
gcctcaaggg cacccgtcta cggctctcgc gcgacgagtt tcatggcttg acgaggtcc    1080 tcgcagcagt cgtcgtgctc cgacgacgcg gcgcccgcag cagtagtgcc ggccatcgag    1140
gagccgcaga gattgctgaa gaaagtggtg gccggcggcg gtgcttggga gagctgtggc    1200
ggcgcgacgg gagcagcaca ggaaatgagt ggcactggca ccaagaacca cgtcatgtcg    1260
gagcgaaagc gacgagagaa gctcaacgag atgttcctcg tcctcaagtc actgcttccg    1320
tccattcaca gggtgaacaa agcgtcgatc ctcgccgaaa cgatagccta cctcaaggag    1380
cttcagagaa gggtgcaaga gctggagtcc agtagggaac ctgcgtcgcg cccatccgaa    1440
acgacgacaa ggctaataac aaggcccctcc cgtggcaata atgagagtgt gaggaaggag    1500
gtctgcgcgg gctccaagag gaagagccca gagctcggca gagacgacgt ggagcgcccc    1560
ccggtcctca ccatggacgc cggcaccagc aacgtcaccg tcaccgtctc ggacaaggac    1620
gtgctcctgg aggtgcagtg ccggtgggag gagctcctga tgacgcgagt gttcgacgcc    1680
atcaagagcc tccatttgga cgtcctctcg gttcaggctt cagcgccaga tggcttcatg    1740
gggcttaaga tacgagctca gtttgctggc tccggtgccg tcgtgccctg gatgatcagc    1800
gaggctcttc gcaaagctat agggaagcgg tga                                1833
```

<210> SEQ ID NO 5
<211> LENGTH: 610
<212> TYPE: PRT
<213> ORGANISM: artificial
<220> FEATURE:
<223> OTHER INFORMATION: Lc protein

<400> SEQUENCE: 5

```
Met Ala Leu Ser Ala Ser Arg Val Gln Gln Ala Glu Glu Leu Leu Gln
1               5                   10                  15

Arg Pro Ala Glu Arg Gln Leu Met Arg Ser Gln Leu Ala Ala Ala
            20                  25                  30

Arg Ser Ile Asn Trp Ser Tyr Ala Leu Phe Trp Ser Ile Ser Asp Thr
        35                  40                  45

Gln Pro Gly Val Leu Thr Trp Thr Asp Gly Phe Tyr Asn Gly Glu Val
    50                  55                  60
```

```
Lys Thr Arg Lys Ile Ser Asn Ser Val Glu Leu Thr Ser Asp Gln Leu
 65                  70                  75                  80

Val Met Gln Arg Ser Asp Gln Leu Arg Glu Leu Tyr Glu Ala Leu Leu
                 85                  90                  95

Ser Gly Glu Gly Asp Arg Arg Ala Ala Pro Ala Arg Pro Ala Gly Ser
            100                 105                 110

Leu Ser Pro Glu Asp Leu Gly Asp Thr Glu Trp Tyr Tyr Val Val Ser
        115                 120                 125

Met Thr Tyr Ala Phe Arg Pro Gly Gln Gly Leu Pro Gly Arg Ser Phe
    130                 135                 140

Ala Ser Asp Glu His Val Trp Leu Cys Asn Ala His Leu Ala Gly Ser
145                 150                 155                 160

Lys Ala Phe Pro Arg Ala Leu Leu Ala Lys Ser Ala Ser Ile Gln Ser
                165                 170                 175

Ile Leu Cys Ile Pro Val Met Gly Gly Val Leu Glu Leu Gly Thr Thr
            180                 185                 190

Asp Thr Val Pro Glu Ala Pro Asp Leu Val Ser Arg Ala Thr Ala Ala
        195                 200                 205

Phe Trp Glu Pro Gln Cys Pro Ser Ser Pro Ser Gly Arg Ala Asn
    210                 215                 220

Glu Thr Gly Glu Ala Ala Ala Asp Asp Gly Thr Phe Ala Phe Glu Glu
225                 230                 235                 240

Leu Asp His Asn Asn Gly Met Asp Asp Ile Glu Ala Met Thr Ala Ala
                245                 250                 255

Gly Gly His Gly Gln Glu Glu Glu Leu Arg Leu Arg Glu Ala Glu Ala
            260                 265                 270

Leu Ser Asp Asp Ala Ser Leu Glu His Ile Thr Lys Glu Ile Glu Glu
        275                 280                 285

Phe Tyr Ser Leu Cys Asp Glu Met Asp Leu Gln Ala Leu Pro Leu Pro
    290                 295                 300

Leu Glu Asp Gly Trp Thr Val Asp Ala Ser Asn Phe Glu Val Pro Cys
305                 310                 315                 320

Ser Ser Pro Gln Pro Ala Pro Pro Val Asp Arg Ala Thr Ala Asn
                325                 330                 335

Val Ala Ala Asp Ala Ser Arg Ala Pro Val Tyr Gly Ser Arg Ala Thr
            340                 345                 350

Ser Phe Met Ala Trp Thr Arg Ser Gln Gln Ser Ser Cys Ser Asp
        355                 360                 365

Asp Ala Ala Pro Ala Ala Val Val Pro Ala Ile Glu Glu Pro Gln Arg
    370                 375                 380

Leu Leu Lys Lys Val Val Ala Gly Gly Ala Trp Glu Ser Cys Gly
385                 390                 395                 400

Gly Ala Thr Gly Ala Ala Gln Glu Met Ser Gly Thr Gly Thr Lys Asn
                405                 410                 415

His Val Met Ser Glu Arg Lys Arg Arg Glu Lys Leu Asn Glu Met Phe
            420                 425                 430

Leu Val Leu Lys Ser Leu Leu Pro Ser Ile His Arg Val Asn Lys Ala
        435                 440                 445

Ser Ile Leu Ala Glu Thr Ile Ala Tyr Leu Lys Glu Leu Gln Arg Arg
    450                 455                 460

Val Gln Glu Leu Glu Ser Ser Arg Glu Pro Ala Ser Arg Pro Ser Glu
465                 470                 475                 480
```

Thr Thr Thr Arg Leu Ile Thr Arg Pro Ser Arg Gly Asn Asn Glu Ser
            485                 490                 495

Val Arg Lys Glu Val Cys Ala Gly Ser Lys Arg Lys Ser Pro Glu Leu
        500                 505                 510

Gly Arg Asp Asp Val Glu Arg Pro Pro Val Leu Thr Met Asp Ala Gly
            515                 520                 525

Thr Ser Asn Val Thr Val Thr Val Ser Asp Lys Asp Val Leu Leu Glu
        530                 535                 540

Val Gln Cys Arg Trp Glu Glu Leu Leu Met Thr Arg Val Phe Asp Ala
545                 550                 555                 560

Ile Lys Ser Leu His Leu Asp Val Leu Ser Val Gln Ala Ser Ala Pro
            565                 570                 575

Asp Gly Phe Met Gly Leu Lys Ile Arg Ala Gln Phe Ala Gly Ser Gly
            580                 585                 590

Ala Val Val Pro Trp Met Ile Ser Glu Ala Leu Arg Lys Ala Ile Gly
            595                 600                 605

Lys Arg
    610

<210> SEQ ID NO 6
<211> LENGTH: 4464
<212> TYPE: DNA
<213> ORGANISM: artificial
<220> FEATURE:
<223> OTHER INFORMATION: Oy1 gene

<400> SEQUENCE: 6
gaaaaaagtg ttaagaaatc aacatgttgt catatcgggg ctcacaacgt atcattctcc      60
attgacagac catgaagaaa tgagcacagg aaactttaag attcaatgcc ttcgatgaat     120
aggcattaga aaaaaaagt tggaagataa aactagctaa ctgaaacatg tgtgaagata     180
ctgaaggctc tgaaattgat aaacctacat tttccaggga caaaaacatg agtaaatgga     240
gcatggcatg gcagctttaa tctgtatgca caaaacattc aagtgattaa gcagtaaata     300
aaggttgcta acaaaattag ctcagaaagct agtacaattg agcataaaag caatagctaa     360
cttccataga taaaagatag gctagaacca gaaatataat cttattaaca cattaagtca     420
tagtcctaat aatgagagaa atatttgcca aattctgaaa tgcaacaaac agacatgtcg     480
tttcactgat acaaaagtac tgagacggtg agaccccaag ctaattttgt agctacctcg     540
agatttcaaa aacctgttcg ccttcctgtt atcacatgaa atcatgctaa attacacttc     600
acttactgta cgcaacactt aggagctgtt tggttccttt agtgactaaa ctttagtccc     660
tagaaatcct atttaaaata cctattttag tcacccattg gtattttagg aactaaaagt     720
gactaaattt tagtcacccc atttagtatt ttagggacta aaagtgaaaa gtttagtagg     780
tgggtaccaa acacctccta aagtttagtc actaaagttt aggagggtga ctaaaggaac     840
caaacacccc cttagtccct agaaatccta tttgaaagac atattttaat cactttgttt     900
aggcccgttt ggttccttta gtcaattgac taaacttaag tgattaaagt ttagtcacta     960
aagtacacag ttttgttcca gtgactaaac ctaactaaaa agcattaatt tagtgcgaat    1020
aatgactgca ttacccctat taactagtgg atgtctgttg cactaagaaa gaggagaagt    1080
caaatgaggt aaaaatccta ctttagtcca ttttagtcac ccccttggtg actaaagaac    1140
ttaagtttag tcaccccact ttagtcacca tgtttgcttc tttagggact aaggatgcgt    1200
ttggttgcgg gacagctggt gacaggcagg acagagatgt ccccaggcgt cctctctcgt    1260

```
ccctctaatt ttgagggaca actagggaca acactgggat aatcctgtcc caaccsctga    1320
ccctgaacca aacaacctta tttaagggac atcctatctc atcccgttct gtcattacaa    1380
ccaaacgcat cctaaaagtg gtgaaagggc ctctaacgta atggttaagg cttccgagta    1440
gcacctccag gttccgggtt cgatcctcct cggggacgaa ttttagactt ggttaaaaaa    1500
atcccctcgc tgtgccccac ccgctaccgg gttacgtcct acgcgtcacc ctccgactgg    1560
accgttgcag agtgagcggt gatggcccgc tagtgatagg gggccaaggc aggggcgaag    1620
ccagcatttg agattgagag ggacaaatta gattgagggg ggctgttaag aggtatttta    1680
cattatttat atggtgatta gctaaaaaaa ttaatagctt ctatggaatt tgtagaagat    1740
taggggggac attgcccccc tgtgcccctc cctagaatcg cccctgggcc aaggttcggg    1800
gattttctcg gtcaggacca tgtttcggcc tcttcttaat ataataccag gagggctgtc    1860
tttccctccc cggtcgagtt tttagggact aaaagtggct attttagcca ccccaaacca    1920
aatgaggcct tagtatttta gtgactcgat aaagtttagg agatgagaac caaacaccac    1980
cttagcttca tatcaattaa ttgcctcttt catcaacaag aaacaatgcg tattttaaaa    2040
aaaatttgcc aacatgccaa cccttatatg gacacttaca agcaggcact agataccctta   2100 aacttttcgc aaggcaaatg tactccatcc tctaccacta catgtccctc aactgtctca    2160
aacaaccaaa tattggtaca aagattgcac aaggtcaata ctatggctta aaatacctag    2220
agattcaaac tgatgcacaa gataataatt tagcataata ctcccttcgt ctcaaataat    2280
agtcgtttta gctctagatt tttatgtcca tattcatatg aatgattatg aacctaaaca    2340
tatatataac ccatacatta attattgtat gcatacagta aaatggtaaa acgaatttta   2400
atttgggacc gaggaaatac ttccgaagtt atgctctaat gcagccaaat gctacaacac    2460
tgatttacaa ggaagactga aatgcaaaga gcattatgat gctcataaca tgcattccaa    2520
atggaaggaa tggatcctac attattatga tgctagatgc acaaaattga taccaattca    2580
agctccagat attattaaac agcagaacat tatgaaagta acagaacaag agggttcccg    2640
ccaaaaattg tgactaagga acatttacct caagaacaat ctagctaaag acttcataaa    2700
acttctcaat gacaagtaaa cccgagtcaa tggattcaag cggatccttg cggagccgat    2760
gcctcaagca gtttggaatg acagtagcaa tgtcctccac ggtgacgctg tcccttcctt    2820
tcaacgcagc cagcgccttg gcagcccctgt tagtcacaat gtcacctctg agtccatcaa   2880
cgttcaactc agagcacacc ttggatatct tgacacggag gtcatggtca atctgcacag    2940
cgccaaggtt actccgtgca gatgatatct gctgctggag cttctcctgc tcgtcatgat    3000
acgactcacg gaacgtcttc ggatccctgt cgaaacgagc cctctcctcc acgatcttca    3060
ccctgagctc ggcgtccctg acggtaccaa cctgcgcgtg catcccgaac cggtccagca    3120
gctggggcct gagctcccct tcctccgggt taccagagcc gatgaggatg aagcgagcag    3180
ggtgggatat ggagataccc ttcctctcca ccgtgttcca ccccgacgca gcggaatcca    3240
gcagcacgtc gacgaggtgg tcgtccagca ggttgacctc gtcgacgtac agtatgcccc    3300
tgttggcctt ggcgagcagg ccgggctcga acgccttgac gccctcggtg agcgccttct    3360
cgatgtcaat ggtgccgcag acgcggtcct cggtggcgcc gagggcagg tcgaccatgg    3420 tgatcttggc ggtggtgacg gggaggccgg tgtcccctg caggacccgc tggcggacct    3480
cggggcccat gacctcgggg tcgtccgggt cggagttgaa gggtcgccg acgacgacg    3540 ggatgtccgg gagcaggtcg acgagggagc ggacggtggt ggacttcccc gtgcccctgt    3600
cgcccatgat catgacgccg ccgatcttgg ggtcgatgac gttgagcagc aggcagagct    3660
```

-continued

```
tcatctcgtc ctgccccacg atggccgcga acgggtacac ggggcgctgg gtctccttcg      3720
cggccgacgc cgtcgcctcc tgcgcggaag cagaagcagg catcgaaaat gcggggttgc      3780
ggaggaagga ttaccgaccg gttcctgcgg gctgcgggat tggagaacgg gggcgtacct      3840
gttcggcggc ggtgggagcg gcgacattgc agacggtgaa tcggccgcgg cggaagtcca      3900
gtcccttcct ggatggttga atgcgccctg cgagtgtacc ggggggcgg taagggggg        3960 tgttggattc ggcgctcgct gatgagcgag ctgggaaaca gagtgagtag ggggagggaa      4020
atgtgagatg acggttacct gaggaagctg aagcggcgag gaagagtggg cgggaggtgg     4080
agcccgggag gagggccctc gcggcggaag tgggggagaa ggtggaagcc atgacgggga     4140
ggagaggaag aagggggcatg gaggtttgtg tggaaggagc gggggaggag gggataggg    4200 ataagccggg ggaggggggac ggggcagcga tctcggaggg atgctgcgat tggaggctgc   4260
caacttctgg attgaccggc cccgcttggc agtcggcagc aagcaatcgt tgttgatggt     4320
aacggcttga tggagttgac gatgctatgg cgctgttgcc actgatttta gggtacgcga      4380
aacggctcaa aatgatagtt tgatactatg gcgctgtgcc caacatgctt gccttcgtcc     4440
tcagcatgac agcatctatc tagt                                             4464
```

<210> SEQ ID NO 7
<211> LENGTH: 459
<212> TYPE: PRT
<213> ORGANISM: artificial
<220> FEATURE:
<223> OTHER INFORMATION: Oy1 protein

<400> SEQUENCE: 7

```
Met Pro Leu Leu Pro Leu Leu Pro Val Met Ala Ser Thr Phe Ser Pro
1               5                   10                  15

Thr Ser Ala Ala Arg Ala Leu Leu Pro Gly Ser Thr Ser Arg Pro Leu
            20                  25                  30

Phe Leu Ala Ala Ser Ala Ser Ser Gly Asn Arg His Leu Thr Phe Pro
        35                  40                  45

Ser Pro Tyr Ser Leu Cys Phe Pro Ala Arg Ser Ala Ser Ala Glu
    50                  55                  60

Ser Asn Thr Pro Pro Tyr Arg Pro Pro Gly Thr Leu Ala Gly Arg Ile
65                  70                  75                  80

Gln Pro Ser Arg Lys Gly Leu Asp Phe Arg Arg Gly Arg Phe Thr Val
                85                  90                  95

Cys Asn Val Ala Ala Pro Thr Ala Ala Glu Gln Glu Ala Thr Ala Ser
            100                 105                 110

Ala Ala Lys Glu Thr Gln Arg Pro Val Tyr Pro Phe Ala Ala Ile Val
        115                 120                 125

Gly Gln Asp Glu Met Lys Leu Cys Leu Leu Asn Val Ile Asp Pro
    130                 135                 140

Lys Ile Gly Gly Val Met Ile Met Gly Asp Arg Gly Thr Gly Lys Ser
145                 150                 155                 160

Thr Thr Val Arg Ser Leu Val Asp Leu Leu Pro Asp Ile Arg Val Val
                165                 170                 175

Val Gly Asp Pro Phe Asn Ser Asp Pro Asp Pro Glu Val Met Gly
            180                 185                 190

Pro Glu Val Arg Gln Arg Val Leu Gln Gly Asp Thr Gly Leu Pro Val
        195                 200                 205
```

```
Thr Thr Ala Lys Ile Thr Met Val Asp Leu Pro Leu Gly Ala Thr Glu
    210                 215                 220
Asp Arg Val Cys Gly Thr Ile Asp Ile Glu Lys Ala Leu Thr Glu Gly
225                 230                 235                 240
Val Lys Ala Phe Glu Pro Gly Leu Leu Ala Lys Ala Asn Arg Gly Ile
                245                 250                 255
Leu Tyr Val Asp Glu Val Asn Leu Leu Asp Asp His Leu Val Asp Val
            260                 265                 270
Leu Leu Asp Ser Ala Ala Ser Gly Trp Asn Thr Val Glu Arg Lys Gly
        275                 280                 285
Ile Ser Ile Ser His Pro Ala Arg Phe Ile Leu Ile Gly Ser Gly Asn
    290                 295                 300
Pro Glu Glu Gly Glu Leu Arg Pro Gln Leu Leu Asp Arg Phe Gly Met
305                 310                 315                 320
His Ala Gln Val Gly Thr Val Arg Asp Ala Glu Leu Arg Val Lys Ile
                325                 330                 335
Val Glu Glu Arg Ala Arg Phe Asp Arg Asp Pro Lys Thr Phe Arg Glu
            340                 345                 350
Ser Tyr His Asp Glu Gln Glu Lys Leu Gln Gln Ile Ser Ser Ala
        355                 360                 365
Arg Ser Asn Leu Gly Ala Val Gln Ile Asp His Asp Leu Arg Val Lys
    370                 375                 380
Ile Ser Lys Val Cys Ser Glu Leu Asn Val Asp Gly Leu Arg Gly Asp
385                 390                 395                 400
Ile Val Thr Asn Arg Ala Ala Lys Ala Leu Ala Leu Lys Gly Arg
                405                 410                 415
Asp Ser Val Thr Val Glu Asp Ile Ala Thr Val Ile Pro Asn Cys Leu
            420                 425                 430
Arg His Arg Leu Arg Lys Asp Pro Leu Glu Ser Ile Asp Ser Gly Leu
        435                 440                 445
Leu Val Ile Glu Lys Phe Tyr Glu Val Phe Ser
    450                 455

<210> SEQ ID NO 8
<211> LENGTH: 3529
<212> TYPE: DNA
<213> ORGANISM: artificial
<220> FEATURE:
<223> OTHER INFORMATION: Wi2 gene

<400> SEQUENCE: 8
gcccccggcc tcctcccgcc tcccagatct cgctcggcgc cagttgcctc gcagtttgga      60
tcatctcata cctcgtaagt cgtaaggatt tctgaactac gctcataacc gagttttcaa     120
tctgtgttgc ggtctcgcat tatttctgat ctgttagctt gttttttttt ctgttgccaa     180
attctgggtt gttcccgcga tgtaaccgga atgcgattg  gatccgctga tttgccactt     240
aggaataggg atggattcgg atatttattc ggatgtcatt ttttttttggt cttctttctt     300 cgattgtgaa caattaacat ataaaatttg atatgtaaat ttatattctt gttttttagca    360 ttgagactat taatcttcac aaaaaataaa cattaaatcc attctatatc tttttaaata     420
attcatataa aattcggatg tctattcgaa tacggattcg gatgttttt cacctttttt      480 gttgtaagga gaaataatg tacataaaaa attatacaaa aatttattta aatacttcag      540
aatattctta ataacattgc cgaaaattaa ctttaaattc tatgtatatc tatgctaaaa     600
```

|  |  |
|---|---|
| tattagattt gtgatacaat tcggatgttt taggaacatc cctacctagg aatgtcctgg | 660 |
| cctctctctc tctctcttga cgaaggttat tcgattggtt ctgtgattct gcgtagttga | 720 |
| gtgggatcca tagtgtttga ttttggggga attcaagtcg tcctttaatt gcgaaatgta | 780 |
| actgttagac cttagagaca gagagctttg tgggtttatt atcataactt agtgcagttt | 840 |
| tgaagtataa gtttcagtac tgaaactaga tccggaagaa catacgtcac cgtttgaacg | 900 |
| gttgggctca tggaattatt tgtaatcatg gggagacatg tttgaagtct gctataatat | 960 |
| tgatgcattt agtacttatc agtaggcgat tcagtggttg atgtgtgtgc aagatgggtt | 1020 |
| tgcaagccca gatcttgtta tggttcgcta tgtgatccga gtacgagttc agtgatgttt | 1080 |
| tagatctgaa actgcagtga caatgtgcgc tcgctctctg gtttagttgc aaatggctag | 1140 |
| aaatacttga tttaatcaac ttgaggagtg actgtgtgct tgttgcagta tctgtagcta | 1200 |
| attcctatgt gcttctcttg tttgtagggc gaatatgagg gagatcctgc acatccaggg | 1260 |
| agggcaatgt ggcaaccaga ttggcgccaa gttctgggag gtggtgtgtg atgagcatgg | 1320 |
| cattgaccct accgggcggt acactggcag ttccgacctt cagttggagc gtgttaatgt | 1380 |
| ctactacaac gaagtctcct gtggacgctt tgttccccgc gctgttctca tggatcttga | 1440 |
| gcctgggaca atggacagtg tccggactgg accctatggg cagatcttcc gccctgacaa | 1500 |
| ctttgtgttc gggcaatctg gtgctggtaa caattgggcc aagggccact acaccgaggg | 1560 |
| tgctgagctc attgactctg ttctggatgt tgtgaggaag gaagctgaga actgtgactg | 1620 |
| cttgcaaggt acttgagctt attgatgata aagctgattg cttcaagttt ttatatttgt | 1680 |
| ttctgctgaa gaaactagag tgagatgttc atgttgaagt atctctacag tttcttacc | 1740 |
| catgcttgtg atttttttt cactacaatg cgatacattg aatccatata gggctgaagc | 1800 |
| tatccatgga actagaactg cgatatcctg ttataatgaa gctgcttttg ctctagaacc | 1860 |
| taagtcattt cactcgttta gttcatgccc tataatatag aatggattat cctaaatgac | 1920 |
| actgatactg attggtcctt gccgactgct tagtattttc acatttgagt atcttttctg | 1980 |
| ctgttgccat gttttgacac atgagcagaa acaaattttc ttacttgcac ttgttgcttg | 2040 |
| aacaattggc ataccaaaat actgtacata aaaaagctgt tcagactgtg attactaaat | 2100 |
| cacctatgcg tgtcatgtac cttggttgcc atctgtactt tgctatgtgt ttttttttcca | 2160 |
| atcacccaag taactaaact taattatcat gcattgaaca ttaactcaat ctatttgttt | 2220 |
| attcaggatt ccaagtatgc cactcccttg gtggtggtac tggatctggt atgggtacgc | 2280 |
| tgttgatctc aaagatcagg gaggagtacc ctgaccgcat gatgctgaca ttctcagttt | 2340 |
| tccccctcacc gaaagtatct gataccgtgg ttgagccata caatgccact ctttctgtcc | 2400 |
| accagttggt tgagaatgct gatgagtgca tggttctcga taacgaagcc ctctatgaca | 2460 |
| tctgcttcag gactcttaag ctgaccaccc ccagctgtaa gcagcctcat tctttcttaa | 2520 |
| tttgatctgc tcagcattgc agatatatgc atgctcgtac tagtgtattt actgtgtata | 2580 |
| gtaacactgt atttgttaat tgctgcagtt ggtgatctga accatttgat ctctgcaacc | 2640 |
| atgagtggag tcacctgctg cctaaggttc cctggtcagc tgaactccga cctcaggaag | 2700 |
| ctggcagtga acctgatccc cttcccccgt ctccacttct tcatggtcgg cttcgcgccg | 2760 |
| ctgacgtccc gtggctccca gcagtaccgg gccctcacag tcctcgagct cacgcagcag | 2820 |
| atgtgggatg ccaagaacat gatgtgtgcc gctgacccte gccatgggcg ttacctcacc | 2880 |
| gcctctgcca tgttccgcgg gaagatgagc accaaggagg tcgacgagca aatgatcaac | 2940 |
| gtccagaaca agaactcgtc ctacttcgtg gagtggatcc ccaacaacgt caagtccagc | 3000 |

-continued

```
gtgtgcgaca tcccgcccag gggcctgtcc atggcgtcca ccttcatcgg caactcgacc    3060
tccatccagg agatgttccg gagggtgagc gagcagttca ctgccatgtt caggaggaag    3120
gctttcttgc actggtacac gggcgagggc atggacgaga tggagttcac cgaggccgag    3180
agcaacatga acgacctcgt gtcggagtac cagcagtacc aggacgcgac tgccgacgag    3240
gaggagtacg aggacgagga ggaggtgcag gccgatgaca tgtgagggga gggctgttat    3300
cgtgtgaagc cttgtggtcc tagggcaagc ggacctcgat gagttcggtg ttcccttcg     3360 tgttgttgcc atctttctac tgctagcgta cccacccteg tggcccattc cgtcgctgtt    3420
gacgcatgta ttttcttgt gctatggaac cttgcttttg gtacggtact accttatgct     3480
gcctgctagt atgcttggcg tttgaggttc ctggcttgaa tttaagcct               3529
```

<210> SEQ ID NO 9
<211> LENGTH: 446
<212> TYPE: PRT
<213> ORGANISM: artificial
<220> FEATURE:
<223> OTHER INFORMATION: Wi2 protein

<400> SEQUENCE: 9

```
Met Arg Glu Ile Leu His Ile Gln Gly Gly Gln Cys Gly Asn Gln Ile
1               5                  10                  15

Gly Ala Lys Phe Trp Glu Val Val Cys Asp Glu His Gly Ile Asp Pro
            20                  25                  30

Thr Gly Arg Tyr Thr Gly Ser Ser Asp Leu Gln Leu Glu Arg Val Asn
        35                  40                  45

Val Tyr Tyr Asn Glu Ala Ser Cys Gly Arg Phe Val Pro Arg Ala Val
    50                  55                  60

Leu Met Asp Leu Glu Pro Gly Thr Met Asp Ser Val Arg Thr Gly Pro
65                  70                  75                  80

Tyr Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Ile Asp Ser Val Leu Asp Val Val Arg Lys Glu Ala Glu Asn Cys Asp
        115                 120                 125

Cys Leu Gln Gly Phe Gln Val Cys His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Met Met Leu Thr Phe Ser Val Phe Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Ala Asp Glu Cys Met Val Leu Asp Asn Glu Ala Leu Tyr
        195                 200                 205

Asp Ile Cys Phe Arg Thr Leu Lys Leu Thr Thr Pro Ser Phe Gly Asp
    210                 215                 220

Leu Asn His Leu Ile Ser Ala Thr Met Ser Gly Val Thr Cys Cys Leu
225                 230                 235                 240

Arg Phe Pro Gly Gln Leu Asn Ser Asp Leu Arg Lys Leu Ala Val Asn
                245                 250                 255

Leu Ile Pro Phe Pro Arg Leu His Phe Phe Met Val Gly Phe Ala Pro
            260                 265                 270
```

```
Leu Thr Ser Arg Gly Ser Gln Gln Tyr Arg Ala Leu Thr Val Leu Glu
        275                 280                 285

Leu Thr Gln Gln Met Trp Asp Ala Lys Asn Met Met Cys Ala Ala Asp
290                 295                 300

Pro Arg His Gly Arg Tyr Leu Thr Ala Ser Ala Met Phe Arg Gly Lys
305                 310                 315                 320

Met Ser Thr Lys Glu Val Asp Glu Gln Met Ile Asn Val Gln Asn Lys
                325                 330                 335

Asn Ser Ser Tyr Phe Val Glu Trp Ile Pro Asn Asn Val Lys Ser Ser
            340                 345                 350

Val Cys Asp Ile Pro Pro Arg Gly Leu Ser Met Ala Ser Thr Phe Ile
        355                 360                 365

Gly Asn Ser Thr Ser Ile Gln Glu Met Phe Arg Arg Val Ser Glu Gln
370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Asp Glu
            420                 425                 430

Glu Glu Tyr Glu Asp Glu Glu Val Gln Ala Asp Asp Met
        435                 440                 445
```

<210> SEQ ID NO 10
<211> LENGTH: 552
<212> TYPE: DNA
<213> ORGANISM: artificial
<220> FEATURE:
<223> OTHER INFORMATION: bar gene

<400> SEQUENCE: 10

| | | | | | |
|---|---|---|---|---|---|
| atgagcccag | aacgacgccc | ggccgacatc | cgccgtgcca | ccgaggcgga | catgccggcg | 60 |
| gtctgcacca | tcgtcaacca | ctacatcgag | acaagcacgg | tcaacttccg | taccgagccg | 120 |
| caggaaccgc | aggagtggac | ggacgacctc | gtccgtctgc | gggagcgcta | tcccctggctc | 180 |
| gtcgccgagg | tggacggcga | ggtcgccggc | atcgcctacg | cgggcccctg | gaaggcacgc | 240 |
| aacgcctacg | actggacggc | cgagtcgacc | gtgtacgtct | ccccccgcca | ccagcggacg | 300 |
| ggactgggct | ccacgctcta | cacccacctg | ctgaagtccc | tggaggcaca | gggcttcaag | 360 |
| agcgtggtcg | ctgtcatcgg | gctgcccaac | gacccgagcg | tgcgcatgca | cgaggcgctc | 420 |
| ggatatgccc | cccgcggcat | gctgcgggcg | gccggcttca | agcacgggaa | ctggcatgac | 480 |
| gtgggtttct | ggcagctgga | cttcagcctg | ccggtaccgc | ccgtccggt | cctgcccgtc | 540 |
| accgagattt | ga | | | | | 552 |

<210> SEQ ID NO 11
<211> LENGTH: 31
<212> TYPE: DNA
<213> ORGANISM: artificial
<220> FEATURE:
<223> OTHER INFORMATION: Ms45F

<400> SEQUENCE: 11
tgaattctgc tgagttctcc ttgggttatc c                                31

<210> SEQ ID NO 12
<211> LENGTH: 28

```
<212> TYPE: DNA
<213> ORGANISM: artificial
<220> FEATURE:
<223> OTHER INFORMATION: Ms45R

<400> SEQUENCE: 12
tcccgggggt tgcgcatgaa atagggt                                      28

<210> SEQ ID NO 13
<211> LENGTH: 19
<212> TYPE: DNA
<213> ORGANISM: artificial
<220> FEATURE:
<223> OTHER INFORMATION: Bar669F

<400> SEQUENCE: 13
tctcggtgac gggcaggac                                               19

<210> SEQ ID NO 14
<211> LENGTH: 23
<212> TYPE: DNA
<213> ORGANISM: artificial
<220> FEATURE:
<223> OTHER INFORMATION: Bar669R

<400> SEQUENCE: 14
tgacgcacaa tcccactatc ctt                                          23

<210> SEQ ID NO 15
<211> LENGTH: 1319
<212> TYPE: DNA
<213> ORGANISM: artificial
<220> FEATURE:
<223> OTHER INFORMATION: Ms45 promoter sequence

<400> SEQUENCE: 15
```

| | | | | | |
|---|---|---|---|---|---|
| tgctgagttc | tccttgggtt | atccatggtg | tctctatgaa | aaagatgagt | acaatgtgtc | 60 |
| tatatccgtt | ttcttagggt | cccttcttct | gccttattac | tgactgaatc | ggggttacaa | 120 |
| aaaacttcca | cgggtgcatg | atctccatgt | tccacttctc | ccacctcgcg | ttgcacattt | 180 |
| cttggatgtc | ggtggttccc | atctgaccga | ggcccatcag | acacctttcg | ggacacccat | 240 |
| caagggcctt | tcggatggcc | cacgagacgt | atcgggtcgt | ggtgatccag | gggatatatg | 300 |
| tcccccacaa | tcgtcaccta | tattattatt | ctttagatat | tatttaattt | ttggaaaaat | 360 |
| aacaaactta | tacttttgtg | tagggcctca | gcatagattt | tcgcttaggg | cccagaaatg | 420 |
| cgaggaccag | ccatgtctag | tgtccactat | tggcactacc | cagaacaaga | tttaaaaaaa | 480 |
| taaccaaagt | aactaatcca | ctcgaaagct | atcatgtaat | gtttaaagaa | acatctatta | 540 |
| aaaccacgat | cctcttaaaa | aacaagcata | tttcgaaaga | gacaaattat | gttacagttt | 600 |
| acaaacatct | aagagcgaca | aattatatcg | aaaggtaagc | tatgacgttc | agattttctct | 660 |
| ttttcattct | tgttattttg | ttattgtttt | tatatacatt | ttcttctctt | acaatagagt | 720 |
| gattttcttc | cgattttata | aaatgactat | aaagtcattt | ttatataaga | gcacgcatgt | 780 |
| cgtagattct | cgttcaaaaa | tcttttctgat | ttttttaaga | gctagtttgg | caaccctgtt | 840 |
| tctttcaaag | aattttgatt | ttttcaaaaa | aaattagttt | attttctctt | tataaaatag | 900 |
| aaaacactta | gaaaaataga | gttgccagac | tagccctaga | atgttttccc | aataaattac | 960 |
| aatcactgtg | tataattatt | tggccagccc | cataaaattt | ttaaaccgaa | actgaaatcg | 1020 |
| agcgaaacca | atctgagct | atttctctag | attagtaaaa | agggagagag | agaggaagaa | 1080 |

```
atcagtttta agtcattgtc cctgagatgt gcggtttggc aacgatagcc accgtaatca    1140
tagctcatag gtgcctacgt caggttcggc agctctcgtg tcatctcaca tggcatacta    1200
catgcttgtt caaccgttcg tcttgttcca tcgtccaagc cttgcctatt ctgaaccaag    1260
aggataccta ctcccaaaca atccatctta ctcatgcaac ttccatgcaa acacgcaca     1319

<210> SEQ ID NO 16
<211> LENGTH: 20
<212> TYPE: DNA
<213> ORGANISM: artificial
<220> FEATURE:
<223> OTHER INFORMATION: Ms45F1

<400> SEQUENCE: 16
cttgagcgac agcgggaact                                                  20

<210> SEQ ID NO 17
<211> LENGTH: 23
<212> TYPE: DNA
<213> ORGANISM: artificial
<220> FEATURE:
<223> OTHER INFORMATION: Ms45R1

<400> SEQUENCE: 17
tgttgtttct tggcaaaggt cag                                              23

<210> SEQ ID NO 18
<211> LENGTH: 650
<212> TYPE: DNA
<213> ORGANISM: artificial
<220> FEATURE:
<223> OTHER INFORMATION: Nucleotides encoding interfering RNA of CWI-2
      gene

<400> SEQUENCE: 18
taagtttcgc ttcggcgtgc ttgctgctgc tgttgcagct cgcaggagcg tcgcatgtcg      60
tctacaacta caaggacctc gaagccgagg ctgctgcggc gacggaccag gtgccgccgt     120
ccatcgtcaa cccctgctc aggacggggt accacttcca gccccccaag aactggatca     180
atgcgcccat gtactacaag gggtggtacc atttcttcta ccaatacaat cccaagggcg     240
ccgtatgggg caacatcgtg tggactagta gagggtaatt aagcaaaact tatccaaaac     300 taaacattt actattattt tgaccttttt attccactt tcttagacaa tgatttaacc       360
tcgtaatcaa ttgttaggat ttctagtcca cacgatgttg ccccatacgg cgcccttggg     420
attgtattgg tagaagaaat ggtaccaccc cttgtagtac atgggcgcat tgatccagtt     480 cttgggggc tggaagtggt accccgtcct gagcaggggg ttgacgatgg acggcggcac     540
ctggtccgtc gccgcagcag cctcggcttc gaggtccttg tagttgtaga cgacatgcga     600
cgctcctgcg agctgcaaca gcagcagcaa gcacgccgaa gcgaaactta                650
```

MALE STERILITY MAINTAINER LINE PLANT AND USE THEREOF

CROSS-REFERENCE TO RELATED APPLICATIONS

This application is the U.S. national stage entry of International Application No. PCT/CN2020/095082, filed Jun. 9, 2020, which claims priority to and the benefit of Chinese Application No. 201910496386.2, filed Jun. 10, 2019, the entire contents of which are incorporated by reference herein.

TECHNICAL FIELD

The present application pertains to the field of plant genetic breeding and seed production. Specifically, the present application relates to a male sterility maintainer line plant, a method for producing the male sterility maintainer line plant, and a use of the plant for expansion of male sterility line plant and male sterility maintainer line plant. In addition, the present invention also relates to a nucleic acid molecule, vector and host cell (for example, *Agrobacterium*) used to produce the male sterility maintainer line plant.

BACKGROUND ART

Heterosis makes the hybrid's biomass, resistance to diseases and insects, and tolerance to stresses (drought, high temperature, low temperature, saline alkali, etc.) to be considerably improved as compared to its parents. For example, the yields of hybrid maize and hybrid rice are much higher than their homozygous parents. The methods commonly used to produce hybrids comprise: planting female parent and male parent together; removing tassels of the female parent and retaining tassels of the male parent; harvesting seeds, i.e., hybrid seeds, from the female parent.

There are three types of plants in nature: self-pollination, cross-pollination and often cross-pollination. Self-pollination refers to a phenomenon that pollen of a plant pollinates its own pistil. For the plants with bisexual flowers, they can be divided into same-flower pollination (for example, *Phaseolus vulgaris*), neighbor-flower pollination and same-plant cross-pollination. Same-flower pollination refers to pollination between stamens and pistils of the same flower. Neighbor-flower pollination refers to pollination between different flowers of the same inflorescence (individual). Same-plant cross-pollination refers to pollination between different flowers of the same plant. For some plants, stamens and pistils do not grow on the same flower, and even do not grow on the same plant in some cases, so that self-pollination cannot be carried out, their pistils can only get pollen from other flowers, and this is called cross-pollination. A category of crops with a natural hybridization rate higher than 50% and with selfing depression is classified as often cross-pollinated crops.

Maize is a monoecious plant, and female and male flowers are located in different parts of the plant. Maize can reproduce by self-pollination or cross-pollination. Under natural conditions, when the wind blows pollen from tassels to filaments of female ear, natural pollination is completed. In maize breeding, a homozygous maize inbred line is usually developed first, and then two inbred lines are crossed to evaluate the yield and stress resistance of the hybrid offspring to determine whether it has commercial potential. Among them, each inbred line may have one or more excellent traits that another inbred line lacks, or make supplement to one or more undesirable traits of another inbred line. The first generation seeds of the two inbred lines are F1 generation seeds, the F1 generation plants are obtained after F1 generation seeds germinate, the F1 generation plants are stronger than the two inbred lines as parents (male parent and female parent), and possess more biomass at the same time.

Hybrids (F1) can be produced by artificially emasculating the female parent, that is, the unpolished female parent (which can be sown at intervals with the male parent in the field, such as sowing 5 rows of the female parent and one row of the male parent) is subjected to removal of tassels, while the male parent retains its tassels. Subsequently, as long as the foreign maize pollen is segregated, the female ears of the female parent can only receive the pollen from the male parent, and the resulting seeds are the hybrids (F1), which can be used for agricultural production. However, in the actual process of producing hybrids, changes in the environment may cause the plants to tassel again after the emasculation is completed, or the emasculation may be incomplete. The above two conditions can lead to self-pollination of the female parent, resulting in the hybrids produced mixed with the seeds of the female parent inbred line. Since the yield of female parent inbred line is much lower than that of hybrids, such seeds are substandard products, which will affect both the farmers' income and the reputation of seed production companies, and even cause seed production companies to bear corresponding liability of compensation. Machines can also be used to emasculate the female parent. The reliability of mechanical emasculation and manual emasculation are basically the same, but the former is faster and cheaper. However, most emasculation machines may cause more damage to plants than manual emasculation. Therefore, there is currently no satisfactory means of emasculation. People are still looking for alternatives methods to perform emasculation more thoroughly with lower cost.

The stable male sterility system provides a simple and efficient means of emasculation. By using a male sterility system, heavy work of emasculation can be avoided in some cases. The method comprises three main materials, namely (1) male sterility line (also referred to as sterile line): it is male sterile material; (2) male sterile maintainer line (also referred to as maintainer line): it can provide pollen for the sterile line, so that the offspring of the sterile line are still sterile line; (3) male sterile restoring line (also referred to as restoring line): it can restore the fertility of the sterile line. F1 is produced by crossing the sterile line with the restoring line, and is a hybrid for agricultural production.

Plant male sterility can be divided into three types: cytoplasmic male sterility, nuclear male sterility, and nucleo-cytoplasmic male sterility. Cytoplasmic male sterility plants are characterized by cytoplasmic inheritance, and single cytoplasmic genes S and N are usually used to represent male sterility and male fertility respectively, which are difficult to apply in agricultural production. Nuclear male sterility plants show nuclear inheritance; in most cases, male sterility is controlled by a pair of recessive genes (msms), and normal fertility is controlled by relatively dominant genes (MsMs) or (Msms). nucleo-cytoplasmic male sterility (CMS) plants show nucleo-cytoplasmic interaction inheritance. In short, only when the cytoplasm has the sterility gene S and the nucleus has homozygous sterility gene (rfrf), the plant will be male sterile. If the cytoplasm contains the fertility gene N, no matter whether the gene in the nucleus is a fertility gene (RfRf) or a sterility gene (rfrf), the plant will be male fertile. Similarly, if there is a fertility gene (RfRf) or (Rfrf) in the nucleus, no matter whether the gene in the cytoplasm is the fertility gene N or the sterility gene S, the plant will be male fertile.

The use of nucleo-cytoplasmic male sterility (CMS) materials for breeding has been reported. In this type of method, the genetic composition of the male sterility line is S (rfrf), which cannot produce normal pollen, but can be used as a hybrid female parent. The genetic composition of the maintainer line is N (rfrf), and the F1 produced by hybridizing it with the male sterility line can still maintain male sterility, namely: S (rfrf) (♀)×N (rfrf)→S (rfrf) (male sterility). The genetic composition of the restoring line is S (RfRf) or N (RfRf), and the F1 produced by hybridizing it with the male sterility line is restored to male fertility, namely: S (rfrf) (♀)×S (RfRf)→S (Rfrf) (F1) (fertile), or S (rfrf) (♀)×N (RfRf)→S (Rfrf) (F1) (fertile). The resulting F1 plants are self-bred to produce F2, and F2 can also be widely used in agricultural production. Male sterility lines can avoid manual emasculation, save manpower, reduce seed costs, and ensure seed purity. At present, crops such as rice, maize, Sorghum, onion, castor, sugar beet, and oilseed rape have used nucleo-cytoplasmic male sterility lines to produce hybrid seeds. The nucleo-cytoplasmic male sterility lines of other crops are also undergoing extensive research. However, the CMS system also has its shortcomings: one is that it is observed that individual CMS materials are susceptible to diseases, and the other is that the restoring system is more difficult to find. These problems hinder the widespread application of CMS system in seed production.

For the nuclear male sterility system, in most cases, the nuclear gene that controls male sterility is a recessive gene, and the plant will be male sterile only when it is homozygous (msms). However, since male sterility line plants cannot be self-bred, they can only be crossed with heterozygous plants (Msms) to obtain male sterility line plants (msms). However, on the progeny ears of heterozygous plants (Msms) and male sterility line plants (msms), male sterile seeds (msms) and fertile heterozygous seeds (Msms) exist at the same time, and it is impossible to distinguish which ones are sterile, and which ones are fertile; that is, they can only be distinguished after sowing and when the plants are dispersing pollen. This limits the wide application of nuclear male sterility system in seed production.

In recent years, a method of maintaining the sterility of male sterility line plants using transgenic methods has been reported (U.S. Pat. No. 6,743,968). The method comprises: firstly constructing a transgenic vector containing a pollen cell lethal gene and a dominant gene to restore plant fertility; then, transferring the vector into a male sterility line plant, and the vector at a heterozygous state exists in the transgenic plant. Due to the existence of the gene to restore fertility, the transgenic plant is male fertile. Moreover, when it is crossed with a male sterility line plant, since the pollen containing the fertility restoring gene (Msms) also contains the lethal gene, the pollen containing the fertility restoring gene will be aborted. Therefore, the transgenic plant can only produce pollen (ms) that does not contain the restoring gene, and crosses with female gamete (ms) of the male sterility line plant. The offspring produced are all recessive homozygous individuals (msms). That is, when such a plant is crossed with a male sterility line plant, its offspring all maintain the homozygous recessive state of the recessive sterile plant. However, the disadvantage of the above method is that due to the existence of heterofertilization (the embryo and endosperm are formed by fertilization with sperms developed from different male gametophytes, that is, the sperms that form the embryo and endosperm have different genotypes), there are still a certain proportion of fertile seeds in the offspring seeds obtained after the endosperm is screened, and these fertile seeds are difficult to distinguish from the sterile seeds and cannot fully meet the requirements of actual production.

In addition, a method has also been reported in which a vector containing both Ms45 and mn1 RNAi is used to construct a male sterile maintainer line and maintain the sterility of male sterility line plant (Chinese Patent ZL201210406155.6). However, due to the heterofertilization and other reasons, in the seeds obtained by screening endosperm phenotype, the endosperm does not contain genetically modified components, but the embryo may contain genetically modified components, which make these plants fertile, and these fertile seeds are difficult to be distinguished from the sterile seeds until the plants are dispersing pollen. However, removing the fertile plants when dispersing pollen will affect the purity of the breeding hybrids and cannot fully meet the needs of actual production. Therefore, it is necessary to establish a method to determine sterile plant and fertile plant after sowing and before dispersing pollen in order to remove the mixed fertile individual plants in time.

Therefore, how to improve the nuclear male sterility system to conveniently maintain the sterility of male sterility line plants and how to obtain high-purity male sterile offspring is an urgent problem in breeding. There is still a need in the art to develop more efficient methods for breeding male sterility line plants.

Contents of the Present Invention

In the present invention, unless otherwise specified, the scientific and technical terms used herein have the meanings commonly understood by those skilled in the art. In addition, the laboratory procedures of cell culture, molecular genetics, nucleic acid chemistry and botany used herein are all routine procedures widely used in the corresponding fields. At the same time, in order to better understand the present invention, definitions and explanations of related terms are provided below.

As used herein, the term "isolated" refers to a state obtained by artificial means, which is different from the natural state. For example, for a certain substance or component "isolated" from nature, it may be that the natural environment in which it is located has changed, or the substance has been isolated from the natural environment, or both. For example, for a certain unisolated polynucleotide or polypeptide naturally exists in a living animal, it is called isolated when the same polynucleotide or polypeptide with high purity is isolated from this natural state. The term "isolated" does not exclude the mixing of an artificial or synthetic material, nor does it exclude the presence of an impurity that does not affect the activity of the isolated material.

As used herein, the term "external trait" refers to a heritable and observable phenotypic characteristic exhibited by an individual (including seed and plant), which is usually controlled by one or more pairs of alleles. The "external traits" of seeds and plants mainly include the external morphological characteristics of roots, stems, leaves, flowers, fruits and seeds, such as seed color, seed size, plant color, plant wilting degree, stem morphology, leaf morphology, etc. Generally, the external traits of seeds mainly refer to the external morphological characteristics of seeds, including, for example, seed color or seed size. The external traits of plants mainly refer to the external morphological characteristics of roots, stems, leaves, flowers and fruits, including, for example, plant color or plant wilting degree.

As used herein, the term "male sterility" refers to a phenomenon in which male cells or tissues of plants lose their physiological functions. Generally, in sexual-reproductive plants (for example, maize), male sterility is manifested by the abnormal development of male tissues (for example, stamens) and the inability to produce pollen with normal functions, but the development of female tissues (for example, pistils) is normal, which can accept normal pollen and be fertilized. As used herein, the term "male sterility gene" refers to a gene capable of controlling male sterility traits in plants. In the present application, preferably, the male sterility gene is a nuclear male sterility gene. In most cases, the nuclear gene that controls male sterility is a recessive gene, and the plant will only show male sterility when it is homozygous (msms). For example, for the male sterile maize line Zheng58, it has a homozygous recessive male sterility gene (ms45ms45). In the present application, it is particularly preferred that the male sterility gene is a recessive gene, which causes plant male sterility in a homozygous state.

As used herein, the term "restoring gene" refers to a gene capable of restoring the male fertility of plants that are male sterile due to the male sterility gene. When the restoring gene is introduced into a male sterility line plant, the plant will restore male fertility. In the present application, when the male sterility gene is a recessive gene, the restoring gene may be a dominant allele of the recessive gene.

A variety of recessive genes that can cause male sterility in plants and their corresponding dominant alleles that can restore male fertility in plants have been reported. For example, a variety of recessive male sterility genes and their corresponding dominant allelic restoring genes have been identified in maize, including but not limited to those shown in Table 1 (Skibbe et al. 2005).

TABLE 1

Recessive male sterility genes in maize and their corresponding dominant allelic restoring genes

| Male sterility gene | Restoring gene | Chromosome | Reference |
|---|---|---|---|
| ms1 | Ms1 | 6 | SINGLETON and JONES (1930); ALBERTSEN and PHILLIPS (1981) |
| ms2 | Ms2 | 9 | EYSTER (1931); ALBERTSEN and PHILLIPS (1981) |
| ms3 | Ms3 | 3 | EYSTER (1931) |
| m54(po1) | Ms4 | | BEADLE (1932) |
| ms5 | Ms5 | 5 | BEADLE (1932); ALBERTSEN and PHILLIPS (1981) |
| ms6(po1) | Ms6 | | BEADLE (1932); ALBERTSEN and PHILLIPS (1981) |
| ms7 | Ms7 | 7 | BEADLE (1932); ALBERTSEN and PHILLIPS (1981) |
| ms8 | Ms8 | 8 | BEADLE (1932); ALBERTSEN and PHILLIPS (1981) |
| ms9 | Ms9 | 1 | BEADLE (1932); ALBERTSEN and PHILLIPS (1981) |
| ms10 | Ms10 | 10 | BEADLE (1932); ALBERTSEN and PHILLIPS (1981) |
| ms11 | Ms11 | 10 | BEADLE (1932); ALBERTSEN and PHILLIPS (1981) |
| ms12 | Ms12 | 1 | BEADLE (1932); ALBERTSEN and PHILLIPS (1981) |
| ms13 | Ms13 | 5 | BEADLE (1932); ALBERTSEN and PHILLIPS (1981) |
| ms14 | Ms14 | 1 | BEADLE (1932); ALBERTSEN and PHILLIPS (1981) |
| ms15 | Ms15 | | BEADLE (1932) |
| ms16 | Ms16 | | BEADLE (1932) |
| ms17 | Ms17 | 1 | EMERSON (1932a); ALBERTSEN and PHILLIPS (1981) |
| ms18 | Ms18 | 1 | EYSTER (1934) |
| ms19 | Ms19 | 9 | EYSTER (1934) |
| ms20 | Ms20 | | EYSTER (1934) |
| ms21 | Ms21 | 6 | SCHWARTZ (1951) |
| ms22 (mscal) | Ms22 | 7 | WEST and ALBERTSEN (1985); TRIMNELL et al. (2001); CHAUBAL et al. (2003) |
| ms23 | Ms23 | | WEST and ALBERTSEN (1985); CHAUBAL et al. (2000) |
| ms24 | Ms24 | 10 | WEST and ALBERTSEN (1985); FOX et al. (2002) |
| ms25 | Ms25 | 9 | LOUKIDES et al. (1995) |
| ms26 | Ms26 | 1 | LOUKIDES et al. (1995); PCT/US2006/024273 |
| ms27 | Ms27 | | ALBERTSEN (1996); BEDINGER (unpublished) |
| ms28 | Ms28 | 1 | GOLUBOVSKAYA and SITNOKOVA (1980) |
| ms29 | Ms29 | 10 | TRIMNELL et al. (1998a) |
| ms30 (msx) | Ms30 | 4 | TRIMNELL et al. (1998b) |
| ms31 | Ms31 | 2 | TRIMNELL et al. (1998b) |
| ms32 | Ms32 | 2 | CHAUBAL et al. (2000) |
| ms33 | Ms33 | 2 | TRIMNELL et al. (1999d) |
| ms34 | Ms34 | 7 | TRIMNELL et al. (1999b) |
| ms35 (ms23) | Ms35 | | TRIMNELL et al.(1999c, 2002a); ALBERTSEN(personal communication) |
| ms36 | Ms36 | 9 | TRIMNELL et al. (1999c) |
| ms37 | Ms37 | 3 | TRIMNELL et al. (1999a) |
| ms38 (ms*WL89A) | Ms38 | 2 | TRIMNELL et al. (1998a); ALBERTSEN et al. (1999) |
| ms43 | Ms43 | 8 | GOLUBOVSKAYA (1979) |
| ms45 | Ms45 | 9 | ALBERTSEN et al. (1993a) |
| ms47 | Ms47 | 10 | TRIMNELL et al. (2002b) |
| ms48 | Ms48 | 9 | TRIMNELL et al. (2002c) |
| ms49 | Ms49 | 10 | TRIMNELL et al. (2002d) |
| ms50 | Ms51 | 6 | TRIMNELL et al. (2002e) |
| ms52 | Ms52 | 10 | ALBERTSEN (personal communication) |

As used herein, the term "a screening gene for regulating seed color" refers to a gene that can affect seed color by affecting the synthesis of pigments, anthocyanins, and the like. Such a gene includes, for example, Lc gene (Ludwig S R et al., Proc Natl Acad Sci, 1989 September; 86(18): 7092-6; Wang Juan et al., Genomics and Applied Biology, Issue 02, 2009). Lc gene is a regulatory gene related to anthocyanin synthesis. Its heterologous expression in a variety of plants (for example, maize) can affect anthocyanin synthesis, increase anthocyanin content, and affect seed color. The expression of this gene can make maize seeds appear purple. In addition, it has also been found that Lc gene can affect plant color. The expression of this gene can make maize plants appear purple. Therefore, Lc gene is also a "screening gene for regulating plant color".

As used herein, the term "a screening gene for regulating seed size" refers to a gene whose expression level can affect seed size. Such a gene includes, for example, CWI-2 gene (W. H. Cheng et al., Plant Cell. 1996 June; 8(6): 971-983). CWI-2 gene encodes a cell wall invertase specifically expressed in endosperm. After the gene is silenced or mutated, the normal development of seed endosperm is affected, which causes the seed to become smaller, but does not affect the germination rate and plant development.

As used herein, the term "a screening gene for regulating plant color" refers to a gene that can affect plant color by affecting the synthesis of chloroplasts, pigments, anthocyanins, and the like. Such a gene includes, for example, Oy1 gene (Ruairidh J. H. Sawers et al., Plant Molecular Biology, volume 60, pages 95-106 (2006)). Oy1 gene is a regulatory gene related to chloroplast synthesis, which can affect plant the color of plants (for example, maize plants) by affecting chloroplast synthesis. The expression of this gene can make maize plants appear yellow.

As used herein, the term "a screening gene for regulating plant wilting degree" refers to a gene that can affect plant wilting by regulating plant stomatal aperture, water transport, and so on. Such a gene includes, for example, Wi2 gene (Chris Rock et al., American Journal of Botany, 86(12): 1796-800 (2000)). Wi2 gene is a regulatory gene related to the synthesis of suberin in plant roots, which can affect the wilting degree of plants (for example, maize) by affecting plant water transport. The expression of this gene can make maize leaves wilting.

As used herein, the term "a tissue-preferred promoter" refers to a promoter that can preferentially initiate transcription in certain plant tissues (for example, stamens, pollen sacs, filaments, and pollen). As used herein, the term "a growth stage-preferred promoter" refers to a promoter that can preferentially initiate transcription in certain growth and development stages (for example, sporogenous tissue, microspores, and microgametophytes). As used herein, the term "a tissue-specific promoter" refers to a promoter that specifically initiates transcription only in certain plant tissues.

As used herein, the term "a selective marker gene" refers to a gene whose coded product enables the transformed or transfected host cells to grow normally or exhibit other visual characteristics under selective pressure. Such selective pressure includes, but is not limited to, the addition of selective agents (for example, antibiotics or herbicides) or the lack of nutrients. As used herein, the term "an antibiotic resistance gene" refers to a gene whose coded product enables the transformed or transfected host cells to grow normally or exhibit other visual characteristics under the selective pressure of the antibiotic. As used herein, the term "a herbicide resistance gene" refers to a gene whose encoded product enables the transformed or transfected host cells to grow normally or exhibit other visual characteristics under the selective pressure of the herbicide.

As used herein, the term "heterofertilization" refers to a phenomenon in which the embryo and endosperm of the same seed are fertilized by sperms formed by two different male gametophytes during double fertilization. In this case, the embryo and endosperm of the same seed may have different genotypes.

In the present application, a plant can be all or part of plant, such as root, stem, leaf, embryo, root tip, pollen, or anther.

Through careful design and a large number of experiments, the inventors of the present application obtained a maintainer line plant capable of maintaining the sterility of a male sterility line plant. When the maintainer line plant is crossed with a male sterility line plant, the distinguishable offsprings of sterile line and maintainer line can be simultaneously obtained, which significantly improves the propagation efficiency and breeding efficiency of sterile line plants. Based on this, the present application also provides a method for producing the maintainer line plant and a method for expanding propagation of a sterile plant by using the maintainer line plant. In addition, in certain preferred embodiments of the present application, the maintainer line plant comprises a double screening gene, and after the maintainer line plant is crossed with a male sterility line plant, the offsprings of sterile line and maintainer line can be distinguished more accurate by the double screening method, which further improve the breeding efficiency. Thus, the inventors of the present application completed the present invention.

Therefore, in the first aspect, the present application provides an isolated nucleic acid molecule, which comprises a first polynucleotide and a second polynucleotide, the first polynucleotide comprises a nucleotide sequence of a restoring gene, the restoring gene can restore the male fertility of a plant that has male sterility caused by a male sterility gene; the second polynucleotide comprises a nucleotide sequence of a screening gene capable of regulating an external trait of a seed and/or plant, the external trait is selected from the group consisting of seed color, seed size, plant color, plant wilting degree, stem morphology, leaf morphology, and any combination thereof. In certain embodiments, the external trait is selected from the group consisting of seed color, plant color, plant wilting degree, and any combination thereof.

In certain embodiments, the external trait is a combination of seed external trait (for example, seed color or seed size) and plant external trait (for example, plant color or plant wilting degree). In certain embodiments, the external trait is a combination of seed color and plant color. In certain embodiments, the external trait is a combination of seed size and plant color. In certain embodiments, the external trait is a combination of seed color and plant wilting degree. In certain embodiments, the external trait is a combination of seed size and plant wilting degree.

In the present application, in some cases, the simultaneous use of two or more external traits is preferable and advantageous. For example, in some embodiments, a screening gene for regulating seed external trait (for example, seed color or seed size) and a screening gene for regulating plant external trait (for example, plant color or plant wilting degree) can be used in combination. As a result, the seed external trait and the plant external trait can be used to screen the hybrid offspring, so as to ensure the purity of the hybrid offspring.

Therefore, in certain embodiments, the second polynucleotide comprises: (a) a first screening gene capable of regulating a seed external trait (for example, seed color or seed size), and (b) a second screening gene capable of regulating a plant external trait (for example, plant color or plant wilting degree).

In certain embodiments, the first screening gene and the second screening gene are the same. In such embodiments, the second polynucleotide comprises a screening gene capable of controlling a seed external trait and a plant external trait. For example, in some embodiments, the screening gene is Lc gene, which can control seed color and plant color. In certain embodiments, the Lc gene encodes a protein with an amino acid sequence of SEQ ID NO: 5. In certain embodiments, the Lc gene has a nucleotide sequence of SEQ ID NO: 4.

In certain embodiments, the first screening gene and the second screening gene are different. For example, in certain embodiments, the second polynucleotide comprises:

(1) a first screening gene capable of regulating seed color and a second screening gene capable of regulating plant color,
(2) a first screening gene capable of regulating seed color and a second screening gene capable of regulating plant wilting degree,
(3) a first screening gene capable of regulating seed size and a second screening gene capable of regulating plant color, or,
(4) a first screening gene capable of regulating seed size and a second screening gene capable of regulating plant wilting degree.

In certain embodiments, the second polynucleotide comprises: Lc gene and Wi2 gene. In certain embodiments, the second polynucleotide comprises: nucleotides encoding an interfering RNA of CWI-2 gene, and Lc gene. In certain embodiments, the second polynucleotide comprises: nucleotides encoding an interfering RNA of CWI-2 gene, and Oy1 gene. In certain embodiments, the second polynucleotide comprises: nucleotides encoding an interfering RNA of CWI-2 gene, and Wi2 gene.

In some embodiments, the nucleotides encoding the interfering RNA of CWI-2 gene have a nucleotide sequence shown in SEQ ID NO: 18.

In certain embodiments, the Oy1 gene encodes a protein with an amino acid sequence of SEQ ID NO: 7. In certain embodiments, the nucleotide sequence of the Oy1 gene is SEQ ID NO: 6.

In some embodiments, the Wi2 gene encodes a protein with an amino acid sequence of SEQ ID NO: 9. In certain embodiments, the nucleotide sequence of the Wi2 gene is SEQ ID NO: 8.

In certain embodiments, the second polynucleotide further comprises an expression regulatory element, such as a promoter and an enhancer, operably linked to the nucleotide sequence of the screening gene. In certain embodiments, the expression regulatory element is selected from the group consisting of promoter, enhancer, regulatory sequence, inducible element, and any combination thereof. In some embodiments, the promoter is selected from: constitutive promoter, inducible promoter, tissue-preferred promoter, tissue-specific promoter, and growth-phase-preferred promoter. The promoters that can be used in the present application are not limited to the promoters listed above. It is easy to understand that in the embodiments of the present application, any promoter known to those skilled in the art can be used according to actual needs.

In certain embodiments, the male sterility gene is a recessive male sterility gene, which causes plant male sterility in a homozygous state.

In certain embodiments, the male sterility gene is selected from ms1, ms2, ms3, ms4, ms5, ms6, ms7, ms8, ms9, ms10, ms11, ms12, ms13, ms14, ms15, ms16, ms17, ms18, ms19, ms20, ms21, ms22, ms23, ms24, ms25, ms26, ms27, ms28, ms29, ms30, ms31, ms32, ms33, ms34, ms35, ms36, ms37, ms38, ms43, ms45, ms47, ms48, ms49, Ms50, ms52, and any combination thereof. In certain embodiments, the male sterility gene is ms45.

In certain embodiments, the restoring gene is selected from Ms1, Ms2, Ms3, Ms4, Ms5, Ms6, Ms7, Ms8, Ms9, Ms10, Ms11, Ms12, Ms13, Ms14, Ms15, Ms16, Ms17, Ms18, Ms19, Ms20, Ms21, Ms22, Ms23, Ms24, Ms25, Ms26, Ms27, Ms28, Ms29, Ms30, Ms31, Ms32, Ms33, Ms34, Ms35, Ms36, Ms37, Ms38, Ms43, Ms45, Ms47, Ms48, Ms50, Ms52, and any combination thereof. In certain embodiments, the restoring gene is Ms45.

It is easy to understand that in the embodiments of the present application, the restoring gene should correspond to the male sterility gene, so that it can save the sterility traits caused by the male sterility gene. In the present application, preferably, the male sterility gene is a recessive gene, and the restoring gene may be a dominant allele of the recessive gene, which can restore the male fertility of the plant.

In certain embodiments, the male sterility gene is ms45, and the restoring gene is Ms45.

In certain embodiments, the restoring gene encodes a protein with an amino acid sequence of SEQ ID NO: 2. In some embodiments, the nucleotide sequence of the restoring gene is SEQ ID NO:1.

In certain embodiments, the first polynucleotide further comprises an expression regulatory element, such as a promoter and an enhancer, operably linked to the nucleotide sequence of the restoring gene. In certain embodiments, the expression regulatory element is selected from the group consisting of promoter, enhancer, regulatory sequence, inducible element, and any combination thereof. In some embodiments, the promoter is selected from: constitutive promoter, inducible promoter, tissue-preferred promoter, tissue-specific promoter, and growth-phase-preferred promoter. The promoters that can be used in the present application are not limited to the promoters listed above. It is easy to understand that in the embodiments of the present application, any promoter known to those skilled in the art can be used according to actual needs.

In certain embodiments, the nucleotide sequence of the promoter is SEQ ID NO: 15.

In certain embodiments, the first polynucleotide sequence comprises or consists of SEQ ID NO: 3.

In certain embodiments, the first polynucleotide and the second polynucleotide are covalently linked with or without a nucleotide linker. In certain embodiments, the nucleotide linker has a length of not more than 10 kb, not more than 5 kb, not more than 1 kb, not more than 500 bp, not more than 100 bp, not more than 50 bp, not more than 10 bp, not more than 5 bp, or shorter. In certain embodiments, the first nucleotide sequence and the second nucleotide sequence are genetically linked.

In certain embodiments, the isolated nucleic acid molecule further comprises a third polynucleotide, the third polynucleotide comprises a nucleotide sequence of a selective marker gene. In some embodiments, the selective marker gene is an antibiotic resistance gene or a herbicide resistance gene, such as a bialaphos resistance gene (bar gene). The selective marker genes that can be used in the embodiments of the present application include, but are not limited to, neomycin resistance gene (for example, a gene encoding neomycin phosphotransferase), hygromycin resistance gene (for example, a gene encoding hygromycin phosphotransferase), chloramphenicol resistance gene, streptomycin resistance gene, spectinomycin resistance gene, bleomycin resistance gene, sulfonamide resistance gene, bromoxynil resistance gene, glyphosate resistance gene, bialaphos resistance gene and glufosinate resistance gene. In certain embodiments, the selective marker gene is a herbicide resistance gene. In certain embodiments, the herbicide resistance gene is the bar gene. In certain embodiments, the nucleotide sequence of the selective marker gene is SEQ ID NO: 10.

In the second aspect, the present application provides a vector, which comprises the isolated nucleic acid molecule as described above.

In certain embodiments, the vector can be a cloning vector, a transfer vector, or an expression vector. In certain embodiments, the vector is a plasmid (for example, pCAMBAI3301), cosmid, phage, and the like. In certain embodiments, the vector is capable of expressing the isolated nucleic acid molecule as described above in a plant cell (for example, maize).

In the third aspect, the present application provides a host cell, which comprises the isolated nucleic acid molecule as described above or the vector as described above.

In certain embodiments, the host cell is an *Agrobacterium* cell (for example, *Agrobacterium* EHA105) or a plant cell (for example, maize). In certain embodiments, the plant cell is a cell of a monocotyledon or a dicotyledon. In certain embodiments, the plant cell is a plant cell selected from the group consisting of maize (*Zea mays*), rape (*Brassica napus*), rice (*Oryza sativa*), Arabidopsis (*Arabidopsis thaliana*), barley (*Hordeum vulgare*), wheat (*Triticumaestivum*), Sorghum (*Sorghum bicolor*), soybean (*Glycine max*), alfalfa (*Medicago sativa*), tobacco (*Nicotiana tabacum*), cotton (*Gossypiumhirsutum*), sunflower (*Helianthus annuus*) or sugarcane (*Saccharum officinarum*).

The application also provides a tissue culture of the host cell, and a protoplast produced from the tissue culture.

In the fourth aspect, the present application provides a plant or plant seed, wherein the plant or plant seed comprises the nucleic acid molecule as described above in its genome.

In some embodiments, the plant or plant seed further comprises the male sterility gene (for example, ms45) in the genome. In certain embodiments, the male sterility gene is a homozygous recessive male sterility gene (for example, ms45ms45).

In certain embodiments, the isolated nucleic acid molecule is integrated in the genome of the plant or plant seed. In certain embodiments, the isolated nucleic acid molecule is integrated in the genome of the plant or plant seed, and is located on a chromosome different from the male sterility gene. In certain embodiments, the nucleic acid molecule is present in a heterozygous form in the genome of the plant or plant seed. As used herein, the term "present in a heterozygous form" has the meaning commonly understood by those skilled in the art. For example, it may mean that the same allele does not exist at the gene locus corresponding to the position where the nucleic acid molecule is integrated into the plant genome (i.e., heterozygosis). For example, the nucleic acid molecule is only present in one chromatid, and is not contained in the sister chromatid thereof.

Any method known to those skilled in the art can be used to integrate the nucleic acid molecule into the genome of the plant or plant seed. Such methods comprise, but are not limited to, stable transformation methods, transient transformation methods, virus-mediated methods, and *Agrobacterium*-mediated methods.

In certain embodiments, the plant or plant seed is male fertile. In certain embodiments, the plant or plant seed can be used as a maintainer line for a male sterility line plant containing the male sterility gene.

In certain embodiments, the plant or plant seed is a plant or plant seed of a monocotyledon or a dicotyledon. In certain embodiments, the plant or plant seed is a plant or plant seed of maize, rape, rice, arabidopsis, barley, wheat, *Sorghum*, soybean, alfalfa, tobacco, cotton, sunflower, or sugarcane.

In the fifth aspect, the present application provides a method for obtaining a plant, the method comprises, (1) introducing the nucleic acid molecule as described above or the vector as described above into a plant cell, and (2) cultivating the plant cell into a plant.

Any method known to those skilled in the art can be used to introduce the nucleic acid molecule or vector into the plant cell. Such methods comprise, but are not limited to, stable transformation methods, transient transformation methods, virus-mediated methods, and *Agrobacterium*-mediated methods. In addition, any method known to those skilled in the art can be used to cultivate the plant cell into the plant. For example, the method described in McCormicketal. (1986) Plant Cell Reports 5: 81-84 is referred to.

In some embodiments, in step (1), an *Agrobacterium*-mediated method is used. In some embodiments, in step (1), the nucleic acid molecule or the vector is introduced into the plant cell by an *Agrobacterium*.

In certain embodiments, the plant cell comprises the male sterility gene in its genome, and preferably, the plant cell is male sterile before the nucleic acid molecule or vector is transformed. In certain embodiments, the plant cell comprises a homozygous recessive male sterility gene in its genome.

In some embodiments, in step (1), the nucleic acid molecule is integrated into a genome of the plant cell. In certain embodiments, the nucleic acid molecule is located on a chromosome different from the male sterility gene after being integrated into the genome of the plant cell.

In certain embodiments, the plant cell is a cell of a monocotyledon or a dicotyledon. In certain embodiments, the plant cell is a cell of a plant selected from the group consisting of maize, rape, rice, arabidopsis, barley, wheat, *Sorghum*, soybean, alfalfa, tobacco, cotton, sunflower, or sugarcane.

In certain embodiments, the plant comprises a homozygous recessive male sterility gene, and the nucleic acid molecule or the vector, and it is male fertile. In certain embodiments, the nucleic acid molecule or the vector is present in a heterozygous form in the genome of the plant. In certain embodiments, the nucleic acid molecule is integrated in the genome of the plant and is located on a chromosome different from the male sterility gene.

In certain embodiments, the plant can be used as a maintainer line plant of a male sterility line plant comprising the male sterility gene.

In some embodiments, the method further comprises:
(3) pollinating the male sterility line plant containing the male sterility gene with the plant of step (2) to produce offspring seeds or plants; and
(4) Screening the offspring seeds or plants showing the external traits regulated by the screening gene.

In the sixth aspect, the present application provides a method for obtaining an offspring seed or plant of a male sterility line plant and maintainer line plant, the method comprising: crossing the plant as described above or the plant obtained by the method as described above as a male parent with a male sterility line plant containing the male sterility gene as a female parent, and producing an offspring seed or plant.

In certain embodiments, the method comprises:
(1) providing a male sterility line plant containing the male sterility gene as a female parent; preferably, the male sterility gene is a homozygous recessive male sterility gene (for example, ms45ms45);
(2) providing the above-mentioned plant or the plant obtained by the above-mentioned method as a male parent;
(3) pollinating the plant of step (1) with the plant of step (2) to produce an offspring seed;
(4) optionally, cultivating the offspring seed into an offspring plant;
wherein, the offspring seed or plant that shows an external trait regulated by the screening gene is male fertile, and can be used as a maintainer line; and, the offspring seed or plant that does not show an external trait regulated by the screening gene is male sterile, and can be used as a male sterility line.

In the present application, the simultaneous use of two or more external traits is preferable and advantageous in some cases. For example, in some embodiments, the plant used as the male parent in step (2) may comprise: (a) a first screening gene capable of regulating a seed external trait (for example, seed color or seed size), and (b) a second screening gene capable of regulating a plant external trait (for example, plant color or plant wilting degree). Therefore, after crossing the plant of step (2) with the plant of step (1), the seed external trait (for example, seed color or seed size) and the plant external trait (for example, plant color or plant wilting degree) can be used to screen the hybrid offspring to ensure the purity of the hybrid offspring.

Therefore, in certain embodiments, the method comprises:
(1) providing a male sterility line plant containing the male sterility gene as a female parent; preferably, the male sterility gene is a homozygous recessive male sterility gene;
(2) providing the above-mentioned plant or the plant obtained by the above-mentioned method as a male parent; wherein, the second polynucleotide comprises:
(a) a first screening gene capable of regulating a seed external trait (for example, seed color or seed size), and
(b) a second screening gene capable of regulating a plant external trait (for example, plant color or plant wilting degree);
(3) pollinating the plant of step (1) with the plant of step (2) to produce two offspring seeds; wherein, the first offspring seeds show the seed external trait regulated by the first screening gene; and, the second offspring seeds do not show the seed external trait regulated by the first screening gene;
(4) separating the first and second offspring seeds, and optionally, cultivating them into first and second offspring plants, respectively.

Optionally, the method further comprises the following steps:
(5) removing from the first offspring plants a plant that does not show the plant external trait regulated by the second screening gene, so that the remaining first offspring plant is male fertile and can be used as a maintainer line plant; and/or
removing from the second offspring plants a plant that shows the plant external trait regulated by the second screening gene, so that the remaining second offspring plant is male sterile and can be used as a male sterility line plant;
(6) using the remaining first offspring plants to pollinate the remaining second offspring plants so as to produce a further offspring seed.

In yet another aspect, the present application provides a method for preparing a hybrid seed, the method comprising:
(1) provide an offspring seed of the male sterility line plant obtained by the method described above, which does not show the seed external trait regulated by the first screening gene; and, providing a target line plant seed;
(2) sowing the offspring seed of the male sterility line plant and the target line plant seed in a field to obtain a male sterility line plant and a target line plant;
(3) removing from the male sterility line plant a plant that shows the plant external trait regulated by the second screening gene;
(4) pollinate the remaining male sterility line plant with the target line plant;
(5) harvesting a seed from the male sterility line plant, which is the hybrid seed.

The method of the present application can use two or more external traits to screen and distinguish the male sterility line plant offspring and the maintainer line plant offspring, and in this way, "false positive" or "false negative" traits caused by heterofertilization, gene mutation, gene loss, chromosome recombination, chromosome translocation, etc. during the breeding process are avoided, thereby further improving the purity of the male sterility line plant offspring and the maintainer line plant offspring, and increasing the breeding efficiency as well as the quality and purity of the produced hybrid seeds.

In certain embodiments, the first screening gene and the second screening gene are the same. In such embodiments, the second polynucleotide comprises a screening gene capable of controlling a seed external trait and a plant external trait. For example, in some embodiments, the screening gene is Lc gene, which can control seed color and plant color. In certain embodiments, the Lc gene encodes a protein with an amino acid sequence of SEQ ID NO: 5. In certain embodiments, the nucleotide sequence of the Lc gene is SEQ ID NO: 4.

In certain embodiments, the first screening gene and the second screening gene are different. For example, in certain embodiments, the second polynucleotide comprises:
(1) a first screening gene capable of regulating seed color and a second screening gene capable of regulating plant color,
(2) a first screening gene capable of regulating seed color and a second screening gene capable of regulating plant wilting degree,
(3) a first screening gene capable of regulating seed size and a second screening gene capable of regulating plant color, or,
(4) a first screening gene capable of regulating seed size and a second screening gene capable of regulating plant wilting degree.

In certain embodiments, the second polynucleotide comprises: Lc gene and Wi2 gene. In certain embodiments, the second polynucleotide comprises: nucleotides encoding an interfering RNA of CWI-2 gene, and Lc gene. In certain embodiments, the second polynucleotide comprises: nucleotides encoding an interfering RNA of CWI-2 gene, and Oy1 gene. In certain embodiments, the second polynucleotide comprises: nucleotides encoding an interfering RNA of CWI-2 gene, and Wi2 gene.

In some embodiments, the nucleotides encoding the interfering RNA of CWI-2 gene have the nucleotide sequence shown in SEQ ID NO: 18.

In certain embodiments, the Oy1 gene encodes a protein with an amino acid sequence of SEQ ID NO: 7. In certain embodiments, the nucleotide sequence of the Oy1 gene is SEQ ID NO: 6.

In some embodiments, the Wi2 gene encodes a protein with an amino acid sequence of SEQ ID NO: 9. In certain embodiments, the nucleotide sequence of the Wi2 gene is SEQ ID NO: 8.

In the seventh aspect, the present application provides a product, which is made from the plant as described above or a part thereof. In certain embodiments, the product is a food product, and it is made from an edible part (for example, seed) of the plant as described above.

In the eighth aspect, the present application provides a use of the above-mentioned nucleic acid molecule or the above-mentioned vector or the above-mentioned host cell (for example, plant cell) for the production of a maintainer line plant. In the ninth aspect, the present application provides a use of the plant or the offspring seed or plant obtained by the method described above or the plant described above for the production of a hybrid offspring (for example, plant or seed). In the tenth aspect, the present application provides a tissue culture or a protoplast produced therefrom, wherein the tissue culture comprises the host cell (for example, plant cell) as described above or a cell of the plant obtained by the method as described above or a cell of the offspring seed or plant obtained by the method described above.

In certain embodiments, the plant is a monocotyledon or a dicotyledon. In certain embodiments, the plant is a plant selected from the group consisting of maize, rape, rice, arabidopsis, barley, wheat, Sorghum, soybean, alfalfa, tobacco, cotton, sunflower, or sugarcane.

In addition, the present application also discloses the following technical solutions:

One object of the present invention is to provide a method. The method provided by the present invention is used to maintain the homozygous recessive state of male sterility line plants, and the method comprises:

(a) providing a first plant, which comprises a homozygous recessive allele that makes the plant male sterile (for example, the homozygous recessive allele is specifically ms45ms45);

(b) provide a second plant, which comprises the same homozygous recessive allele as the first plant that makes the plant male sterile, and comprises the following construct, the construct (for example, transgenic element Ms45-Lc or Ms45-Oy1 or Ms45-Wi2) exists in a heterozygous state in the second plant (heterozygous Ms45-Lc/- or Ms45-Oy1/- or Ms45-Wi2/-insertion element exists in only one chromatid, and its sister chromatid does not comprise a transgenic element), and the construct comprises:

i. a first nucleotide sequence, expression of which in the first plant will restore the male fertility of the first plant;

ii. a second nucleotide sequence, when existing in a heterozygous state, which can affect plant color (for example, Lc gene makes plant and/or seed purple, or, Oy1 gene makes plant yellow) or affect plant morphology (for example, Wi2 gene makes plant top leaves wilting), so that a plant or seed containing the construct can be distinguished from a plant or seed not containing the construct by a naked eye or instrument; the first nucleotide sequence (for example, Ms45 gene expression element shown in SEQ ID NO: 3) and the second nucleotide sequence (for example, Lc gene shown in SEQ ID NO: 4, or Oy1 gene shown in SEQ ID NO: 6, or Wi2 gene shown in SEQ ID NO: 8) are closely linked, and these two nucleotide sequences are present in the plant at the same time (for example, the transgenic elements Ms45-Lc, Ms45-Oy1 or Ms45-Wi2 in the examples);

(c) fertilizing a female gamete of the first plant with a male gamete of the second plant to produce an offspring that maintains the homozygous recessive state of the first plant.

The above method is a method for expanding propagation of a male sterility line plant;

and/or, the plant, the first plant and the second plant are all dicotyledon or monocotyledon;

and/or, the plant, the first plant and the second plant may all be not only maize (Zea mays), but also rice (Oryza sativa), Sorghum (Sorghum bicolor), wheat (Triticumaestivum), soybean (Glycine max), cotton (Gossypiumhirsutum), sunflower (Helianthus annuus) and other crops.

In the above method, the first nucleotide sequence comprises a restoring gene for controlling male fertility, such as the wild-type allele Ms45 of ms45 in Table 1. This restoring gene for controlling male fertility is not limited to the genes listed in Table 1. The restoring genes for controlling male fertility in maize or other species can also achieve the purpose of the present invention, and therefore are also within the protection scope of the present invention.

In the above method, in the embodiments of the present invention, the first plant is a maize male sterile mutant ms45, specifically a ms45 homozygous recessive inbred line Zheng58 (Zheng58(ms45ms45)), which is derived from a backcross offspring of ms45 homozygous recessive mutant (Maize Genetics Cooperation Stock Center, 905I) and Zheng58 (zheng58).

The first nucleotide sequence is a Ms45 gene expression element in the embodiments of the present invention, and the Ms45 gene expression element expresses a protein Ms45 in the first plant.

The protein Ms45 is as follows a) or b):

a) a protein composed of amino acid residues shown in SEQ ID NO: 2;

b) a protein with the same function as SEQ ID NO: 2 after substitution and/or deletion and/or addition of one or several amino acid residues in SEQ ID NO: 2.

In the above method, the Ms45 gene expression element comprises Ms45 gene promoter, Ms45 gene 5'UTR, Ms45 gene exon, Ms45 gene intron, Ms45 gene 3'UTR and Ms45 gene terminator;

the Ms45 gene expression element is a DNA molecule shown in 1) or 2) or 3) as follows:

1) a DNA molecule with a coding region comprising SEQ ID NO: 1;

2) a DNA molecule with a coding region of SEQ ID NO: 1;

3) a DNA molecule with the same function as 1) or 2) after substitution and/or deletion and/or addition of one or several nucleotides in 1) or 2).

In the above method, the second nucleotide sequence comprises a gene for controlling plant color or controlling plant seed color or controlling plant wilting degree.

In the above method, when the second nucleotide sequence exists in a heterozygous state in the second plant, it affects the plant color or seed color or plant wilting degree of the second plant.

In an embodiment of the present invention, the above-mentioned gene controlling plant color or controlling plant seed color is the key gene Lc for anthocyanin synthesis; the above-mentioned key gene Lc for anthocyanin synthesis expresses a protein LC in the second plant. When the second nucleotide sequence exists in a heterozygous state in the second plant, it affects whether the seed or plant color of the second plant is purple; if the second nucleotide sequence is contained, the seed or plant color is purple, otherwise, the seed or plant color is not purple.

In another embodiment of the present invention, the above-mentioned gene for controlling plant color is the gene Oy1 related to chlorophyll synthesis; the above-mentioned Oy1 gene expresses a protein Oy1 in the second plant. When the second nucleotide sequence exists in the second plant in a heterozygous state, it affects whether the plant color of the second plant is yellow; if the second nucleotide sequence is contained, the plant color is yellow, otherwise, the plant color is not yellow.

In another embodiment of the present invention, the above-mentioned gene for controlling plant wilting degree is the Wi2 gene in the examples of the present invention; the above-mentioned Wi2 gene expresses a protein Wi2 in the second plant. When the second nucleotide sequence exists in a heterozygous state in the second plant, it affects whether the plant of the second plant will wilt; if the second nucleotide sequence is contained, the plant will wilt, otherwise, the plant will not wilt.

The above-mentioned protein LC is as follows a) or b):
  a) a protein consisting of amino acid residues shown in SEQ ID NO: 5;
  b) a protein with the same function as SEQ ID NO: 5 after substitution and/or deletion and/or addition of one or several amino acid residues in SEQ ID NO: 5;
or, the protein Oy1 is as follows a) or b):
  a) a protein consisting of amino acid residues shown in SEQ ID NO: 7;
  b) a protein with the same function as SEQ ID NO: 7 after substitution and/or deletion and/or addition of one or several amino acid residues in SEQ ID NO: 7;
or, the protein Wi2 is as follows a) or b):
  a) a protein consisting of amino acid residues shown in SEQ ID NO: 9;
  b) a protein with the same function as SEQ ID NO: 9 after substitution and/or deletion and/or addition of one or several amino acid residues in SEQ ID NO: 9.

The gene Lc is a DNA molecule shown in 1) or 2) or 3) as follows:
  1) a DNA molecule with a coding region comprising SEQ ID NO: 4;
  2) a DNA molecule with a coding region of SEQ ID NO: 4;
  3) a DNA molecule with the same function as 1) or 2) after substitution and/or deletion and/or addition of one or several nucleotides in 1) or 2).

The gene Oy1 is a DNA molecule shown in 1) or 2) or 3) as follows:
  1) a DNA molecule with a coding region comprising SEQ ID NO: 6;
  2) a DNA molecule with a coding region of SEQ ID NO: 6;
  3) a DNA molecule with the same function as 1) or 2) after substitution and/or deletion and/or addition of one or several nucleotides in 1) or 2).

The gene Wi2 is a DNA molecule shown in 1) or 2) or 3) as follows:
  1) a DNA molecule with a coding region comprising SEQ ID NO: 8;
  2) a DNA molecule with a coding region of SEQ ID NO: 8;
  3) a DNA molecule with the same function as 1) or 2) after substitution and/or deletion and/or addition of one or several nucleotides in 1) or 2).

The present invention relates to nucleotide sequences for controlling male fertility, controlling plant or seed color, and controlling plant wilting, and a method for expanding propagation of a male sterility plant by using these nucleotide sequences and transgenic technology.

The above-mentioned method of the present invention can be used for the following objects.

One object is to provide an efficient seed marking method, which can be used for expanding propagation of male sterility seeds of plants, so as to save manpower for hybrid seed production, reduce costs, and ensure seed purity.

Another object is to provide a method for efficiently distinguishing fertile seeds from sterile seeds according to plant or seed color, or plant wilting degree.

Another object is to provide a transgenic plant, which can maintain the sterility of a male sterility line plant.

Another object of the present invention is to provide a DNA construct.

The construct provided by the present invention is the construct described in the above method.

The above-mentioned DNA construct can restore the fertility of a male sterile mutant, and at the same time change plant color or change plant seed color or change plant wilting degree.

The construct described in the above method is as follows.

In the present invention, a plant expression vector containing the Ms45 gene expression element shown in SEQ ID NO: 3 is constructed, and when the vector is transferred into a male sterility mutant ms45, the fertility of the mutant can be restored.

In the present invention, a vector comprises Lc gene (Ludwig et al., 1993) for controlling a maize anthocyanin synthesis is constructed. This vector affects anthocyanin synthesis, and the overexpression of this gene makes plants or seeds appear purple.

In the present invention, a vector comprises Oy1 gene for regulating chloroplast synthesis is constructed. This vector affects chloroplast synthesis, and the overexpression of this gene makes the plant yellow.

In the present invention, a vector comprises Wi2 gene for regulating and controlling root suberin synthesis is constructed. This vector affects water transport, and the overexpression of this gene causes plants to wilt (the top leaves are wilting).

The third object of the present invention is to provide any of the following substances.

The following substances are provided by the present invention:
  1) a plant, in which the plant is the second plant described in the above method;
  2) a tissue culture of a regenerative cell produced by the plant described in 1);
  3) a protoplast produced from the tissue culture described in 2);

4) a plant, in which the plant is a homozygous recessive male sterility line plant produced by the above method.

The above-mentioned second plant can maintain the sterility of a male sterility line plant.

The above-mentioned plant may be all or part, such as root, stem, leaf, embryo, root tip, pollen or anther of the plant.

The use of the homozygous recessive male sterility line plant produced by the above method in the production of hybrids is also within the protection scope of the present invention.

A key of the present invention is to construct a male restoring gene Ms45 and a gene for controlling plant morphology such as controlling plant color or controlling seed color or controlling plant wilting into one vector, and the vector can restore the fertility of the male sterile mutant ms45, and at the same time, make the plant containing the transgenic sequence to be the desired color or the desired state of plant wilting, that is, mark the plant or seed containing the restoring gene so as to distinguish fertile individuals (maintainer line) and sterile individuals (sterile line).

Taking Lc as an example, in one example of the present invention, by using a nucleotide sequence capable of controlling plant male fertility and overexpression of anthocyanin synthesis-related gene Lc as well as transgenic technology, the present inventors invented a novel method for highly efficient expansion of male sterility line plant. The gene capable of controlling plant male fertility comprises the male sterility genes listed in Table 1 and other male sterility genes, as well as the male sterility genes of other species. The present inventors first constructed a plant transformation vector that contained an expression element for restoring male fertility gene and an expression element for overexpression of anthocyanin synthesis-related gene Lc, and transferred the vector into HiIIA×HiIIB maize hybrids, and under normal conditions, the plants of hybrids were green. The male sterility line plants were then used to backcross the obtained transgenic plants, so that the nucleotide sequence with the Ms45 restoring gene for controlling the plant male fertility and the gene for controlling plant or seed color (Lc gene) was transformed into the male sterility line plant ms45. Due to the presence of the restoring gene Ms45, the transgenic plants appeared to be fertile. When the transgenic heterozygous plant (Msmsms) was crossed with the male sterility line plant (msms), the following two offsprings were produced, one was a male sterile individual with a green plant and a yellow seed (sterile line, the genotype was msms), a male sterile normal seed without the transgenic sequence (sterile line ms45ms45), this sterile line could be restored to be fertile by any wild-type plant, and could be used as a sterile line during seed production; and the other one was a fertile seed of a purple plant or seed (maintainer line, the genotype was Msmsms), the maintainer line was recessively homozygous at the male fertility control site, due to it contained complementary transgenic sequence, the plant appeared to be fertile, and due to it simultaneously contained the nucleotide sequence (anthocyanin synthesis gene) that controlled the color of the plant or seed, the plant or seed was different from the wild type in color.

Taking Oy1 as an example, in one example of the present invention, by using a nucleotide sequence capable of controlling plant male fertility and overexpression of chloroplast synthesis-related gene Oy1 as well as transgenic technology, the present inventors invented a novel method for highly efficient expansion of males sterility line plant. The gene capable of controlling plant male fertility comprises the male sterility genes listed in Table 1 and other male sterility genes, as well as the male sterility genes of other species. The present inventors first constructed a plant transformation vector that contained an expression element for restoring male fertility gene and an expression element for overexpression of chloroplast synthesis-related gene Oy1, and transferred the vector into HiIIA×HiIIB maize hybrids, and under normal conditions, the plants of hybrids were green. The male sterility line plants were then used to backcross the obtained transgenic plants, so that the nucleotide sequence with the Ms45 restoring gene for controlling the plant male fertility and the gene for controlling plant color (Oy1 gene) was transformed into the male sterility line plant ms45. Due to the presence of the restoring gene Ms45, the transgenic plants appeared to be fertile. When the transgenic heterozygous plant (Msmsms) was crossed with the male sterility line plant (msms), the following two offsprings were produced, one was a male sterile individual with a green plant (sterile line, the genotype was msms), a male sterile normal seed without the transgenic sequence (sterile line ms45ms45), this sterile line could be restored to be fertile by any wild-type plant, and could be used as a sterile line during seed production; and the other one was a fertile seed of a yellow plant (maintainer line, the genotype was Msmsms), the maintainer line was recessively homozygous at the male fertility control site, due to it contained complementary transgenic sequence, the plant appeared to be fertile, and due to it simultaneously contained the nucleotide sequence (chloroplast synthesis-related gene) that controlled the color of the plant or seed, the plant was different from the wild type in color.

Taking Wi2 as an example, in one example of the present invention, by using a nucleotide sequence capable of controlling plant male fertility and controlling overexpression of root suberin synthesis-related gene Wi2 as well as transgenic technology, the present inventors invented a novel method for highly efficient expansion of males sterility line plant. The gene capable of controlling plant male fertility comprises the male sterility genes listed in Table 1 and other male sterility genes, as well as the male sterility genes of other species. The present inventors first constructed a plant transformation vector that contained an expression element for restoring male fertility gene and an expression element for overexpression of root suberin synthesis-related gene Wi2, and transferred the vector into HiIIA×HiIIB maize hybrids, and under normal conditions of hybrids, the plants were not in a wilting state. The male sterility line plants were then used to backcross the obtained transgenic plants, so that the nucleotide sequence with the Ms45 restoring gene for controlling the plant male fertility and the gene for controlling root suberin (Wi2 gene) was transformed into the male sterility line plant ms45. Due to the presence of the restoring gene Ms45, the transgenic plants appeared to be fertile. When the transgenic heterozygous plant (Msmsms) was crossed with the male sterility line plant (msms), the following two offsprings were produced, one was a male sterile individual (sterile line, the genotype was msms) that was not in a wilting state (in a wilting state lower than the maintainer line), a male sterile normal seed without the transgenic sequence (sterile line ms45ms45), this sterile line could be restored to be fertile by any wild-type plant, and could be used as a sterile line during seed production; and the other one was a fertile seed of a plant with wilting leaves (maintainer line, the genotype was Msmsms), the maintainer line was recessively homozygous at the male fertility control site, due to it contained complementary transgenic sequence, the plant appeared to be fertile, and due to it simultaneously contained the nucleotide sequence (root suberin synthesis-related gene) that controlled the wilting state of the plant, the plant was different from the wild type in the wilting degree.

Other objects of the present invention will be apparent in the following description and claims.

The experiments of the present invention proves that the method provided by the present invention can expand nuclear male sterile seeds and bring convenience to hybrid seed production. The system mainly uses a nucleotide sequence that can affect plant or seed color or regulate plant wilting, and a wild-type allele of a nuclear male sterility gene as well as transgenic technology. The transgenic seeds can be distinguished by color, and transgenic plants can be distinguished by plant color, or can be distinguished by the wilting degree.

Beneficial Effect

The present application provides a method for expanding propagation of male sterility line plants, and maintainer line plants for expanding propagation of male sterility line plants. After the maintainer line plants provided in the present application are crossed with the male sterility line plants, the offsprings of the male sterility line plants and the maintainer line plants can be harvested at the same time and effectively distinguished. Therefore, the method and maintainer line plants provided by the present application can realize the efficient expansion of male sterility line plants and improve the breeding efficiency. In addition, through the combined use of seed external traits and plant external traits, the method provided in the present application can screen the hybrid offsprings two or more times, which further improves the offspring purity of the male sterility line plants and the offspring purity of the maintainer line plants, respectively, and improves the breeding efficiency and the quality and purity of the hybrid seeds produced.

In the past technology, only seeds or only plants are marked and screened. However, these methods have the following shortcomings: (1) when only seeds are screened, due to heterofertilization and other reasons, in some of seeds obtained by endosperm phenotype screening, the endosperm does not contain transgenic components, but the embryo contains transgenic components, thus the plants developed from these seeds are fertile, and these fertile seeds are difficult to distinguish from sterile seeds, and they can only be distinguished until the plants disperse pollen, but removing fertile plants when dispersing pollen will affect the purity of the propagated hybrids, so that it cannot fully meet the actual production needs; (2) when only plants are screened, the sterile seeds cannot be separated from the fertile seeds during planting, which consumes a lot of manpower and material resources. The method of the present application combines the marking and screening of seeds and plants, and can distinguish sterile plants from fertile plants after sowing and before dispersing pollen (for example, during seedling stage), and the fertile plants can be removed in time, which significantly improves the breeding efficiency and the quality and purity of the hybrid seeds produced.

Sequence Information

The information of the sequences involved in the present application is shown in Table 2 below.

TABLE 2

Sequence information

| SEQ ID NO: | Sequence description | Sequence information |
|---|---|---|
| 1 | Ms45 gene | ATGGAGAAGAGGAACCTGCAGTGGCGGCGAGGGCGTGATGGCATCG TGCAGTACCCTCACCTCTTCTTCGCGGCCCTGGCGCTGGCCCTCCTAG TCGCGGACCCGTTCGGCCTCAGTCCGCTGGCCGAGGTCGACTACCGG CCGGTGAAGCACGAGCTCGCGCCGTACGGGGAGGTCATGGGCAGCTG GCCCAGAGACAATGCCAGCCGGCTCAGGCGCGGGAGGCTGGAGTTCG TCGGCGAGGTGTTCGGGCCGGAGTCTATCGAGTTCGATCTCCAGGGC CGCGGGCCGTACGCCGGCCTCGCCGACGGCCGCGTCGTCGGTGGAT GGGCGAGGAGGCCGGGTGGGAGACGTTCGCCGTCATGAATCCTGACT GGTCAGAAGAAGTCTGTGCCAATGGAGTGAACTCAACGACGAGGAA GCAGCACGAGAAGGAGGAGTTCTGCGGCCGGCCGCTCGGCCTGAGGT TCCACGGGGAGACCGGCGAGCTCTACGTCGCCGACGCGTACTACGGT CTCATGGTCGTTGGCCAGAGCGGCGGCGTGGCGTCCTCCGTCGCGAG GGAAGCCGACGGGGACCCCATCCGGTTCGCGAACGACCTCGATGTGC ACAGGAATGGATCCGTATTCTTCACTGACACGAGCATGAGATACAGC AGAAAGGACCATCTGAACATCCTGTTAGAAGGAGAAGGCACCGGGA GGCTGCTCAGGTATGATCCAGAAACAAGCGGTGTCCATGTCGTGCTC AAGGGGCTGGTGTTCCCAAACGGCGTGCAGATCTCAGAGGACCATCA GTTTCTTCTCTTCTCCGAGACAACAAACTGCAGGATAATGAGGTACTG GCTGGAAGGCCCAAGAGCGGGCGAGGTAGAaGTGTTCGCGAACCTGC CGGGCTTCCCCGACAACGTGCGCTCCAACGGCAGGGGCCAGTTCTGG GTGGCGATCGACTGCTGCCGGACGCCGGCGCAGGAGGTGTTCGCCAA GAGGCCGTGGCTCCGGACCCTGTACTTCAAGTTCCCGCTGTCGCTCAA GGTGCTCACTTGGAAGGCCGCCAGGAGGATGCACACGGTGCTCGCGC TCCTCGACGGCGAAGGGCGCGTCGTGGAGGTGCTCGAGGACCGGGC CACGAGGTGATGAAGCTGGTGAGCGAGGTGCGGGAGGTGGGCCGCA AGCTGTGGATCGGAACCGTGGCGCACAACCACATCGCCACCATCCCC TACCCTTTAGAGGACTAA |
| 2 | Ms45 protein | MEKRNLQWRRGRDGIVQYPHLFFAALALALLVADPFGLSPLAEVDYRPV KHELAPYGEVMGSWPRDNASRLRRGRLEFVGEVFGPESIEFDLQGRGPY AGLADGRVVRWMGEEAGWETFAVMNPDWSEEVCANGVNSTTRKQHE KEEFCGRPLGLRFHGETGELYVADAYYGLMVVGQSGGVASSVAREADG DPIRFANDLDVHRNGSVFFTDTSMRYSRKDHLNILLEGEGTGRLLRYDPE TSGVHVVLKGLVFPNGVQISEDHQFLLFSETTNCRIMRYWLEGPRAGEV EVFANLPGFPDNVRSNGRGQFWVAIDCCRTPAQEVFAKRPWLRTLYFKF |

TABLE 2-continued

Sequence information

| SEQ ID NO: | Sequence description | Sequence information |
|---|---|---|
| | | PLSLKVLTWKAARRMHTVLALLDGEGRVVEVLEDRGHEVMKLVSEVRE VGRKLWIGTVAHNHIATIPYPLED |
| 3 | Promoter and coding region of Ms45 gene | TGCTGAGTTCTCCTTGGGTTATCCATGGTGTCTCTATGAAAAAGATGA GTACAATGTGTCTATATCCGTTTTCTTAGGGTCCCTTCTTCTGCCTTAT TACTGACTGAATCGGGGTTACAAAAAAACTTCCACGGGTGCATGATC TCCATGTTCCACTTCTCCCACCTCGCGTTGCACATTTCTTGGATGTCGG TGGTTCCCATCTGACCGAGGCCCATCAGACACCTTTCGGGACACCCAT CAAGGGCCTTTCGGATGGCCCACGAGACGTATCGGGTCGTGGTGATC CAGGGGATATATGTCCCCCACAATCGTCACCTATATTATTATTCTTTA GATATTATTTAATTTTTGGAAAAATAACAAACTTATACTTTTGTGTAG GGCCTCAGCATAGATTTTCGCTTAGGGCCCAGAAATGCGAGGACCAG CCATGTCTAGTGTCCACTATTGGCACTACCCAGAACAAGATTTAAAAA AATAACCAAAGTAACTAATCCACTCGAAAGCTATCATGTAATGTTTA AAGAAACATCTATTAAAACCACGATCCTCTTAAAAAACAAGCATATT TCGAAAGAGACAAATTATGTTACAGTTTACAAACATCTAAGAGCGAC AAATTATATCGAAAGGTAAGCTATGACGTTCAGATTTTTCTTTTTCATT CTTGTTATTTTGTTATTGTTTTTATATACATTTTCTTCTCTTACAATAGA GTGATTTTCTTCCGATTTTATAAAATGACTATAAAGTCATTTTTATATA AGAGCACGCATGTCGTAGATTCTCGTTCAAAAATCTTTCTGATTTTTTT AAGAGCTAGTTTGGCAACCCTGTTTCTTTCAAAGAATTTTGATTTTTTC AAAAAAAATTAGTTTATTTTCTCTTTATAAAATAGAAAACACTTAGAA AAATAGAGTTGCCAGACTAGCCCTAGAATGTTTTCCCAATAAATTACA ATCACTGTGTATAATTATTTGGCCAGCCCCATAAATTATTTAAACCGA AACTGAAATCGAGCGAAACCAAATCTGAGCTATTTCTCTAGATTAGT AAAAAGGGAGAGAGAGAGGAAGAAATCAGTTTTAAGTCATTGTCCCT GAGATGTGCGGTTTGGCAACGATAGCCACCGTAATCATAGCTCATAG GTGCCTACGTCAGGTTCGGCAGCTCTCGTGTCATCTCACATGGCATAC TACATGCTTGTTCAACCGTTCGTCTTGTTCCATCGTCCAAGCCTTGCCT ATTCTGAACCAAGAGGATACCTACTCCCAAACAATCCATCTTACTCAT GCAACTTCCATGCAAACACGCACATATGTTTCCTGAACCAATCCATTA AAGATCACAACAGCTAGCGTTCTCCCGCTAGCTTCCCTCTCTCCTCTG CCGATCTTTTTCGTCCACCAGCATGGAGAAGAGGAACCTGCAGTGGC GGCGAGGGCGTGATGGCATCGTGCAGTACCCTCACCTCTTCTTCGCGG CCCTGGCGCTGGCCCTCCTAGTCGCGGACCCGTTCGGCCTCAGTCCGC TGGCCGAGGTCGACTACCGGCCGGTGAAGCACGAGCTCGCGCCGTAC GGGGAGGTCATGGGCAGCTGGCCCAGAGACAATGCCAGCCGGCTCAG GCGCGGGAGGCTGGAGTTCGTCGGCGAGGTGTTCGGGCCGGAGTCTA TCGAGTTCGATCTCCAGGGCCGCGGGCCGTACGCCGGCCTCGCCGAC GGCCGCGTCGTGCGGTGGATGGGCGAGGAGGCCGGGTGGGAGACGTT CGCCGTCATGAATCCTGACTGGTAAGTGCTCGATATCGCTCCGGCGTC CACTCGTTACATGCTATAATATAGTAGTACTAAGATATTTTGATCTGA TTTTTTGCATTCTTGGGAGAAACGTCATGCAAATTTGTTGTTTCTTGG CAAAGGTCAGAAGAAGTCTGTGCCAATGGAGTGAACTCAACGACGAG GAAGCAGCACGAGAAGGAGGAGTTCTGCGGCCGGCCGCTCGGCCTGA GGTTCCACGGGGAGACCGGCGAGCTCTACGTCGCCGACGCGTACTAC GGTCTCATGGTCGTTGGCCAGAGCGGCGGCGTGGCGTCCTCCGTCGC GAGGGAAGCCGACGGGGACCCCATCCGGTTCGCGAACGACCTCGATG TGCACAGGAATGGATCCGTATTCTTCACTGACACGAGCATGAGATAC AGCAGAAAGTGAGCAAAGCGACGTAACAATCCGGCTTCTCATTTTCA AACGCCTCTGTATTCTCTGCTGAAAGAGTAGCTCACCAGACAAGAGC TGAATTTGCAGGGACCATCTGAACATCCTGTTAGAAGGAGAAGGCAC CGGGAGGCTGCTCAGGTATGATCCAGAAACAAGCGGTGTCCATGTCG TGCTCAAGGGGCTGGTGTTCCCAAACGGCGTGCAGATCTCAGAGGAC CATCAGTTTCTTCTCTTCTCCGAGACAACAAACTGCAGGTAACAAAAA TACTATCTGACGATGCTCATGATTCTACCGTATCCATAGTCATGAACA CAAACCACACGAATCTGGCCTTGACCAGGATAATGAGGTACTGGCTG GAAGGCCCAAGAGCGGGCGAGGTAGAAGTGTTCGCGAACCTGCCGG GCTTCCCCGACAACGTGCGCTCCAACGGCAGGGGCCAGTTCTGGGTG GCGATCGACTGCTGCCGGACGCCGGCGCAGGAGGTGTTCGCCAAGAG GCCGTGGCTCCGGACCCGTACTTCAAGTTCCCGCTGTCGCTCAAGGT GCTCACTTGGAAGGCCGCCAGGAGGATGCACACGGTGCTCGCGCTCC TCGACGGCGAAGGGCGCGTCGTGGAGGTGCTCGAGGACCGGGCCAC GAGGTGATGAAGCTGGTGAGCGAGGTGCGGGAGGTGGGCCGCAAGC TGTGGATCGGAACCGTGGCGCACAACCACATCGCCACCATCCCCTAC CCTTTAGAGGACTAACCATGATCTATGCTGTTTCAATGCCTCCTAATC TGTGTACGTCTATAAATGTCTAATGCAGTCACTGGTTGTAATCTTGTTT GTGTTTGGCAAATTGGCATAATAATGGACAGATTCAATGGGCATTGGT GCTGTAGTCGCATCACACTAATTGAATGGGATCATGTTGAGCTCTCAC TTTGCTACAATTTGCTCCAGCTTGTACGGTTGTACCCTCTTGCTCGTCT ATAGTAAGGGCCATCTAAAAAAAACTCAAATTAGATCTGCAATACAA GTATGATTGGGCCGAATTTGGATTGTCACGGGTCCGCGACCGCGAATT GGGCTCGGTTTGATTTAGCCGACATAGTAGTGACCGACCCGAGCCGG CGGCGAGCCAAACCGAGCGGACGCCGCCATGGATCGCGAGTGGGCT CCAAGCCCGGCAGCGGCGGCGCCGCCTCCGCGCAGAATGAGGCCATC |

TABLE 2-continued

Sequence information

| SEQ ID NO: | Sequence description | Sequence information |
|---|---|---|
|  |  | GACCGGCGGGAGCGCCTCCGCCGCCTGGCCCTCGAGACCATCGACCT<br>CGCCAAGGACCCCTATTTCATGCGCAACC |
| 4 | Lc gene | ATGGCGCTTTCAGCTTCCCGAGTTCAGCAGGCGGAAGAACTGCTGCA<br>ACGACCTGCTGAGAGGCAGCTGATGAGGAGCCAGCTTGCTGCAGCCG<br>CCAGGAGCATCAACTGGAGCTACGCCCTCTTCTGGTCCATTTCAGACA<br>CTCAACCAGGGGTGCTGACGTGGACGGACGGGTTCTACAACGGCGAG<br>GTGAAGACGCGGAAGATCTCCAACTCCGTGGAGCTGACATCCGACCA<br>GCTCGTCATGCAGAGGAGCGACCAGCTCCGGGAGCTCTACGAGGCCC<br>TCCTGTCGGGCGAGGGCGACCGCCGCGCTGCGCCTGCGCGGCCGGCC<br>GGCTCTCTGTCGCCGGAGGACCTCGGCGACACCGAGTGGTACTACGT<br>GGTCTCCATGACCTACGCCTTCCGGCCAGGCCAAGGGTTGCCCGGCA<br>GGAGTTTCGCGAGCGACGAGCATGTCTGGCTGTGCAACGCGCACCTC<br>GCCGGCAGCAAAGCCTTCCCCGCGCGCTCCTGGCCAAGAGCGCGTC<br>CATTCAGTCAATCCTCTGCATCCCGGTTATGGGCGGCGTGCTTGAGCT<br>TGGTACAACTGACACGGTGCCGGAGGCCCCGGACTTGGTCAGCCGAG<br>CAACCGCGGCTTTCTGGGAGCCGCAGTGCCCGAGCTCCAGCCCGTCA<br>GGACGAGCAAACGAGACCGGCGAGGCCGCAGCAGACGACGGCACGT<br>TTGCGTTCGAGGAACTCGACCACAATAATGGCATGGACGACATAGAG<br>GCGATGACCGCCGCCGGGGGACACGGGCAGGAGGAGGAGCTAAGAC<br>TAAGAGAAGCCGAGGCCCTGTCAGACGACGCAAGCCTGGAGCACATC<br>ACCAAGGAGATCGAGGAGTTCTACAGCCTCTGCGACGAAATGGACCT<br>GCAGGCGCTACCACTACCGCTAGAGGACGGCTGGACCGTGGACGCGT<br>CCAATTTCGAGGTCCCCTGCTCTTCCCCGCAGCCAGCGCCGCCTCCGG<br>TGGACAGGGCTACCGCTAACGTCGCCGCCGACGCCTCAAGGGCACCC<br>GTCTACGGCTCTCGCGCGACGAGTTTCATGGCTTGGACGAGGTCCTCG<br>CAGCAGTCGTCGTGCTCCGACGACGCGGCGCCCGCAGCAGTAGTGCC<br>GGCCATCGAGGAGCCGCAGAGATTGCTGAAGAAAGTGGTGGCCGGC<br>GGCGGTGCTTGGGAGAGCTGTGGCGGCGCGACGGGAGCAGCACAGG<br>AAATGAGTGGCACTGGCACCAAGAACCACGTCATGTCGGAGCGAAAG<br>CGACGAGAGAAGCTCAACGAGATGTTCCTCGTCCTCAAGTCACTGCTT<br>CCGTCCATTCACAGGGTGAACAAAGCGTCGATCCTCGCCGAAACGAT<br>AGCCTACCTCAAGGAGCTTCAGAGAAGGGTGCAAGAGCTGGAGTCCA<br>GTAGGGAACCTGCGTCGCGCCCATCCGAAACGACGACAAGGCTAATA<br>ACAAGGCCCTCCCGTGGCAATAATGAGAGTGTGAGGAAGGAGGTCTG<br>CGCGGGCTCCAAGAGGAAGAGCCCAGAGCTCGGCAGAGACGACGTG<br>GAGCGCCCCCCGGTCCTCACCATGGACGCCGGCACCAGCAACGTCAC<br>CGTCACCGTCTCGGACAAGGACGTGCTCCTGGAGGTGCAGTGCCGGT<br>GGGAGGAGCTCCTGATGACGCGAGTGTTCGACGCCATCAAGAGCCTC<br>CATTTGGACGTCCTCTCGGTTCAGGCTTCAGCGCCAGATGGCTTCATG<br>GGGCTTAAGATACGAGCTCAGTTTGCTGGCTCCGGTGCCGTCGTGCCC<br>TGGATGATCAGCGAGGCTCTTCGCAAAGCTATAGGGAAGCGGTGA |
| 5 | Lc protein | MALSASRVQQAEELLQRPAERQLMRSQLAAAARSINWSYALFWSISDTQ<br>PGVLTWTDGFYNGEVKTRKISNSVELTSDQLVMQRSDQLRELYEALLSG<br>EGDRRAAPARPAGSLSPEDLGDTEWYYVVSMTYAFRPGQGLPGRSFASD<br>EHVWLCNAHLAGSKAFPRALLAKSASIQSILCIPVMGGVLELGTTDTVPE<br>APDLVSRATAAFWEPQCPSSSPSGRANETGEAAADDGTFAFEELDHNNG<br>MDDIEAMTAAGGHGQEEELRLREAEALSDDASLEHITKEIEEFYSLCDEM<br>DLQALPLPLEDGWTVDASNFEVPCSSPQPAPPPVDRATANVAADASRAP<br>VYGSRATSFMAWTRSSQQSSCSDDAAPAAVVPAIEEPQRLLKKVVAGGG<br>AWESCGGATGEAAQEMSGTGTKNHVMSERKRREKLNEMFLVLKSLLPSI<br>HRVNKASILAETIAYLKELQRRVQELESSREPASRPSETTTRLITRPSRGNN<br>ESVRKEVCAGSKRKSPELGRDDVERPPVLTMDAGTSNVTVTVSDKDVLL<br>EVQCRWEELLMTRVFDAIKSLHLDVLSVQASAPDGFMGLKIRAQFAGSG<br>AVVPWMISEALRKAIGKR |
| 6 | Oy1 gene | GAAAAAGTGTTAAGAAATCAACATGTTGTCATATCGGGCTCACAA<br>CGTATCATTCTCCATTGACAGACCATGAAGAAATGAGCACAGGAAAC<br>TTTAAGATTCAATGCCTTCGATGAATAGGCATTAGAAAAAAAAGTT<br>GGAAGATAAAACTAGCTAACTGAAACATGTGTGAAGATACTGAAGGC<br>TCTGAAATTGATAAACCTACATTTTCCAGGGACAAAAACATGAGTAA<br>ATGGAGCATGGCATGGCAGCTTTAATCTGTATGCACAAAACATTCAA<br>GTGATTAAGCAGTAAATAAGGTTGCTAACAAAATTAGCTCAGAAGC<br>TAGTACAATTGAGCATAAAAGCAATAGCTAACTTCCATAGATAAAG<br>ATAGGCTAGAACCAGAAATATAATCTTATTAACACATTAAGTCATAG<br>TCCTAATAATGAGAGAAATATTTGCCAAATTCTGAAATGCAACAAAC<br>AGACATGTCGTTTCACTGATACAAAAGTACTGAGACGGTGAGACCCC<br>AAGCTAATTTTGTAGCTACCTCGAGATTTCAAAAACCTGTTCGCCTTC<br>CTGTTATCACATGAAATCATGCTAAATTACACTTCACTTACTGTACGT<br>AACACTTAGGAGCTGTTTGGTTCCTTTAGTGACTAAACTTTAGTCCCT<br>AGAAATCCTATTTAAAATACCTATTTAGTCACCCATTGGTATTTTAG<br>GAACTAAAAGTGACTAAATTTTAGTCACCCCATTTAGTATTTTAGGGA<br>CTAAAAGTGAAAAGTTTAGTAGGTGGGTACCAAACACCTCCTAAAGT<br>TTAGTCACTAAAGTTTAGGAGGGTGACTAAAGGAACCAAACACCCCC |

TABLE 2-continued

Sequence information

| SEQ ID NO: | Sequence description | Sequence information |
|---|---|---|
| | | TTAGTCCCTAGAAATCCTATTTGAAAGACATATTTTAATCACTTTGTTT
AGGCCCGTTTGGTTCCTTTAGTCAATTGACTAAACTTAAGTGATTAAA
GTTTAGTCACTAAAGTACACAGTTTTGTTCCAGTGACTAAACCTAACT
AAAAAGCATTAATTTAGTGCGAATAATGACTGCATTACCCCTATTAAC
TAGTGGATGTCTGTTGCACTAAGAAAGAGGAGAAGTCAAATGAGGTA
AAAATCCTACTTTAGTCCATTTTAGTCACCCCCTTGGTGACTAAAGAA
CTTAAGTTTAGTCACCCCACTTTAGTCACCATGTTTGCTTCTTTAGGGA
CTAAGGATGCGTTTGGTTGCGGGACAGCTGGTGACAGGCAGGACAGA
GATGTCCCCAGGCGTCCTCTCTCGTCCCTCTAATTTTGAGGGACAACT
AGGGACAACACTGGGATAATCCTGTCCCAACCCCTGACCCTGAACCA
AACAACCTTATTTAAGGGACATCCTATCTCATCCCGTTCTGTCATTAC
AACCAAACGCATCCTAAAAGTGGTGAAAGGGCCTCTAACGTAATGGT
TAAGGCTTCCGAGTAGCACCTCCAGGTTCCGGGTTCGATCCTCCTCGG
GGACGAATTTTAGACTTGGTTAAAAAAATCCCCTCGCTGTGCCCCACC
CGCTACCGGGTTACGTCCTACGCGTCACCCTCCGACTGGACCGTTGCA
GAGTGAGCGGTGATGGCCCGCTAGTGATAGGGGGCCAAGGCAGGGG
CGAAGCCAGCATTTGAGATTGAGAGGGACAAATTAGATTGAGGGGGG
CTGTTAAGAGGTATTTTACATTATTTATATGGTGATTAGCTAAAAAAA
TTAATAGCTTCTATGGAATTTGTAGAAGATTAGGGGGGACATTGCCCC
CCTGTGCCCCTCCCTAGAATCGCCCCTGGGCCAAGGTTCGGGGATTTT
CTCGGTCAGGACCATGTTTCGGCCTCTTCTTAATATAATACCAGGAGG
GCTGTCTTTCCCTCCCCGGTCGAGTTTTTAGGGACTAAAAGTGGCTAT
TTTAGCCACCCCAAACCAAATGAGGCCTTAGTATTTTAGTGACTCGAT
AAAGTTTAGGAGATGAGAACCAAACACCACCTTAGCTTCATATCAAT
TAATTGCCTCTTTCATCAACAAGAAACAATGCGTATTTTAAAAAAAAT
TTGCCAACATGCCAACCCTTATATGGACACTTACAAGCAGGCACTAG
ATACCTTAAACTTTTCGCAAGGCAAATGTACTCCATCCTCTACCACTA
CATGTCCCTCAACTGTCTCAAACAACCAAATATTGGTACAAAGATTGC
ACAAGGTCAATACTATGGCTTAAAATACCTAGAGATTCAAACTGATG
CACAAGATAATAATTTAGCATAATACTCCCTTCGTCTCAAATAATAGT
CGTTTTAGCTCTAGATTTTTATGTCCATATTCATATGAATGATTATGAA
CCTAAACATATATATAACCCATACATTAATTATTGTATGCATACAGTA
AATGGTAAAACGAATTTTAATTTGGGACCGAGGAAATACTTCCGAA
GTTATGCTCTAATGCAGCCAAATGCTACAACACTGATTTACAAGGAA
GACTGAAATGCAAAGAGCATTATGATGCTCATAACATGCATTCCAAA
TGGAAGGAATGGATCCTACATTATTATGATGCTAGATGCACAAAATT
GATACCAATTCAAGCTCCAGATATTATTAAACAGCAGAACATTATGA
AAGTAACAGAACAAGAGGGTTCCCGCCAAAAATTGTGACTAAGGAAC
ATTTACCTCAAGAACAATCTAGCTAAAGACTTCATAAAACTTCTCAAT
GACAAGTAAACCCGAGTCAATGGATTCAAGCGGATCCTTGCGGAGCC
GATGCCTCAAGCAGTTTGGAATGACAGTAGCAATGTCCTCCACGGTG
ACGCTGTCCCTTCCTTTCAACGCAGCCAGCGCCTTGGCAGCCCTGTTA
GTCACAATGTCACCTCTGAGTCCATCAACGTTCAACTCAGAGCACACC
TTGGATATCTTGACACGGAGGTCATGGTCAATCTGCACAGCGCCAAG
GTTACTCCGTGCAGATGATATCTGCTGCTGGAGCTTCTCCTGCTCGTC
ATGATACGACTCACGGAACGTCTTCGGATCCCTGTCGAAACGAGCCC
TCTCCTCCACGATCTTCACCCTGAGCTCGGCGTCCCTGACGGTACCAA
CCTGCGCGTGCATCCCGAACCGGTCCAGCAGCTGGGGCCTGAGCTCC
CCTTCCTCCGGGTTACCAGAGCCGATGAGGATGAAGCGAGCAGGGTG
GGATATGGAGATACCCTTCCTCTCCACCGTGTTCCACCCCGACGCAGC
GGAATCCAGCAGCACGTCGACGAGGTGGTCGTCCAGCAGGTTGACCT
CGTCGACGTACAGTATGCCCCTGTTGGCCTTGGCGAGCAGGCCGGGC
TCGAACGCCTTGACGCCCTCGGTGAGCGCCTTCTCGATGTCAATGGTG
CCGCAGACGCGGTCCTCGGTGGCGCCGAGGGGCAGGTCGACCATGGT
GATCTTGGCGGTGGTGACGGGGAGGCCGGTGTCCCCCTGCAGGACCC
GCTGGCGGACCTCGGGGCCCATGACCTCGGGGTCGTCCGGGTCGGAG
TTGAAGGGGTCGCCGACGACGACGCGGATGTCCGGGAGCAGGTCGAC
GAGGGAGCGGACGGTGGTGGACTTCCCCGTGCCCCTGTCGCCCATGA
TCATGACGCCGCCGATCTTGGGGTCGATGACGTTGAGCAGCAGGCAG
AGCTTCATCTCGTCCTGCCCCACGATGGCCGCGAACGGGTACACGGG
GCGCTGGGTCTCCTTCGCGGCCGACGCCGTCGCCTCCTGCGCGGAAGC
AGAAGCAGGCATCGAAAATGCGGGGTTGCGGAGGAAGGATTACCGA
CCGGTTCCTGCGGGCTGCGGGATTGGAGAACGGGGCGTACCTGTTC
GGCGGCGGTGGGAGCGGCGACATTGCAGACGGTGAATCGGCCGCGG
CGGAAGTCCAGTCCCTTCCTGGATGGTTGAATGCGCCCTGCGAGTGTA
CCGGGGGGCGGTAAGGGGGGGTGTTGGATTCGGCGCTCGCTGATGA
GCGAGCTGGGAAACAGAGTGAGTAGGGGGAGGGAAATGTGAGATGA
CGGTTACCTGAGGAAGCTGAAGCGGCGAGGAAGAGTGGGCGGGAGG
TGGAGCCCGGGAGGAGGGCCCTCGCGGCGGAAGTGGGGGAGAAGGT
GGAAGCCATGACGGGGAGGAGGAAGAAGGGCATGGAGGTTTGT
GTGGAAGGAGCGGGGAGGAGGGGATAGGGGATAAGCCGGGGGAG
GGGGACGGGGCAGCGATCTCGGAGGGATGCTGCGATTGGAGGCTGCC
AACTTCTGGATTGACCGGCCCCGCTTGGCAGTCGGCAGCAAGCAATC
GTTGTTGATGGTAACGGCTTGATGGAGTTGACGATGCTATGCGCTGT
TGCCACTGATTTTAGGGTACGCGAAACGGCTCAAAATGATAGTTTGAT |

TABLE 2-continued

Sequence information

| SEQ ID NO: | Sequence description | Sequence information |
|---|---|---|
| | | ACTATGGCGCTGTGCCCAACATGCTTGCCTTCGTCCTCAGCATGACAG<br>CATCTATCTAGT |
| 7 | Oy1 protein | MPLLPLLPVMASTFSPTSAARALLPGSTSRPLFLAASASSGNRHLTFPSPY<br>SLCFPARSSASAESNTPPYRPPGTLAGRIQPSRKGLDFRRGRFTVCNVAAP<br>TAAEQEATASAAKETQRPVYPFAAIVGQDEMKLCLLLNVIDPKIGGVMI<br>MGDRGTGKSTTVRSLVDLLPDIRVVVGDPFNSDPDDPEVMGPEVRQRVL<br>QGDTGLPVTTAKITMVDLPLGATEDRVCGTIDIEKALTEGVKAFEPGLLA<br>KANRGILYVDEVNLLDDHLVDVLLDSAASGWNTVERKGISISHPARFILI<br>GSGNPEEGELRPQLLDRFGMHAQVGTVRDAELRVKIVEERARFDRDPKT<br>FRESYHDEQEKLQQQISSARSNLGAVQIDHDLRVKISKVCSELNVDGLRG<br>DIVTNRAAKALAALKGRDSVTVEDIATVIPNCLRHRLRKDPLESIDSGLL<br>VIEKFYEVFS |
| 8 | Wi2 gene | GCCCCCGGCCTCCTCCCGCCTCCCAGATCTCGCTCGGCGCCAGTTGCC<br>TCGCAGTTTGGATCATCTCATACCTCGTAAGTCGTAAGGATTTCTGAA<br>CTACGCTCATAACCGAGTTTTCAATCTGTGTTGCGGTCTCGCATTATTT<br>CTGATCTGTTAGCTTGTTTTTTTTCTGTTGCCAAATTCTGGGTTGTTCC<br>CGCGATGTAACCGGAAATGCGATTGGATCCGCTGATTTGCCACTTAG<br>GAATAGGGATGGATTCGGATATTTATTCGGATGTCATTTTTTTTGGTC<br>TTCTTTCTTCGATTGTGAACAATTAACATATAAAATTTGATATGTAAA<br>TTTATATTCTTGTTTTTAGCATTGAGACTATTAATCTTCACAAAAATA<br>AACATTAAATCCATTCTATATCTTTTTAAATAATTCATATAAAATTCG<br>GATGTCTATTCGAATACGGATTCGGATGTTTTTTCACCTTTTTTGTTGT<br>AAGGAGAAAATAATGTACATAAAAAATTATACAAAAATTTATTTAAA<br>TACTTCAGAATATTCTTAATAACATTGCCGAAAATTAACTTTAAATTC<br>TATGTATATCTATGCTAAAATATTAGATTTGTGATACAATTCGGATGT<br>TTTAGGAACATCCCTACCTAGGAATGTCCTGGCCTCTCTCTCTCTCT<br>TGACGAAGGTTATTCGATTGGTTCTGTGATTCTGCGTAGTTGAGTGGG<br>ATCCATAGTGTTTGATTTTGGGGGAATTCAAGTCGTCCTTTAATTGCG<br>AAATGTAACTGTTAGACCCTTAGAGACAGAGAGCTTTGTGGGTTTATTA<br>TCATAACTTAGTGCAGTTTTGAAGTATAAGTTTCAGTACTGAAACTAG<br>ATCCGGAAGAACATACGTCACCGTTTGAACGGTTGGGCTCATGGAAT<br>TATTTGTAATCATGGGGAGACATGTTTGAAGTCTGCTATAATATTGAT<br>GCATTTAGTACTTATCAGTAGGCGATTCAGTGGTTGATGTGTGTGCAA<br>GATGGGTTTGCAAGCCCAGATCTTGTTATGGTTCGCTATGTGATCCGA<br>GTACGAGTTCAGTGATGTTTTAGATCTGAAACTGCAGTGACAATGTGC<br>GCTCGCTCTCTGGTTTAGTTGCAAATGGCTAGAAATACTTGATTTAAT<br>CAACTTGAGGAGTGACTGTGTGCTTGTTGCAGTATCTGTAGCTAATTC<br>CTATGTGCTTCTCTTGTTTGTAGGGCGAATATGAGGGAGATCCTGCAC<br>ATCCAGGGAGGGCAATGTGGCAACCAGATTGGCGCCAAGTTCTGGGA<br>GGTGGTGTGTGATGAGCATGGCATTGACCCTACCGGGCGGTACACTG<br>GCAGTTCCGACCTTCAGTTGGAGCGTGTTAATGTCTACTACAACGAAG<br>TCTCCTGTGGACGCTTTGTTCCCCGCGCTGTTCTCATGGATCTTGAGCC<br>TGGGACAATGGACAGTGTCCGGACTGGACCCTATGGGCAGATCTTCC<br>GCCCTGACAACTTTGTGTTCGGGCAATCTGGTGCTGGTAACAATTGGG<br>CCAAGGGCCACTACACCGAGGGTGCTGAGCTCATTGACTCTGTTCTGG<br>ATGTTGTGAGGAAGGAAGCTGAGAACTGTGACTGCTTGCAAGGTACT<br>TGAGCTTATTGATGATAAAGCTGATTGCTTCAAGTTTTTATATTTGTTT<br>CTGCTGAAGAAACTAGAGTGAGATGTTCATGTTGAAGTATCTCTACA<br>GTTTCTTTACCCATGCTTGTGATTTTTTTTTCACTACAATGCGATACAT<br>TGAATCCATATAGGGCTGAAGCTATCCATGGAACTAGAACTGCGATA<br>TCCTGTTATAATGAAGCTGCTTTTGCTCTAGAACCTAAGTCATTTCACT<br>CGTTTAGTTCATGCCCTATAATATAGAATGGATTATCCTAAATGACAC<br>TGATACTTATTGGTCCTTGCCGACTGCTTAGTATTTTCACATTTGAGTA<br>TCTTTTCTGCTGTTGCCATGTTTTGACACATGAGCAGAAACAAATTTT<br>CTTACTTGCACTTGTTGCTTGAACAATTGGCATACCAAAATACTGTAC<br>ATAAAAAAGCTGTTCAGACTGTGATTACTAAATCACCTATGCGTGTCA<br>TGTACCTTGGTTGCCATCTGTACTTTGCTATGTGTTTTTTTCCAATCA<br>CCCAAGTAACTAAACTTAATTATCATGCATTGAACATTAACTCAATCT<br>ATTTGTTTATTCAGGATTCCAAGTATGCCACTCCCTTGGTGGTGGTAC<br>TGGATCTGGTATGGGTACGCTGTTGATCTCAAAGATCAGGGAGGAGT<br>ACCCTGACCGCATGATGCTGACATTCTCAGTTTTCCCCTCACCGAAAG<br>TATCTGATACCGTGGTTGAGCCATACAATGCCACTCTTTCTGTCCACC<br>AGTTGGTTGAGAATGCTGATGAGTGCATGGTTCTCGATAACGAAGCC<br>CTCTATGACATCTGCTTCAGGACTCTTAAGCTGACCACCCCCAGCTGT<br>AAGCAGCCTCATTCTTTCTTAATTTGATCTGCTCAGCATTGCAGATAT<br>ATGCATGCTCGTACTAGTGTATTTACTGTGTATAGTAACACTGTATTT<br>GTTAATTGCTGCAGTTGGTGATCTGAACCATTTGATCTCTGCAACCAT<br>GAGTGGAGTCACCTGCTGCTAAGGTTCCCTGGTCAGCTGAACTCCGA<br>CCTCAGGAAGCTGGCAGTGAACCTGATCCCCTTCCCCGTCTCCACTT<br>CTTCATGGTCGGCTTCGCGCCGCTGACGTCCCGTGGCTCCCAGCAGTA<br>CCGGGCCCTCACAGTCCTCGAGCTCACGCAGCAGATGTGGGATGCCA<br>AGAACATGATGTGTGCCGCTGACCCTCGCCATGGGCGTTACCTCACCG<br>CCTCTGCCATGTTCCGCGGGAAGATGAGCACCAAGGAGGTCGACGAG |

TABLE 2-continued

Sequence information

| SEQ ID NO: | Sequence description | Sequence information |
|---|---|---|
| | | CAAATGATCAACGTCCAGAACAAGAACTCGTCCTACTTCGTGGAGTG<br>GATCCCCAACAACGTCAAGTCCAGCGTGTGCGACATCCCGCCCAGGG<br>GCCTGTCCATGGCGTCCACCTTCATCGGCAACTCGACCTCCATCCAGG<br>AGATGTTCCGGAGGGTGAGCGAGCAGTTCACTGCCATGTTCAGGAGG<br>AAGGCTTTCTTGCACTGGTACACGGGCGAGGGCATGGACGAGATGGA<br>GTTCACCGAGGCCGAGAGCAACATGAACGACCTCGTGTCGGAGTACC<br>AGCAGTACCAGGACGCGACTGCCGACGAGGAGGAGTACGAGGACGA<br>GGAGGAGGTGCAGGCCGATGACATGTGAGGGGAGGGCTGTTATCGTG<br>TGAAGCCTTGTGGTCCTAGGGCAAGCGGACCTCGATGAGTTCGGTGTT<br>CCCTTTCGTGTTGTTGCCATCTTTCTACTGCTAGCGTACCCACCCTCGT<br>GGCCCATTCCGTCGCTGTTGACGCATGTATTTTTCTTGTGCTATGGAA<br>CCTTGCTTTTGGTACGGTACTACCTTATGCTGCCTGCTAGTATGCTTGG<br>CGTTTGAGGTTCCTGGCTTGAATTTAAGCCT |
| 9 | Wi2 protein | MREILHIQGGQCGNQIGAKFWEVVCDEHGIDPTGRYTGSSDLQLERVNV<br>YYNEASCGRFVPRAVLMDLEPGTMDSVRTGPYGQIFRPDNFVFGQSGAG<br>NNWAKGHYTEGAELIDSVLDVVRKEAENCDCLQGFQVCHSLGGGTGSG<br>MGTLLISKIREEYPDRMMLTFSVFPSPKVSDTVVEPYNATLSVHQLVENA<br>DECMVLDNEALYDICFRTLKLTTPSFGDLNHLISATMSGVTCCLRFPGQL<br>NSDLRKLAVNLIPFPRLHFFMVGFAPLTSRGSQQYRALTVLELTQQMWD<br>AKNMMCAADPRHGRYLTASAMFRGKMSTKEVDEQMINVQNKNSSYFV<br>EWIPNNVKSSVCDIPPRGLSMASTFIGNSTSIQEMFRRVSEQFTAMFRRKA<br>FLHWYTGEGMDEMEFTEAESNMNDLVSEYQQYQDATADEEEYEDEEEV<br>QADDM |
| 10 | Bar gene | ATGAGCCCAGAACGACGCCCGGCCGACATCCGCCGTGCCACCGAGGC<br>GGACATGCCGGCGGTCTGCACCATCGTCAACCACTACATCGAGACAA<br>GCACGGTCAACTTCCGTACCGAGCCGCAGGAACCGCAGGAGTGGACG<br>GACGACCTCGTCCGTCTGCGGGAGCGCTATCCCTGGCTCGTCGCCGAG<br>GTGGACGGCGAGGTCGCCGGCATCGCCTACGCGGGCCCCTGGAAGGC<br>ACGCAACGCCTACGACTGGACGGCCGAGTCGACCGTGTACGTCTCCC<br>CCCGCCACCAGCGGACGGGACTGGGCTCCACGCTCTACACCCACCTG<br>CTGAAGTCCCTGGAGGCACAGGGCTTCAAGAGCGTGGTCGCTGTCAT<br>CGGGCTGCCCAACGACCCGAGCGTGCGCATGCACGAGGCGCTCGGAT<br>ATGCCCCCCGCGGCATGCTGCGGGCGGCCGGCTTCAAGCACGGGAAC<br>TGGCATGACGTGGGTTTCTGGCAGCTGGACTTCAGCCTGCCGGTACCG<br>CCCCGTCCGGTCCTGCCCGTCACCGAGATTTGA |
| 11 | Ms45F | tgaattcTGCTGAGTTCTCCTTGGGTTATCC |
| 12 | Ms45R | tcccgggGGTTGCGCATGAAATAGGGGT |
| 13 | Bar669F | TCTCGGTGACGGGCAGGAC |
| 14 | Bar669R | TGACGCACAATCCCACTATCCTT |
| 15 | Ms45 promoter sequence | TGCTGAGTTCTCCTTGGGTTATCCATGGTGTCTCTATGAAAAAGATGA<br>GTACAATGTGTCTATATCCGTTTTCTTAGGGTCCCTTCTTCTGCCTTAT<br>TACTGACTGAATCGGGGTTACAAAAAACTTCCACGGGTGCATGATCT<br>CCATGTTCCACTTCTCCCACCTCGCGTTGCACATTTCTTGGATGTCGGT<br>GGTTCCCATCTGACCGAGGCCCATCAGACACCTTTCGGGACACCCATC<br>AAGGGCCTTTCGGATGGCCCACGAGACGTATCGGGTCGTGGTGATCC<br>AGGGGATATATGTCCCCCACAATCGTCACCTATATTATTATTCTTTAG<br>ATATTATTTAATTTTTGGAAAAATAACAAACTTATACTTTTGTGTAGG<br>GCCTCAGCATAGATTTTCGCTTAGGGCCCAGAAATGCGAGGACCAGC<br>CATGTCTAGTGTCCACTATTGGCACTACCCAGAACAAGATTTAAAAA<br>AATAACCAAAGTAACTAATCCACTCGAAAGCTATCATGTAATGTTTA<br>AGAAACATCTATTAAAACCACGATCCTCTTAAAAAACAAGCATATT<br>TCGAAAGAGACAAATTATGTTACAGTTTACAAACATCTAAGAGCGAC<br>AAATTATATCGAAAGGTAAGCTATGACGTTCAGATTTTTCTTTTTCATT<br>CTTGTTATTTTGTTATTGTTTTATATACATTTTCTTCTCTTACAATAGA<br>GTGATTTTCTTCCGATTTTATAAAATGACTATAAAGTCATTTTTATATA<br>AGAGCACGCATGTCGTAGATTCTCGTTCAAAAATCTTTCTGATTTTTTT<br>AAGAGCTAGTTTGGCAACCCTGTTTCTTTCAAAGAATTTTGATTTTTTC<br>AAAAAAAATTAGTTTATTTTCTCTTTATAAAATAGAAAACACTTAGAA<br>AAATAGAGTTGCCAGACTAGCCCTAGAATGTTTTCCCAATAAATTACA<br>ATCACTGTGTATAATTATTTGGCCAGCCCCATAAATTATTTAAACCGA<br>AACTGAAATCGAGCGAAACCAAATCTGAGCTATTTCTCTAGATTAGT<br>AAAAAGGGAGAGAGAGGAAGAAATCAGTTTTAAGTCATTGTCCCT<br>GAGATGTGCGGTTTGGCAACGATAGCCACCGTAATCATAGCTCATAG<br>GTGCCTACGTCAGGTTCGGCAGCTCTCGTGTCATCTCACATGGCATAC<br>TACATGCTTGTTCAACCGTTCGTCTTGTTCCATCGTCCAAGCCTTGCCT<br>ATTCTGAACCAAGAGGATACCTACTCCCAAACAATCCATCTTACTCAT<br>GCAACTTCCATGCAAACACGCACA |

TABLE 2-continued

Sequence information

| SEQ ID NO: | Sequence description | Sequence information |
|---|---|---|
| 16 | Ms45F1 | CTTGAGCGACAGCGGGAACT |
| 17 | Ms45R1 | TGTTGTTTCTTGGCAAAGGTCAG |
| 18 | Nucleotides encoding interfering RNA of CWI-2 gene | TAAGTTTCGCTTCGGCGTGCTTGCTGCTGCTGTTGCAGCTCGCAGGAG<br>CGTCGCATGTCGTCTACAACTACAAGGACCTCGAAGCCGAGGCTGCT<br>GCGGCGACGGACCAGGTGCCGCCGTCCATCGTCAACCCCCTGCTCAG<br>GACGGGGTACCACTTCCAGCCCCCCAAGAACTGGATCAATGCGCCCA<br>TGTACTACAAGGGGTGGTACCATTTCTTCTACCAATACAATCCCAAGG<br>GCGCCGTATGGGGCAACATCGTGTGGACTAGTAGAGGGTAATTAAGC<br>AAAACTTATCCAAAACTAAACATTTTACTATTATTTTGACCTTTTTATT<br>CCACTTTTCTTAGACAATGATTTAACCTCGTAATCAATTGTTAGGATTT<br>CTAGTCCACACGATGTTGCCCCATACGGCGCCCTTGGGATTGTATTGG<br>TAGAAGAAATGGTACCACCCCTTGTAGTACATGGGCGCATTGATCCA<br>GTTCTTGGGGGGCTGGAAGTGGTACCCCGTCCTGAGCAGGGGGTTGA<br>CGATGGACGGCGGCACCTGGTCCGTCGCCGCAGCAGCCTCGGCTTCG<br>AGGTCCTTGTAGTTGTAGACGACATGCGACGCTCCTGCGAGCTGCAA<br>CAGCAGCAGCAAGCACGCCGAAGCGAAACTTA |

SPECIFIC MODELS FOR CARRYING OUT THE PRESENT INVENTION

Figure 1:
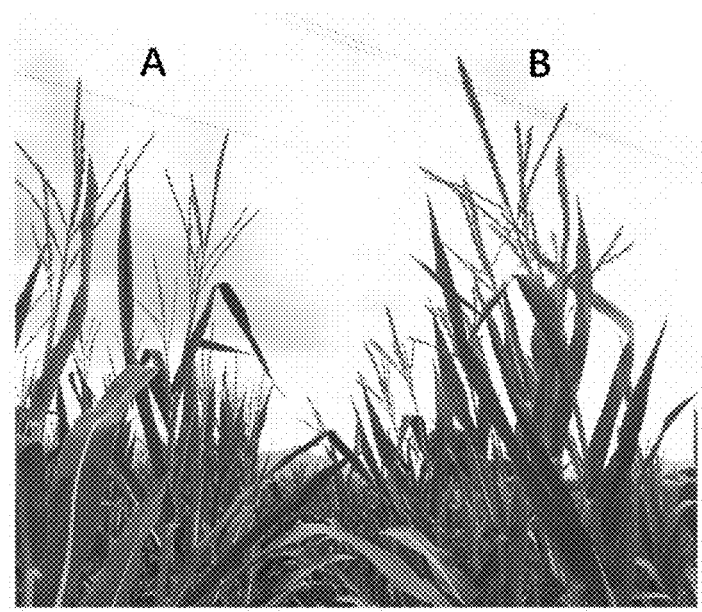
FIG. 1 shows the male flower phenotypes of male sterile maize plant ms45 (A) and wild-type maize plant Ms45 (B).

The present invention will now be described with reference to the following examples which are intended to illustrate the present invention rather than limit the present invention. If specific conditions are not indicated in the examples, they would be carried out in accordance with the conventional conditions or the conditions recommended by the manufacturer. The reagents or instruments used without the manufacturer's indication were all conventional products that could be purchased commercially. Those skilled in the art know that the examples describe the present invention by way of example, and are not intended to limit the scope sought to be protected by the present invention.

EXAMPLE 1: CONSTRUCTION OF VECTOR

In this example, the male sterility gene ms45 and its restoring gene Ms45 in Table 1 were used for experiments.

1. Amplification of Male Sterility Restoring Gene Ms45

The male sterility restoring gene Ms45 was derived from the maize variety B73, its nucleotide sequence was shown in SEQ ID NO: 1, and the Ms45 protein encoded thereby had an amino acid sequence shown in SEQ ID NO: 2. Using B73 genomic DNA as template and referring to the B73 genomic sequence (www.maizesequence.org), amplification primers were designed to amplify the restoring gene Ms45. The designed primers were as follows:

```
Ms45F:
                                       (SEQ ID NO: 11)
  5' tgaattcTGCTGAGTTCTCCTTGGGTTATCC 3', Ms45R:
                                       (SEQ ID NO: 12)
  5' tcccgggGGTTGCGCATGAAATAGGGGT 3'.
```

The designed upstream primer Ms45F contained an EcoRI restriction site at the 5'end, and the downstream primer Ms45R contained an SmaI restriction site at the 5'end, so as to perform amplification. The amplification reaction system was: 24, of template DNA, 0.54, of primer Ms45F, 0.5 µL of primer Ms45R, 1.6 µL of dNTP, 2 µL of 10×Buffer, 0.3 µL of high-fidelity taq enzyme, 13.1 µL of ddH$_2$O. The reaction conditions were: denaturation at 95° C. for 5 minutes; 32 cycles (denaturation at 95° C. for 45 s, annealing at 59° C. for 45 s, and extension at 72° C. for 3 minutes); and extension at 72° C. for 10 minutes.

Experimental results: The amplified target product had a total length of about 3500 bp. It was recovered and ligated to the T-easy sequencing vector, and then used for transformation and sequencing. Sequencing results confirmed that the amplification product was a 3518 bp DNA fragment composed of EcoRI restriction site, the sequence shown in SEQ ID NO: 3, and SmaI restriction site, which was used as the Ms45 gene construct. The sequence shown in SEQ ID NO: 3 contained a nucleotide sequence of the promoter (SEQ ID NO: 15) and coding region of the Ms45 gene.

2. Amplification of Related Genes for Regulating Seed Color, Plant Color and Plant Wilting

1) Amplification of Lc Gene

The Lc gene had a nucleotide sequence shown in SEQ ID NO: 4, and the Lc protein encoded thereby had an amino acid sequence shown in SEQ ID NO: 5. For SEQ ID NO: 4, NcoI restriction site and protective base were added to the 5' end, BstEII restriction site and protective base were added to the 3' end, and this sequence was artificially synthesized and used as a Lc gene construct.

2) Amplification of Oy1 Gene

The Oy1 gene had a nucleotide sequence shown in SEQ ID NO: 6, and the Oy1 protein encoded thereby had an amino acid sequence shown in SEQ ID NO: 7. For SEQ ID NO: 6, NcoI restriction site and protective base were added to the 5' end, BstEII restriction site and protective base were added to the 3' end, and this sequence was artificially synthesized and used as an Oy1 gene construct.

3) Synthesis of Wi2 Gene for Regulating Plant Wilting

Wi2 gene can regulate root suberin, and its expression can affect the water transport of the plant and make the plant be easier to wilt. The Wi2 gene had a nucleotide sequence shown in SEQ ID NO: 8, and the Wi2 protein encoded thereby had an amino acid sequence shown in SEQ ID NO: 9. For SEQ ID NO: 8, NcoI restriction site and protective base were added to the 5' end, BstEII restriction site and protective base were added to the 3' end, and this sequence was artificially synthesized and used as a Wi2 gene construct.

3. Construction of Recombinant *Agrobacterium*

Plasmid pCAMBAI3301 (International Agricultural Molecular Biology Application Center, CAMBIA, Australia) was used to construct the following recombinant expression vectors, and the plasmid contained a selective marker gene bar (which nucleotide sequence was shown in SEQ ID NO: 10).

1) Vector pMs45-Lc

Figure 4:
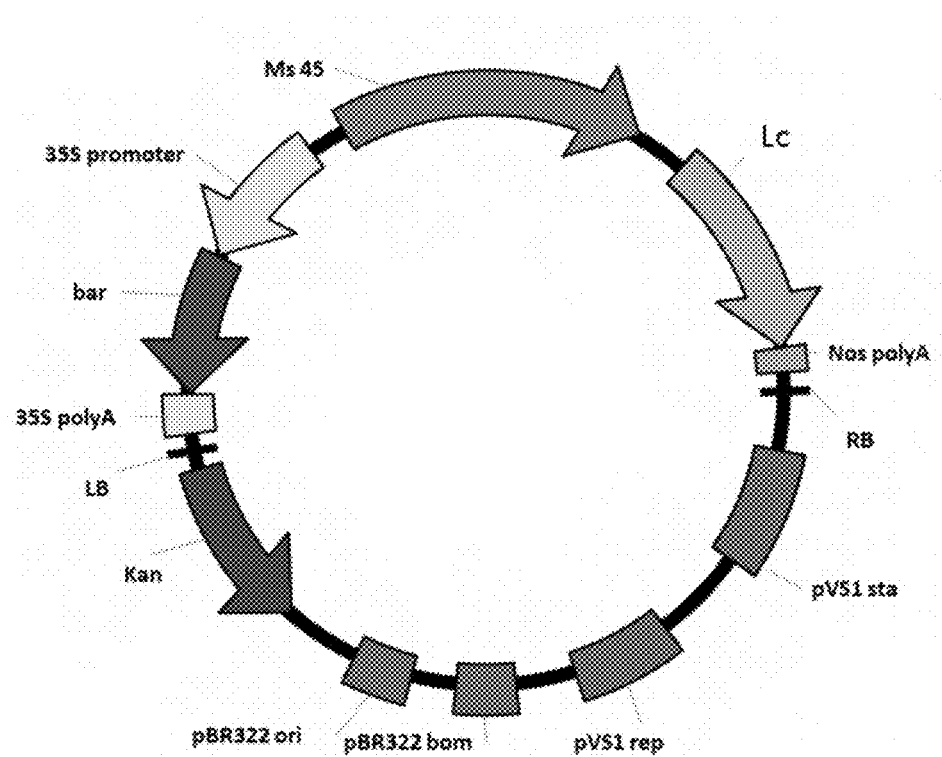
FIG. 4 shows a schematic diagram of the structure of pMs45-Lc vector.

By double-enzyme digestion of the gene construct and plasmid, the Lc gene construct was cloned between the BstEII and NcoI restriction sites of the pCAMBAI3301 plasmid, and the Ms45 gene construct was cloned between the EcoRI and SmaI restriction sites of the pCAMBAI3301 plasmid. The constructed vector was named pMs45-Lc. The schematic structure diagram of the vector was shown in FIG. 4, and the vector contained the Ms45 gene, the Lc gene and the selective marker gene bar of the vector itself.

2) Vector pMs45-Oy1

By double-enzyme digestion of the gene construct and plasmid, the Oy1 gene construct was cloned between the BstEII and NcoI restriction sites of the pCAMBAI3301 plasmid, and the Ms45 gene construct was cloned between the EcoRI and SmaI restriction sites of the pCAMBAI3301 plasmid. The constructed vector was named pMs45-Oy1. The vector contained the Ms45 gene, the Oy1 gene and the selection marker gene bar of the vector itself.

3) Vector pMs45-Wi2

By double digestion of the gene construct and plasmid, the Wi2 gene construct was cloned between the BstEII and NcoI restriction sites of the pCAMBAI3301 plasmid, and the Ms45 gene construct was cloned between the EcoRI and SmaI restriction sites of the pCAMBAI3301 plasmid. The constructed vector was named pMs45-Wi2. The vector contained the Ms45 gene, the Wi2 gene and the selection marker gene bar of the vector itself.

The vectors pMs45-Lc, pMs45-Oy1 and pMs45-Wi2 obtained above were respectively transformed into *Agrobacterium* EHA105 to obtain recombinant *Agrobacterium* strains EHA105/pMs45-Lc, EHA105/pMs45-Oy1 and EHA105/pMs45-Wi2.

In addition, the vectors pMs45-Oy1-CWI-2 (which carried the Ms45 gene, the Oy1 gene, the nucleotides (SEQ ID NO: 18) encoding the interfering RNA of CWI-2 gene, and the selective marker gene bar of the vector itself) and pMs45-Lc-CWI-2 (which carried the Ms45 gene, the Lc gene, the nucleotides (SEQ ID NO: 18) encoding the interfering RNA of CWI-2 gene, and the selective marker gene bar of the vector itself) were prepared by similar methods, and the recombinant *Agrobacterium* strains EHA105/pMs45-Oy1-CWI-2 and EHA105/pMs45-Lc-CWI-2 were prepared.

EXAMPLE 2: ACQUISITION OF TRANSGENIC MAIZE

The maize varieties HiIIA and HiIIB (Armstrong C L, Green C E and Phillips R L. Development and availability of germplasm with high Type II culture formation response. Maize Genetics Cooperation News Letter, 1991, 65:92-93) were planted in the field. They are separately bagged, pollinated, and hybridized when dispersing pollen. Two hybridization methods were used: HiIIA as the female parent and HiIIB as the male parent; or, HiIIA as the male parent and HiIIB as the female parent. 9 to 11 days after the pollination, the immature hybrid embryos were taken from the pollinated ear kernels, and the obtained recombinant *Agrobacterium* strains EHA105/pMs45-Lc, EHA105/pMs45-Lc and EHA105/pMs45-Wi2 were used to infect the maize immature embryos respectively. The infected immature embryos were placed on a selection medium for multiple screenings to obtain resistant calli, and the resistant calli were regenerated into seedlings to obtain transgenic T0 generation plants. After obtaining the transgenic T0 generation, the pollens of the T0 generation transgenic plants were used to pollinate the breeding female parents HiIIA and HiIIB and the ms45 male sterile materials (obtained from Maize Genetics Cooperation Stock Center, 905I), and their phenotypes were observed.

The Specific Implementation Steps were as Follows

1. Obtaining Maize Immature Embryos

1) About 1 cm top ears of the HiIIA and HiIIB hybrid F1 generation plants were cut, and tweezers were inserted from top into the ears. Then ears were placed into a beaker containing a disinfectant. According to the actual needs, 4 to 6 ears could be placed in the same beaker.

2) About 700 ml of disinfectant (50% bleach or 5.25% sodium hypochlorite, and added with a drop of Tween-20) was added to the beaker to immerse the ears. During the disinfection process of about 20 minutes, the ears were rotated from time to time while gently tapping the beaker to drive out bubbles on the surface of the kernels, so as to achieve the best disinfection effect. After disinfection, the ears were taken out and put in a beaker filled with sterilized water, washed in water 3 times, and then prepared to peel off the embryos.

3) The sterilized ears were placed on a large petri dish, and a large scalpel used to cut off the top of the kernels (1.5 to 1.8 mm).

4) The tip of a knife for peeling embryo was inserted between the embryo and the endosperm, then the immature embryo was gently pried up, the embryo was gently lifted by the tip of a small scalpel to ensure that the embryo did not suffer any damage, the embryonal axis surface of the embryo was closely attached to N6E medium with filter paper, and the density of embryo was about 2×2cm (30 pcs/dish).

5) The petri dish was sealed with parafilm and incubated in the dark at 28° C. for 2 to 3 days.

2. *Agrobacterium* Infiltration

1) The recombinant *Agrobacterium* strains EHA105/pMs45-Lc, EHA105/pMs45-Oy1 and EHA105/pMs45-Wi2 were cultured on YEP medium (containing Kana33 mg/L and Str100 mg/L antibiotics) one week in advance.

2) The above-cultured recombinant *Agrobacterium* strains were transferred to fresh YEP medium (containing Kana33 mg/L, Str50 mg/L) and cultured at 19° C. for 3 days.

3) After 3 days, the recombinant *Agrobacterium* was picked and put into a 50 ml centrifuge tube containing 5 mL of infection medium, and 100 uM AS (inf+AS) was added at the same time, and the incubation was performed at room temperature (25° C.) at 75 rpm for 2 to 4 hours.

4) The immature embryos were infected, in which the newly separated immature embryos were placed into a centrifuge tube containing inf+AS liquid medium (2 ml), about 20 to 100 immature embryos were placed in each tube, washing was performed twice with this medium, and then 1 to 1.5 ml of *Agrobacterium* with a specific concentration (OD550=0.3 to 0.4) was added, the centrifuge tube was gently inverted 20 times, and then placed upright in the dark box for 5 minutes, it should be ensured that the immature embryos were all immersed in the *Agrobacterium* liquid, and vortexing and oscillation should be avoided during the whole process.

3. Co-Cultivation

1) After the infection, the infected maize immature embryos were transferred to a co-cultivation medium (which had solute shown in Table 3, and the solvent was water), so that the embryonal axis of the immature embryo was in contact with the surface of the medium, and the excess *Agrobacterium* on the surface of the medium was removed.

2) The petri dish was sealed with parafilm and incubated in the dark at 20° C. for 3 days.

4. Resting Culture

1) After 3 days of the co-cultivation, the immature embryos were transferred to a resting medium (which solute was shown in Table 3, the solvent was water), and the petri dish was sealed with a parafilm at the same time, and cultivation was performed in the dark at 28° C. for 7 days.

5. Selection

1) After 7 days, all the immature embryos were transferred to the selection medium (which solute was shown in Table 3, the solvent was water) (35 immature embryos/each dish) and cultured for two weeks. The selection medium contained 1.5 mg/L of bialaphos. After two weeks, subculture was then performed, in which the concentration of bialaphos could be increased to 3 mg/L.

2) About 5 weeks after the infection, the cells containing the transformants would grow into visible type II calli.

6. Regeneration of Transgenic Plants

1) The calli grew on Regeneration medium I (which solute was shown in Table 3, and the solvent was water) for 3 weeks, and then germinated on Regeneration medium II (which solute was shown in Table 3, and the solvent was water) (placed in a light culture room) to obtain T0 generation transgenic pMs45-Lc maize, pMs45-Oy1 maize and pMs45-Wi2 maize.

2) When 3 to 4 leaves were grown, they were transferred to the greenhouse respectively, and when they grew to the silking and pollination stage, they were pollinated separately.

7. Analysis of the Obtained Transgenic Plants

The obtained T0 generation transgenic pMs45-Lc maize, pMs45-Oy1 maize and pMs45-Wi2 maize and their offsprings were evaluated for the overall plant morphology (for example, pollen, plant and kernel phenotype). The above-mentioned transgenic maizes were crossed with ms45 homozygous recessive male sterile material (obtained from Maize Genetics Cooperation Stock Center, 905I) respectively to obtain hybrid offsprings.

1) Genotype Detection of Hybrid Offsprings

The bar gene was detected to determine whether the hybrid offsprings contained the transgenic elements Ms45-Lc, Ms45-Oy1 or Ms45-Wi2. The bar gene detection method comprised: the following primers Bar669F (SEQ ID NO: 13) and Bar669R (SEQ ID NO: 14) were used to perform PCR amplification of the genomes of the hybrid offsprings, if the amplification product contained a target fragment with a size of about 669 bp, then the hybrid offspring were the offspring that contained the transgenic element; if the amplification product did not contain the 669 bp target fragment, the hybrid offspring were the hybrid offspring that did not contain the transgenic element.

The sequences of the primers Bar669F and Bar669R were as follows:

```
Bar669F:
                                        (SEQ ID NO: 13)
5' TCTCGGTGACGGGCAGGAC 3';

Bar669R:
                                        (SEQ ID NO: 14)
5' TGACGCACAATCCCACTATCCTT 3'.
```

After the verification by PCR and sequencing, the hybrid offspring containing the transgenic element Ms45-Lc, the hybrid offspring containing the transgenic element Ms45-Oy1 and the hybrid offspring containing the transgenic element Ms45-Wi2 were obtained respectively.

Figure 2:
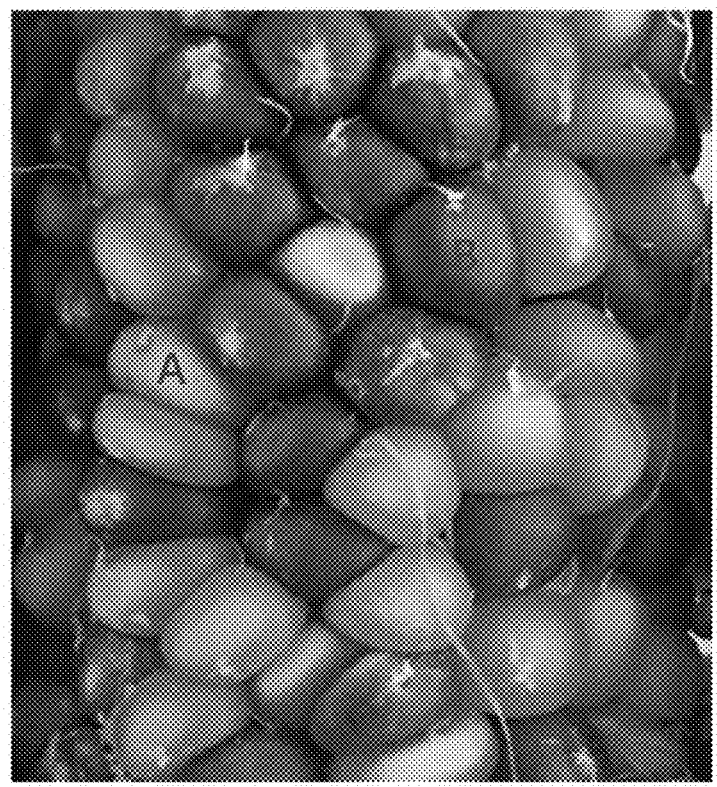
FIG. 2 shows the hybrid offspring seeds (A, the seed color is yellow) that do not contain the transgenic element Ms45-Lc and the hybrid offspring seeds (B, the seed color is purple) that contain the transgenic element Ms45-Lc.
Figure 3:
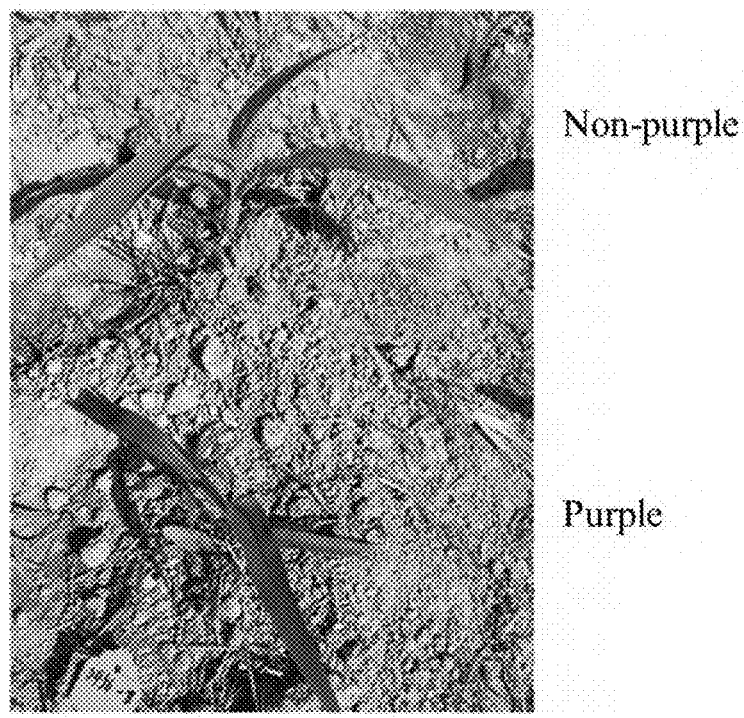
FIG. 3 shows the hybrid offspring seedling (which is not purple) that does not contain the transgenic element Ms45-Lc and the hybrid offspring seedlings (which is purple) that contains the transgenic element Ms45-Lc.
Figure 5:
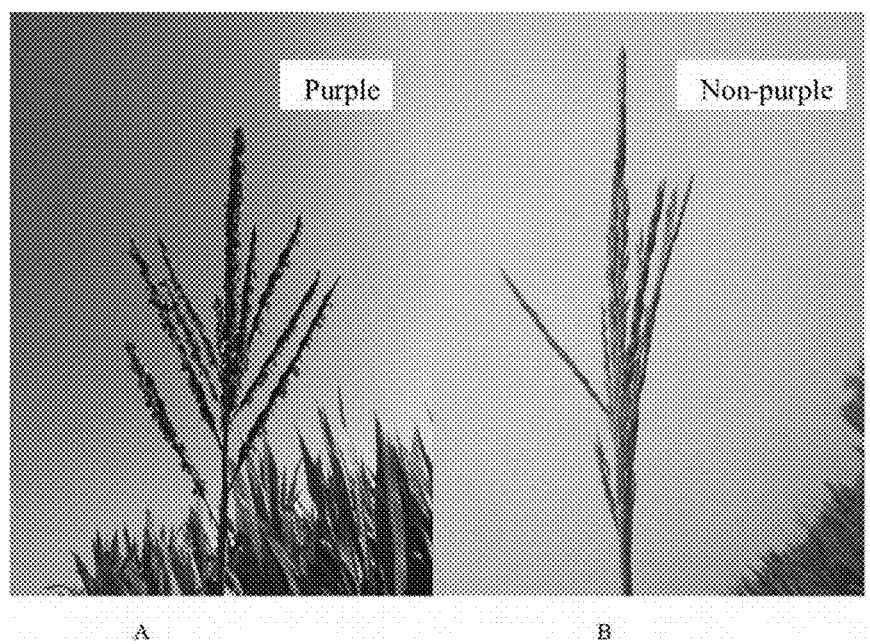
FIG. 5 shows the hybrid offspring plant (A, the plant is purple, and is male fertile) that contains the transgenic element Ms45-Lc, and the hybrid offspring plant (B, the plant is non-purple, and is male sterile) that does not contain the transgenic element Ms45-Lc.

2) Detection of Representative Type after Hybridization (1) Detection of Hybrid Offspring Containing the Transgenic Element Ms45-Lc The phenotypes of the hybrid offsprings cultivated in the field were observed, and the plant colors of the hybrid offsprings were shown in FIG. 5, in which the hybrid offspring containing the transgenic element Ms45-Lc was shown in FIG. 5A, and the plant was purple (detected to be fertile); and the hybrid offspring without transgenic element of Ms45-Lc was shown in FIG. 5B, and the plant was not purple (detected to be sterile). The results of the seed color of the hybrid offsprings were shown in FIG. 2, in which FIG. 2B showed the hybrid offspring seed containing the transgenic element Ms45-Lc, the seed color was purple (detected to be fertile), and FIG. 2A showed the hybrid offspring seed without the transgenic element Ms45-Lc, the seed color was yellow (not purple, detected to be sterile). The results of the seedling colors of the hybrid offsprings were shown in FIG. 3, in which the hybrid offspring seedling containing the transgenic element Ms45-Lc was purple (detected to be fertile), and the hybrid offspring seedling without the transgenic element Ms45-Lc was not purple (detected to be sterile).

The above detection results indicated that the expression of the Ms45 gene in the plants rescued the male sterility phenotype caused by the recessive homozygous ms45 gene. At the same time, the transgenic plants or seeds containing Ms45-Lc were purple. This indicated that the Lc gene could function normally in the transgenic plants. The purple seeds and non-purple (yellow) seeds obtained above were sown in the field, and these seeds were able to germinate normally, and there was no significant difference in the germination rate. In addition, the purple seeds and plants can still grow normally under the selection of bialaphos. The above results showed that the selection marker gene bar, the Ms45 gene and the Lc gene could all function normally, and these three genes were linked in inheritance. In the offspring produced by crossing the T0 generation transgenic plant with the male sterility line plant ms45, the ratio of normal seed to purple seed was 1:1, and the purple seed offsprings were all purple seedlings.

(2) Detection of Hybrid Offspring Containing the Transgenic Element Ms45-Oy1

Figure 7:
FIG. 7 shows the hybrid offspring plant (A, the plant is yellow) that contains the transgenic element Ms45Oy1, and the hybrid offspring plant (B, the plant is green) that does not contain the transgenic element Ms45-Oy1.

The phenotypes of the hybrid offsprings cultivated in the field were observed, and the plant colors of the hybrid offsprings were shown in FIG. 7, in which the hybrid offspring containing the transgenic element Ms45-Oy1 was shown in FIG. 7A, and the plant was yellow (detected to be fertile); while the hybrid offspring without the transgenic element Ms45-Oy1 was shown in FIG. 7B, and the plant was green (detected to be sterile).

(3) Detection of Hybrid Offspring Containing the Transgenic Element Ms45-Wi2

Figure 8:
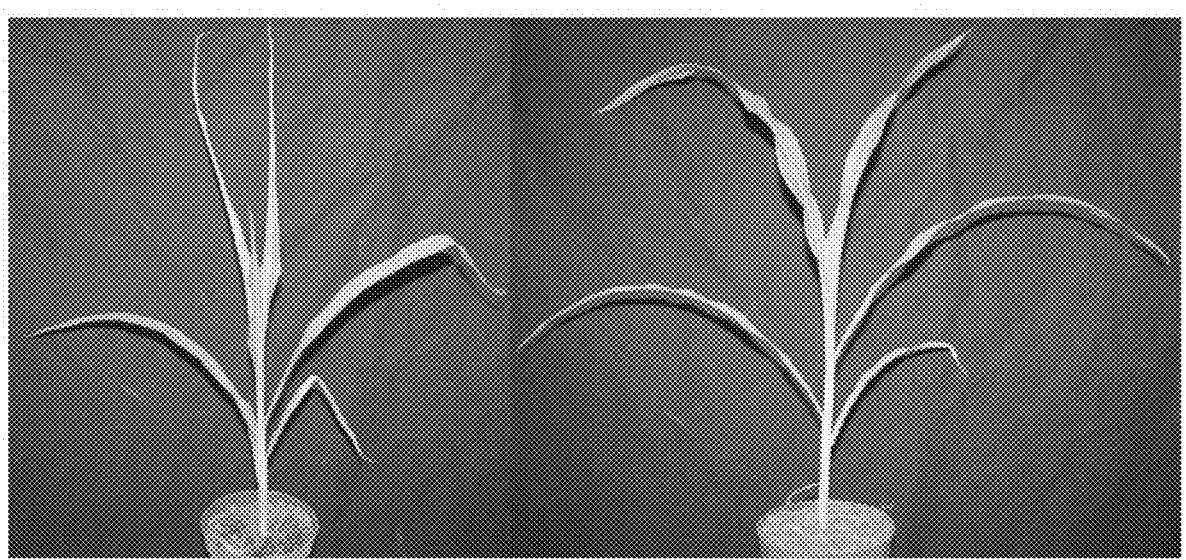
FIG. 8 shows the hybrid offspring plant (A, the plant appears to be wilting) that contains the transgenic element Ms45-Wi2, and the hybrid offspring plant (B, the plant appears to be normal) that does not contain the transgenic element Ms45-Wi2.

The phenotypes of the hybrid offsprings cultivated in the field were observed, and the plant wilting degrees of the hybrid offsprings were shown in FIG. 8, in which the hybrid offspring containing the transgenic element Ms45-Wi2 was shown in FIG. 8A, and the plant was wilting (detected to be fertile); and the hybrid offspring plant without the transgenic element Ms45-Wi2 was shown in FIG. 8B, and the plant was normal (detected to be sterile).

TABLE 3

Solutes and concentrations for culture media

| ingredient | AS(inf + AS) | Co-cultivation Medium | Resting medium | Selection medium | Regeneration medium I | Regeneration medium II |
|---|---|---|---|---|---|---|
| MS salt | 2.16 g/L | 4.33 g/L | 4.33 g/L | 4.33 g/L | 4.33 g/L | 2.16 g/L |
| Sucrose | 68.5 g/L | 30 g/L | 30 g/L | 30 g/L | 30 g/L | 30 g/L |
| Glucose | 30 g/L | | | | | |
| L-proline | 0.115 g/L | 1.38 g/L | 1.38 g/L | 1.38 g/L | 1.38 g/L | |
| Vitamin $B_1$ | | 0.5 mg/L | 0.5 mg/L | 0.5 mg/L | 0.5 mg/L | |
| 2,4-D | | 5 mg/L | 5 mg/L | 5 mg/L | | |
| 6-BA | | 0.01 mg/L | 0.01 mg/L | 0.01 mg/L | 3.5 mg/L | |
| IBA | | | | | | 0.75 mg/L |
| NAA | | | | | | 0.5 mg/L |
| 4-amino-3,5,6-trichloropyridinecarboxylic acid (picloram) | | | | | 1 mg/L | |
| Timentin | | | 100 mg/L | 100 mg/L | 100 mg/L | |
| Bialaphos | | | | 3 mg/L | 3 mg/L | 3 mg/L |
| Agar | | 6 g/L | | | | |
| phytagel | | | 3 g/L | 3 g/L | 3 g/L | 3 g/L |
| pH | 5.7 | 5.7 | 5.7 | 5.7 | 5.7 | 5.7 |
| $AgNO_3$ | | 3.4 mg/L | 3.4 mg/L | 3.4 mg/L | | |
| Acetosyringone | 200 μmol/L | 200 μmol/L | 200 μmol/L | | | |

In the above table, MS salt was purchased from Phyto Technology Laboratories, and the article number was M524.

In addition, by a method similar to the above, the recombinant *Agrobacterium* strains EHA105/pMs45-Oy1-CWI-2 and EHA105/pMs45-Lc-CWI-2 were used to prepare transgenic pMs45-Oy1-CWI-2 maize (which contained the transgenic element Ms45-Oy1-CWI-2) and transgenic pMs45-Lc-CWI-2 maize (which contained the transgenic element Ms45-Lc-CWI-2).

EXAMPLE 3. LARGE-SCALE EXPANSION OF MALE STERILITY LINES USING MALE STERILE MAINTAINER LINES

1. Preparation of Male Sterility Lines

The ms45 homozygous recessive mutant (Maize Genetics Cooperation Stock Center, 9051) was used as female parent and crossed with Zheng58 (Food Crops Research Institute, Henan Academy of Agricultural Sciences), and the obtained F1 continued to be backcrossed with the maize inbred line Zheng58. Genotype analysis was performed on the obtained BC1 (backcross generation) population, and the plants that were heterozygous at the Ms45 locus were screened and continued to be backcrossed with Zheng58. After 5 to 6 generations of such backcrossing, the individual plants with heterozygous Ms45 locus and agronomic traits similar to Zheng58 were screened by molecular markers and selfed to obtain ms45 homozygous recessive inbred line Zheng58 (ms45ms45), and the inbred line could be used as a male sterility line plant.

The method for screening the Ms45 locus genotype was as follows: the following primers Ms45F1 (SEQ ID NO: 16) and Ms45R1 (SEQ ID NO: 17) were used to perform PCR amplification of the plant genome, and the amplification products were sequenced. The Ms45 target fragment had a size of 859bp, and the ms45 target fragment had a size of 811bp. If the amplification product contained both the 859bp and 811bp target fragments, the genotype of the locus was heterozygous Ms45/ms45; if the amplification product did not contain the 811bp fragment, the genotype of the locus was dominant homozygous Ms45/Ms45; if the amplification product did not contain the 859 bp target fragment, the genotype of the locus was recessive homozygous ms45/ms45.

```
Ms45F1:
                                       (SEQ ID NO: 16)
5' CTTGAGCGACAGCGGGAACT 3';

Ms45R1:
                                       (SEQ ID NO: 17)
5' TGTTGTTTCTTGGCAAAGGTCAG 3'.
```

2. Preparation of Maintainer Lines

(1) Preparation of Maintainer Liner Plants with Heterozygous Ms45-Lc and Homozygous ms45

The T0 generation transgenic pMs45-Lc maize in Example 2 was used as male parent, and crossed with the above-obtained Zheng58 (ms45ms45) as female parent. The purple seeds were selected from the hybrid offspring, sown in the field and then sprayed with 200 mM bialaphos. The surviving plants were continued to backcross with the female parent Zheng58. In the process of backcrossing, purple seeds and plants were always selected to cross with the female parent. After 5 to 6 generations of backcrossing, the transgenic loci (Ms45-Lc) of purple seeds and plants in the offspring were all heterozygous. When pollens of purple seeds and plants were used to pollinate the female parent, if the normal seeds (yellow seeds) or normal plants (green plants) obtained were all sterile, the pollen-providing plants had heterozygous Ms45-lc transgenic locus and recessive homozygous ms45 locus, that was, they were maintainer line plants.

(2) Preparation of Maintainer Line Plants with Heterozygous Ms45-Oy1 and Homozygous ms45

The T0 generation transgenic pMs45-Oy1 maize in Example 2 was used as male parent, and crossed with the above-obtained Zheng58 (ms45ms45) as female parent. The yellow plants were selected from the hybrid offspring, sown in the field and then sprayed with 200 mM bialaphos. The surviving plants were continued to backcross with the female parent Zheng58. In the process of backcrossing, yellow plants were always selected to cross with the female parent. After 5 to 6 generations of backcrossing, the transgenic loci (Ms45-Oy1) of yellow plants in the offspring were all heterozygous. When pollens of yellow plants were used to pollinate the female parent, if the normal plants (green plants) obtained were all sterile, the pollen-providing plants had heterozygous Ms45-Oy1 transgenic locus and recessive homozygous ms45 locus, that was, they were maintainer line plants.

(3) Preparation of Maintainer Line Plants with Heterozygous Ms45-Wi2 and Homozygous ms45

The T0 generation transgenic pMs45-Wi2 maize in Example 2 was used as male parent, and crossed with the above-obtained Zheng58 (ms45ms45) as female parent. The wilted plants (which wilting degrees were shown in FIG. 8A, and mainly presented curl heart leaves) were selected from the hybrid offspring, sown in the field and then sprayed with 200 mM bialaphos. The surviving plants were continued to backcross with the female parent. In the process of backcrossing, wilted plants were always selected to cross with the female parent. After 5 to 6 generations of backcrossing, the transgenic loci (Ms45-Wi2) of wilted plants in the offspring were all heterozygous. When pollens of wilted plants were used to pollinate the female parent, if the normal plants (green plants) obtained were all sterile, the pollen-providing plants had heterozygous Ms45-Wi2 transgenic locus and recessive homozygous ms45 locus, that was, they were maintainer line plants.

3. Acquisition of Maintainer Lines

Figure 6:
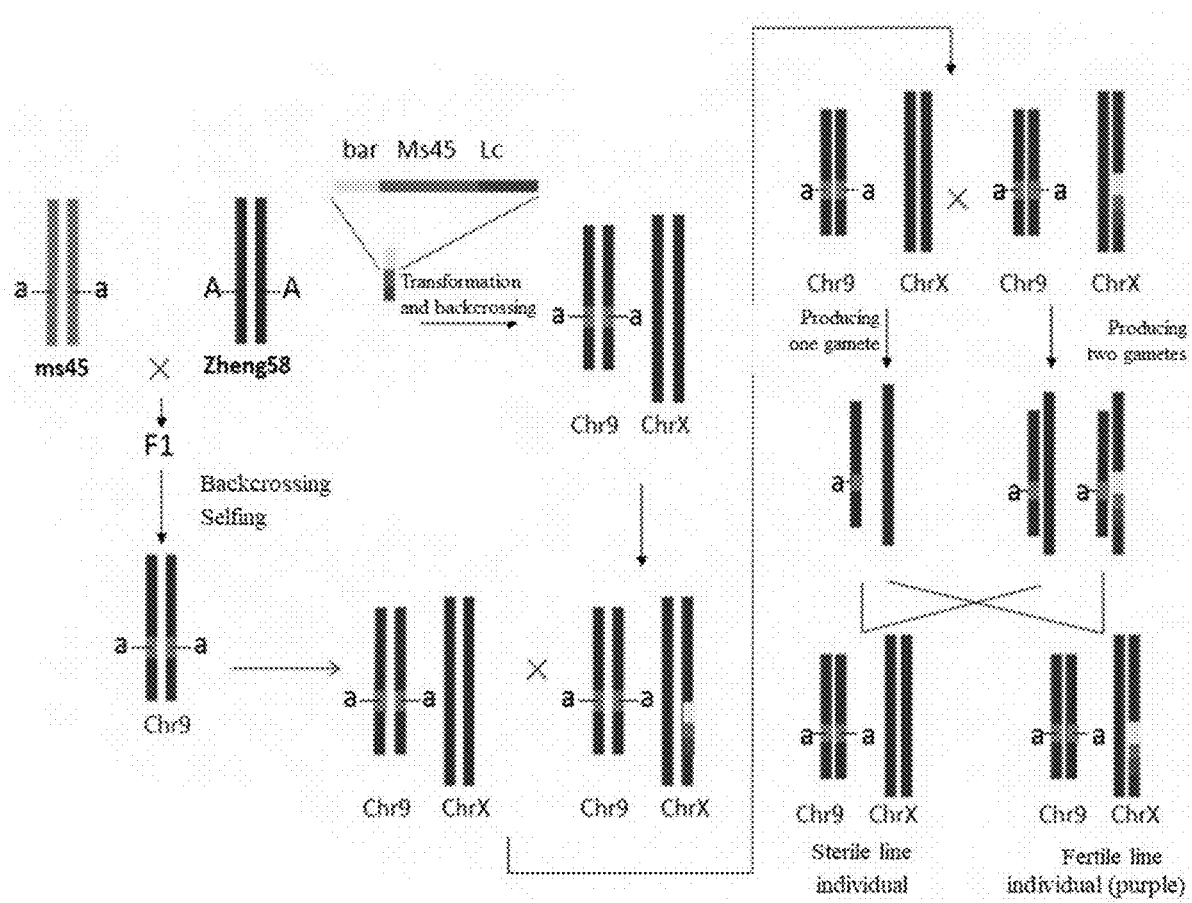
FIG. 6 schematically shows the process for selection and breeding of maintainer line plants, sterile plants and their hybrid offsprings.

The obtained maintainer line plants (Ms45-Lc heterozygous and ms45ms45) were used as male parent and crossed with Zheng58 as the female parent. The offsprings produced not only had male sterility line (ms45ms45), but also had maintainer line (Ms45-Lc heterozygous and ms45ms45). In addition, the seeds of the male sterility line (ms45ms45) were normal, while the seeds of the maintainer line (Ms45-Lc heterozygous and ms45ms45) were purple (the seeds shown in FIG. 2B). See FIG. 6 for the specific breeding process.

The obtained maintainer line plants (Ms45-Oy1 heterozygous and ms45ms45) were used as male parent and crossed with Zheng58 as female parent. The offsprings produced not only had male sterility line (ms45ms45), but also maintainer line (Ms45-Oy1 heterozygous and ms45ms45). In addition, the male sterility line plants (ms45ms45) were normal and show green color (as shown in FIG. 7B), while the maintainer line plants (Ms45-Oy1 heterozygous and ms45ms45) were yellow.

The obtained maintainer line plants (Ms45-Wi2 heterozygous and homozygous ms45) were used as male parent and crossed with Zheng58 as female parent. The offsprings produced not only had male sterility line (ms45ms45), but also maintainer line (Ms45-Wi2 heterozygous and ms45ms45). In addition, the male sterility line plants (ms45ms45) were normal (as shown in FIG. 8B), while the maintainer line plants (Ms45-Wi2 heterozygous and ms45ms45) showed a wilting state.

4. Large-Scale Expansion of Male Sterility Lines Using Male Sterile Maintainer Lines Taking the Zheng58 inbred line as an example, the obtained male sterility line Zheng58 (ms45ms45) was sown in combination with the above-obtained maintainer lines (Ms45-Lc heterozygous and ms45ms45, Ms45-Oy1 heterozygous and ms45ms45, and Ms45-Wi2 heterozygous and ms45ms45), respectively. The two materials were sown separately, in which when each row of maintainer line was sown, 5 rows of sterile line were correspondingly sown, and it was ensured that no other maize was sown within 300 meters around the breeding field, so that the sterile line and the maintainer line were naturally pollinated in the field.

The maintainer line could only accept its own pollen and would produce two kinds of offspring. One was the offspring that exhibited the external traits of transgenic elements (for example, purple seeds and purple plants, yellow plants, wilted plants). The transgenic elements of these offspring may be homozygous or heterozygous, making it difficult to distinguish. Therefore, these seeds or plants were discarded. The other one was the offspring with normal external traits, did not contain transgenic elements, and could be used as the sterile line offspring and retained.

The sterile line material received the pollen from the maintainer line and produced two kinds of offspring. One was the offspring that exhibited the external traits of transgenic elements (for example, purple seeds and purple plants, yellow plants, wilted plants). The transgenic elements of these offspring were heterozygous, and thus they could be used as the maintainer line offspring and retained. The other one was the offspring with normal external traits (for example, yellow seeds, green plants, non-wilted plants), which did not contain transgenic elements, and could be used as the sterile line offspring and retained. The maintainer line could be used in the next year to continue the expansion of the sterile line and the maintainer line, while most of the sterile line was used to produce commercial seeds, and the remaining small part was used in the next year to continue the expansion of the sterile line and the maintainer line. The production process was shown in FIG. 6.

In addition, by a method similar to the above, the maintainer line plants with heterozygous Ms45-Oy1-CWI-2 and homozygous ms45 were obtained, and the maintainer line plants with heterozygous Ms45-Lc-CWI-2 and homozygous ms45 were obtained, and both of them could be used for large-scale expansion of male sterility lines (ms45ms45).

EXAMPLE 4. LARGE-SCALE PRODUCTION OF HYBRIDS USING MALE STERILITY LINES

The sterile lines produced in Example 3 were recessive homozygous sterile lines controlled by nucleus, and the sterile lines could be restored to fertility by any wild-type plant (Ms45Ms45). Therefore, as long as an inbred line (for example, Chang 7-2) with high combining ability with the male sterility lines (for example, Zheng58) was selected, hybrids with excellent agronomic traits would be produced.

In order to achieve the above objects, Zheng58 and Chang 7-2 were subjected to alternate-row-seeding in the field, and no other maize was sown within 300 meters around the breeding field. Thus, the ears of the sterile lines could only accept the pollens of the wild-type inbred line, while the wild-type inbred line could only be selfed. In this way, the seeds produced on the ears of the sterile lines were dominant hybrids.

EXAMPLE 5: QUALITY ASSESSMENT OF HYBRIDS BRED BY STERILE LINES

Previously, the inventors of the present application had used a vector containing both Ms45 and mn1 RNAi (Chinese Patent ZL201210406155.6) to create a male sterile maintainer line that was marked by seed size. However, due to the existence of heterofertilization (the embryo and endosperm of the same seed were fertilized by sperms formed by two different male gametophytes in the double fertilization process), the male sterility line offspring population produced by this type of male sterile maintainer line could not achieve 100% sterility. Specifically, we used the method described in Chinese patent ZL201210406155.6 to expand and multiply and prepare a large number of sterile maize seeds; subsequently, they were sown in the field, and the number of pollen-dispersal plants was observed and recorded during the pollinating period. The results showed that a total of 320 pollen-dispersal plants (such plants contained transgenic components derived from the maintainer line) were observed in 100,000 plants. This indicated that a small number of male fertile individuals were mixed in the sterile line seeds obtained (accounting for about 3.2‰ of the sterile line offspring population produced). Further, the sterile line plant population mixed with male fertile individuals (i.e., maintainer line individuals) was crossed with a target maize line (for example, Chang 7-2) plants to produce hybrids. Then, the produced hybrids were sown in the field, and 10,000 plants were randomly selected for genetic testing. The results showed that there were 210 hybrids containing the transgenic components derived from the maintainer line, accounting for 2.1%. This result indicated that the seed purity of the produced hybrids should still be improved and could not fully meet the production requirements. This had brought adverse effects and potential risks to the marketization of hybrids.

In this example, the Lc gene was used to double-mark the plants (seed color and plant color), which solved the problem caused by heterofertilization and significantly improved the seed purity of the hybrids produced (to 100%).

In short, the maintainer line plants (transgenic pMs45-Lc/ms45ms45 maize) and the sterile line plants (ms45ms45 maize) obtained in the above examples were sown separately, in which when one row of the maintainer line was sown, 5 rows of sterile line were sown correspondingly, and it was ensured that no other maize was sown within 300 meters around the breeding field, so that the sterile line plants and maintainer lines were allowed to be pollinated naturally in the field. The offspring seeds of the sterile line plants were collected, and the first screening was performed according to the color of the seeds, that was, the offspring of the sterile line (the seeds were yellow) and the offspring of the maintainer line (the seeds were purple) were distinguished.

Then, the obtained sterile line seeds (as the female parent) and the target maize line seeds (as the male parent, Chang 7-2 inbred line) were subjected to alternate-row-seeding, in which when one row of the target maize line seeds was sown, 5 rows of the sterile line seeds were sown correspondingly, and it was ensured that no other maize was sown within 300 meters around the breeding field. In the seedling stage of maize growth, the external traits of the sterile line plants were observed, and the plants showing the purple plant color were removed from the sterile line plants. According to statistics, among 100,000 sterile plants, 290 purple seedlings were removed, that was, the purity of the expanded sterile line was 99.71%.

After screening, the sterile line plants and the target maize line plants were allowed to be naturally pollinated in the field. The hybrid seeds produced on the sterile line plants were collected. Then, the produced hybrid seeds were sown in the field, and 10,000 plants were randomly selected for genetic testing to determine the proportion of hybrid seeds containing the transgenic components (pMs45-Lc) derived from the maintainer line, and to evaluate the quality of hybrid seeds (purity). The experimental results showed that after double screening by using seed color and plant color, the purity of the hybrid seeds produced reached 100%, that was, all hybrid seeds did not contain transgenic components derived from the maintainer line (pMs45-Lc).

Based on this result, it could be determined that by using the male sterile maintainer line of the present invention, with the aid of double screening (seed screening and seedling stage screening), both the progeny sterile line plants and the progeny maintainer line plants could achieve a purity of 100% at the seedling stage. The male sterile maintainer line and the seed breeding method of the present invention could be used to produce high-purity sterile line offspring seeds and high-purity hybrid seeds.

EXAMPLE 6: QUALITY ASSESSMENT OF HYBRIDS BRED BY STERILE LINES

In this example, the present inventors used the two traits of seed size (interfering RNA of CWI-2 gene) and plant color (Oy1 gene) to mark the plants. Therefore, during the seed production process, the fertile maintainer line (i.e., yellow seedlings; about 3‰) produced by heterofertilization in the plot of female parent sterile line was removed at the seedling stage, so as to ensure 100% male sterility of all female parents during the pollen-dispersal period, thereby improving and ensuring the purity of the hybrids produced, and satisfying the needs of production well.

In short, according to the experimental method described in the above example, the Ms45 gene (SEQ ID NO: 1), Oy1 gene (SEQ ID NO: 6) and the nucleotides (SEQ ID NO: 18) encoding the interfering RNA of CWI-2 gene were constructed into a vector, and a maintainer line plant was produced, that was, a transgenic maize plant pMs45-Oy1-CW1-2/ms45ms45, which could express Ms45 protein, Oy 1 protein, and interfering RNA that inhibited CWI-2 gene. The obtained maintainer line plants (pMs45-Oy1-CW1-2/ms45ms45) and the sterile plants (ms45ms45 maize) were subjected to alternate-row-seeding, in which when one row of the maintainer line was sown, 5 rows of the sterile lines were sown correspondingly, and it was ensured that no other maize was sown within 300 meters around the breeding field, so that the sterile line plants and the maintainer line plants were allowed to be naturally pollinated in the field. The offspring seeds of the sterile line plants were collected, and the first screening was performed according to the size of the seeds, that was, the offspring of the sterile line (the seed size was normal) and the offspring of the maintainer line (the seed size was small) were distinguished.

Then, the obtained sterile line seeds (as the female parent, the seed size was normal) and the target maize line seeds (as the male parent, Chang 7-2 inbred line, the seed size was normal) were sown separately, in which when one row of the target maize line seeds was sown, 5 rows of the sterile line seeds were sown accordingly, and it was ensured that no other maize was sown within 300 meters around the breeding field. In the seedling stage of maize growth, the external traits of the sterile line plants were observed, and the plants showing the yellow plant color were removed from the sterile line plants. According to statistics, 310 yellow seedlings out of 100,000 sterile line plants were removed, that was, the purity of the expanded sterile line was 99.69%.

After screening, the sterile line plants and the target maize line plants were allowed to be naturally pollinated in the field. The hybrid seeds produced on the sterile plants were collected. Then, the produced hybrid seeds were sown in the field, and 10,000 plants were randomly selected for genetic testing to determine the proportion of hybrid seeds containing the transgenic components derived from the maintainer line (pMs45-Oy1-CWI-2) and evaluate the quality (purity) of the hybrid seeds. The experimental results showed that after double screening by using seed color and plant color, the purity of the hybrid seeds produced reached 100%, that was, all hybrid seeds did not contain the transgenic components derived from the maintainer line (pMs45-Oy1-CWI-2).

Based on this result, it could be determined that by using the male sterile maintainer line of the present invention, with the aid of double screening (seed screening and seedling stage screening), the progeny sterile line plants and the progeny maintainer line plants could achieve a purity of 100% at the seedling stage. The male sterile maintainer line and the seed breeding method of the present invention could be used to produce high-purity sterile line offspring seeds and high-purity hybrid seeds.

EXAMPLE 7: QUALITY ASSESSMENT OF HYBRIDS BRED BY STERILE LINES

In this example, the present inventors used the two traits of seed size (interfering RNA of CWI-2 gene) and plant color (Lc gene) to mark the plants. Therefore, in the seed production process, the fertile maintainer line (i.e., purple seedlings; about 3‰) produced by heterofertilization in the plot of female parent sterile line was removed at the seedling stage, so as to ensure 100% male sterility of all female parents during the pollen-dispersal period, thereby improving and ensuring the purity of the hybrids produced, and satisfying the needs of production well.

In short, according to the experimental method described in the above examples, the Ms45 gene (SEQ ID NO: 1), Lc gene (SEQ ID NO: 4) and nucleotide (SEQ ID NO: 18) encoding the interfering RNA of CWI-2 gene were constructed into a vector, and a maintainer line plant was produced, namely the transgenic maize plant pMs45-Lc-CWI-2/ms45ms45 maize, which could express Ms45 protein, Lc protein, and inhibit the interfering RNA of CWI-2 gene. The obtained maintainer line plants (pMs45-Lc-CWI-2/ms45ms45 maize) and sterile line plants (ms45ms45 maize) were sown separately, in which when one row of the maintainer line was sown, 5 rows of sterile line were sown accordingly, and it was ensured that no other maize was sown within 300 meters around the breeding field, so that the sterile line plants and the maintainer line plants were allowed to be naturally pollinated in the field. The offspring seeds of the sterile line plants were collected, and the first screening was performed according to the size of the seeds, that was, the offspring of the sterile line (the seed size was normal) and the offspring of the maintainer line (the seed size was small) were distinguished.

Then, the obtained sterile line seeds (as the female parent, the seed size was normal) and the target maize line seeds (as the male parent, Chang 7-2 inbred line, the seed size was normal) were sown separately, in which when one row of the target maize line seeds was sown, 5 rows of the sterile line seeds were sown accordingly, and it was ensured that no other maize was sown within 300 meters around the breeding field. In the seedling stage of maize growth, the external traits of the sterile line plants were observed, and the plants showing the purple plant color were removed from the sterile line plants. According to statistics, 305 purple seedlings out of 100,000 sterile line plants were removed, that was, the purity of the expanded sterile line was 99.695%.

After screening, the sterile line plants and the target maize line plants were allowed to be naturally pollinated in the field. The hybrid seeds produced on sterile plants were collected. Then, the produced hybrid seeds were sown in the field, and 10,000 plants were randomly selected for genetic testing to determine the proportion of hybrid seeds containing the transgenic components (pMs45-Lc-CWI-2) derived from the maintainer line and evaluate the quality (purity) of the hybrid seeds. The experimental results showed that after double screening by using seed color and plant color, the purity of the hybrid seeds produced reached 100%, that was, all hybrid seeds did not contain the transgenic components (pMs45-Lc-CWI-2) derived from the maintainer line.

Based on this result, it could be determined that by using the male sterile maintainer line of the present invention, with the aid of double screening (seed screening and seedling stage screening), the progeny of sterile line plants and the progeny of maintainer line plants could achieve a purity of 100% at the seedling stage. The male sterile maintainer line and the seed breeding method of the present invention could be used to produce high-purity sterile line offspring seeds and high-purity hybrid seeds.

What is claimed is:

1. An isolated nucleic acid molecule, which comprises a first polynucleotide, a second polynucleotide and a third polynucleotide; wherein the first polynucleotide comprises a nucleotide sequence of a male fertility restoring gene of a plant that has male sterility caused by a male sterility gene; wherein the male sterility gene is a recessive male sterility gene, which causes plant male sterility in a homozygous state; wherein the restoring gene is ms45 and has the nucleotide sequence of SEQ ID NO: 1; wherein the second polynucleotide comprises: (a) a first screening gene that regulates a seed external trait, and (b) a second screening gene that regulates a plant external trait; wherein, (i) the first screening gene is Lc gene, and the second screening gene is Wi2 gene; or
(ii) the first screening gene is interfering RNA of CWI-2 gene, and the second screening gene is Le gene; or
(iii) the first screening gene is interfering RNA of CWI-2 gene, and the second screening gene is Oy1 gene;

wherein the Lc gene has the nucleotide sequence of SEQ ID NO: 4, the Oy1 gene has the nucleotide sequence of SEQ ID NO: 6, the Wi2 gene has the nucleotide sequence of SEQ ID NO: 8, and the nucleotides encoding the interfering RNA of CWI-2 gene has the nucleotide sequence of SEQ ID NO: 18; and wherein the third polynucleotide comprises a nucleotide sequence of a heterologous selective marker gene.

2. The isolated nucleic acid molecule according to claim 1, wherein the second polynucleotide further comprises: an expression regulatory element operably linked to the first or second screening gene.

3. The isolated nucleic acid molecule according to claim 2, wherein:
(i) the Lc gene encodes a protein with the amino acid sequence of SEQ ID NO: 5;
(ii) the Oy1 gene encodes a protein with the amino acid sequence of SEQ ID NO: 7;
(iii) the Wi2 gene encodes a protein with the amino acid sequence of SEQ ID NO: 9;
and wherein the expression regulatory element is a promoter selected from the group consisting of: constitutive promoter, inducible promoter, tissue-preferred promoter, tissue-specific promoter, and growth-phase-preferred promoter.

4. The isolated nucleic acid molecule according to claim 1, wherein:
(i) the male sterility gene is ms45;
(ii) the restoring gene encodes a protein with the amino acid sequence of SEQ ID NO: 2;
(iii) the first polynucleotide further comprises: an expression regulatory element operably linked to the restoring gene;
(iv) the first polynucleotide sequence comprises SEQ ID NO: 3;
(v) the first polynucleotide and the second polynucleotide are covalently ligated between each other with or without a nucleotide linker;
(vi) the first polynucleotide and the second polynucleotide are genetically linked.

5. The isolated nucleic acid molecule according to claim 1, wherein:
(i) the selective marker gene is an antibiotic resistance gene or a herbicide resistance gene;
(ii) the selective marker gene is a bialaphos resistance gene;
(iii) the selective marker gene is a bar gene; or
(iv) the selective marker gene has the nucleotide sequence of SEQ ID NO: 10; and
(v) the nucleotide linker has a length of not more than 10 kb, not more than 5 kb, not more than 1 kb, not more than 500 bp, not more than 100 bp, not more than 50 bp, not more than 10 bp, or not more than 5 bp.

6. A vector comprising the isolated nucleic acid molecule according to claim 1.

7. A host cell comprising the isolated nucleic acid molecule according to claim 1 or a vector comprising the isolated nucleic acid molecule;
optionally, the host cell is an *Agrobacterium* cell or a maize cell.

8. A maize plant or maize seed, wherein the maize plant or maize seed contains in its genome the nucleic acid molecule according to claim 1 and optionally, the male sterility gene.

9. The maize plant or maize seed according to claim 8, wherein the maize plant or maize seed has one or more of the following characteristics:

(i) the maize or maize seed further contains the male sterility gene in a homozygous state;
(ii) the isolated nucleic acid molecule is integrated in the genome of the maize plant or maize seed;
(iii) the isolated nucleic acid molecule is integrated in the genome of the maize or maize seed, and is located on a chromosome different from that of the male sterility gene;
(iv) the isolated nucleic acid molecule is present in the genome of the maize plant or maize seed in a heterozygous form; and
(v) the maize plant or maize seed is male fertile.

10. A method for obtaining a maize plant, the method comprising:
(a) introducing a nucleic acid molecule or a vector comprising the nucleic acid molecule into a maize cell, and
(b) cultivating the maize cell into a maize plant; optionally, the maize cell contains the male sterility gene in its genome;
wherein the nucleic acid molecule comprises a first polynucleotide and a second polynucleotide,
wherein the first polynucleotide comprises a nucleotide sequence of a male fertility restoring gene of a plant that has male sterility caused by a male sterility gene; wherein the male sterility gene is a recessive male sterility gene, which causes plant male sterility in a homozygous state; wherein the male fertility restoring gene is ms45 and has the nucleotide sequence of SEQ ID NO: 1;
wherein the second polynucleotide comprises: (a) a first screening gene that regulates a seed external trait, and (b) a second screening gene that regulates a plant external trait;
wherein,
(i) the first screening gene is Lc gene, and the second screening gene is Wi2 gene; or
(ii) the first screening gene is interfering RNA of CWI-2 gene, and the second screening gene is Lc gene; or
(iii) the first screening gene is interfering RNA of CWI-2 gene, and the second screening gene is Oy1 gene;
wherein the Lc gene has the nucleotide sequence of SEQ ID NO: 4, the Oy1 gene has the nucleotide sequence of SEQ ID NO: 6, the Wi2 gene has the nucleotide sequence of SEQ ID NO: 8, and the nucleotides encoding the interfering RNA of CWI-2 gene has the nucleotide sequence of SEQ ID NO: 18.

11. The method according to claim 10, wherein:
(i) nucleic acid molecule or the vector comprising the nucleic acid is introduced into the maize cell by an *Agrobacterium*
(ii) the maize cell contains the male sterility gene in a homozygous state in its genome, and is male sterile before introducing the nucleic acid molecule or the vector;
(iii) the nucleic acid molecule is integrated into the genome of the maize cell;
(iv) the nucleic acid molecule is integrated into the genome of the maize plant, and is located on a chromosome different from that of the male sterility gene; and
(v) the maize plant contains the male sterility gene in a homozygous state and the nucleic acid molecule or vector comprising the nucleic acid in a heterozygous form, and it is male fertile.

12. A method for obtaining an offspring maize seed or maize plant of a male sterile line maize and a maintainer line maize, wherein the method comprises: crossing the maize plant according to claim 8 as a male parent with a male sterile maize plant containing the male sterility gene as a female parent, and producing an offspring maize seed or an offspring maize plant.

13. A method for obtaining an offspring maize seed or maize plant of a male sterile line maize and a maintainer line maize, wherein the method comprises:
- (i) providing a male sterile maize plant containing the male sterility gene as a female parent and the maize plant according to claim 8 as a male parent;
- (ii) pollinating the female parent with the male parent to produce two offspring seeds; wherein, the first offspring seeds show the seed external trait regulated by the first screening gene; and, the second offspring seeds do not show the seed external trait regulated by the first screening gene;
- (iii) separating the first and second offspring seeds; and optionally
- (iv) cultivating the first and second offspring seeds into first and second offspring maize plants;
- (v) removing from the first offspring maize plants any maize plant that does not show the maize external trait regulated by the second screening gene, so that the remaining first offspring maize plants are male fertile and can be used as maintainer line maize;
- (vi) removing from the second offspring maize plants any maize plant that shows the maize external trait regulated by the second screening gene, so that the remaining second offspring maize plants are male sterile and can be used as male sterility line maize; and
- (vii) allowing the remaining first offspring maize plants to pollinate the remaining second offspring maize plants to produce further offspring seeds.

14. A method of preparing a hybrid seed, the method comprising:
- (i) providing an offspring seed of a male sterility line maize obtained by the method according to claim 12, which does not show the seed external trait regulated by the first screening gene; and providing a seed of a target line maize;
- (ii) sowing the offspring seed of the male sterility line maize and the seed of the target line maize in a field to obtain the male sterility line maize and the target line maize;
- (iii) removing from the male sterility line maize a maize that shows the maize external trait regulated by the second screening gene;
- (iv) pollinating the remaining male sterility line maize with the target line maize; and
- (v) harvesting a seed from the male sterility line maize, which is the hybrid seed.

15. The method of claim 10, wherein the method further comprises:
- (c) pollinating a male sterile maize plant containing the male sterility gene with the maize plant of step (b) to produce offspring seeds or offspring maize plants; and
- (d) screening the offspring seeds or plants showing the external trait regulated by the first and/or second screening gene.

* * * * *